US012600977B2

(12) United States Patent
Lin et al.

(10) Patent No.: US 12,600,977 B2
(45) Date of Patent: Apr. 14, 2026

(54) PLANTS AND METHODS FOR PRODUCING 2-PYRONE-4, 6-DICARBOXYLIC ACID (PDC)

(71) Applicant: The Regents of the University of California, Oakland, CA (US)

(72) Inventors: Chien-Yuan Lin, Richmond, CA (US); Aymerick Guillaume Eudes, Emeryville, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 552 days.

(21) Appl. No.: 17/501,896

(22) Filed: Oct. 14, 2021

(65) Prior Publication Data

US 2022/0195447 A1 Jun. 23, 2022

Related U.S. Application Data

(60) Provisional application No. 63/091,820, filed on Oct. 14, 2020.

(51) Int. Cl.
*C12N 15/82* (2006.01)
*C12P 17/06* (2006.01)

(52) U.S. Cl.
CPC .......... *C12N 15/8243* (2013.01); *C12P 17/06* (2013.01)

(58) Field of Classification Search
None
See application file for complete search history.

(56) References Cited

U.S. PATENT DOCUMENTS

| | | | |
|---|---|---|---|
| 5,510,471 | A | 4/1996 | Lebrun et al. |
| 2014/0298539 | A1 | 10/2014 | Loque et al. |
| 2015/0051376 | A1 | 2/2015 | Scheller et al. |
| 2016/0017355 | A1 | 1/2016 | Loque et al. |
| 2016/0251672 | A1 | 9/2016 | Loque et al. |

OTHER PUBLICATIONS

LPSN-List of Prokaryotic Names with Standing in Nomenclature; https://lpsn.dsmz.de/; accessed Nov. 16, 2023 (Year: 2023).*
Kasai et al 2009, Journal of Bacteriology 19: 6758-6768) (Year: 2009).*
Wilkes et al, 2001, Phytochemistry 58: 441-449 (Year: 2001).*
Barry et al 2013, Biochemistry 52: 6724-6736 (Year: 2013).*
Peek et al, 2017, Molecular Microbiolgoy 103: 39-54 (Year: 2017).*
Luo et al 2018, ACS Synthetic Biology 7: 2296-2307 (Year: 2018).*
Eudes et al 2015, Plant Biotechnology Journal 13: 1241-1250 (Year: 2015).*
Zhou et al, 2023, Biotechnology for Biofuels and Bioproducts 16:92 (Year: 2023).*
Tzin et al (2012, New Phytologist 194: 430-439). (Year: 2012).*
Uniprot Accession A0A5S4TOR2 (2020, uniprot.org/uniprotkb/A0A5S4TOR2/entry) (Year: 2020).*

Uniprot Accession A0A5S4T2L9 (2020, uniprot.org/uniprotkb/A0A5S4T2L9/entry) (Year: 2020).*
Uniprot Accession A0A076PRN7 (2014, uniprot.org/uniprotkb/A0A076PRN7/entry) (Year: 2014).*
Uniprot Accesion A0A090NFI3 (2014, uniprot.org/uniprotkb/A0A090NFI3/entry) (Year: 2014).*
Uniprot Accession A0A0F6SQM7 (2015, uniprot.org/uniprotkb/A0A0F6SQM7/entry) (Year: 2015).*
Altpeter et al., "Advancing crop transformation in the era of genome editing." Plant Cell 28, 1510-1520 (2016).
Amore et al., "Development of lignocellulosic biorefinery technologies: Recent advances and current challenges." Aust. J. Chem. 69, 1201-1218 (2016).
Aznar et al., "Gene stacking of multiple traits for high yield of fermentable sugars in plant biomass." Biotechnol. Biofuels 11:2 (2018).
Bailey-Serres et al., "Genetic strategies for improving crop yields." Nature 575, 109-118 (2019).
Baral et al., pproaches for more efficient biological conversion of lignocellulosic feedstocks to biofuels and bioproducts. ACS Sustain. Chem. Eng. 7, 9062-9079 (2019).
Bechtold, "In planta Agrobacterium-mediated transformation of adult Arabidopsis thaliana plants by vacuum infiltration." In: Martinez-Zaater, J. M., Salinas, J., Eds.), Arabidopsis Protocols. Humana Press, Totowa, NJ, pp. 259-266 (1998).
Belcher et al., "Design of orthogonal regulatory systems for modulating gene expression in plants." Nat. Chem. Biol. 16, 857-865. (2020).
Bell-Lelong et al., "Cinnamate-4-hydroxylase expression in Arabidopsis. Regulation in response to development and the environment." Plant Physiol. 113, 729-738 (1997).
Bito et al, "2-Pyrone-4,6-dicarboxylic acid as a source of green-plastics and antibacterial chemicals." Trans. Mater. Res. Soc. Japan 33, 1165-1168 (2008).
Bornke et al., "Tailoring plant metabolism for the production of novel polymers and platform chemicals." Curr. Opin. Plant Biol. 13, 354-362 (2010).
Carpita et al., "Redesigning plant cell walls for the biomass-based bioeconomy." J. Biol. Chem. doi: 10.1074/jbc.REV120.014561 (2020).
Eudes et al., "Production of muconic acid in plants." Metab. Eng. 46, 13-19 (2018).
Eudes et al., "Production of hydroxycinnamoyl anthranilates from glucose in *Escherichia coli*. Microb." Cell Fact. 12, 62 (2013).
Eudes et al., "Lignin bioengineering." Curr. Opin. Plant Biol. 26, 189-198 (2014).
Eudes et al., "Exploiting the substrate promiscuity of hydroxycinnamoyl-CoA:shikimate hydroxycinnamoyl transferase to reduce lignin." Plant Cell Physiol. 57, 568-579 (2016).
Eudes et al., "Expression of a bacterial 3-dehydroshikimate dehydratase reduces lignin content and improves biomass saccharification efficiency." Plant Biotechnol. J. 13, 1241-1250 (2015).

(Continued)

*Primary Examiner* — Brent T Page
*Assistant Examiner* — Aleksandar Radosavljevic Radosavljevic
(74) *Attorney, Agent, or Firm* — Robin C. Chiang; LAWRENCE BERKELEY NATIONAL LABORATORY

(57) ABSTRACT

The present invention provides a genetically modified plant or plant cell comprising a nucleic acid encoding one or more heterologous enzymes operably linked a promoter, wherein one or more heterologous enzymes synthesizes 2-pyrone-4, 6-dicarboxylic acid (PDC).

12 Claims, 16 Drawing Sheets

Specification includes a Sequence Listing.

(56) References Cited

OTHER PUBLICATIONS

Hishida et al., "Polyesters of 2-pyrone-4,6-dicarboxylic acid (PDC) as bio-based plastics exhibiting strong adhering properties." Polym. J. 41, 297-302 (2009).

Ishimaru et al., "A rice phenolic efflux transporter is essential for solubilizing precipitated apoplasmic iron in the plant stele." J. Biol. Chem. 286, 24649-24655 (2011).

Jin et al., "The engineered chloroplast genome just got smarter." Trends Plant Sci. 20, 622-640 (2015).

Johnson et al., "Innovative chemicals and materials from bacterial aromatic catabolic pathways." Joule 3, 1523-1537 (2019).

Lin et al., "Strategies for the production of biochemicals in bioenergy crops." Biotechnol Biofuels. 13, 71 (2020).

Loqué et al., "Engineering of plant cell walls for enhanced biofuel production." Curr. Opin. Plant Biol. 25, 151-161 (2015).

Luo et al., "Metabolic engineering of Escherichia coli for efficient production of 2-pyrone-4,6-dicarboxylic acid from glucose." ACS Synth. Biol. 7, 2296-2307 (2018).

Markel et al., "Defining and engineering bioenergy plant feedstock ideotypes." Curr. Opin. Biotech. 62, 196-201 (2020).

Michinobu et al., "Synthesis and characterization of hybrid biopolymers of L-lactic acid and 2-pyrone-4,6-dicarboxylic acid." J. Macromol. Sci. A. 47, 564-570 (2010).

Michinobu et al., "Fusible, elastic, and biodegradable polyesters of 2-pyrone-4,6-dicarboxylic acid (PDC)." Polym. J. 41, 1111-1116 (2009).

Michinobu et al., "Polyesters of 2-pyrone-4,6-dicarboxylic acid (PDC) obtained from a metabolic intermediate of lignin." Polym. J. 40, 68-75 (2008).

Mori et al., "Identification of the protocatechuate transporter gene in *Sphingobium* sp. strain SYK-6 and effects of overexpression on production of a value-added metabolite." Appl. Microbiol. Biotechnol. 102, 4807-4816 (2018).

Nakajima et al., "Microbial conversion of glucose to a novel chemical building block, 2-pyrone-4,6-dicarboxylic acid." Metab. Eng. 11, 213-220 (2009).

Otsuka et al., "Efficient production of 2-pyrone 4,6-dicarboxylic acid as a novel polymer-based material from protocatechuate by microbial function." Appl. Microbiol. Biotechnol. 71, 608-614 (2006).

Parajuli et al., "Towards oilcane: Engineering hyperaccumulation of triacylglycerol into sugarcane stems." GCB Bioenergy 12, 476-490 (2020).

Peña et al., "Arabidopsis irregular xylem8 and irregular xylem9: implications for the complexity of glucuronoxylan biosynthesis." Plant Cell 19, 549-563 (2007).

Perez et al., "Funneling aromatic products of chemically depolymerized lignin into 2-pyrone-4-6-dicarboxylic acid with Novosphingobium aromaticivorans." Green Chem. 21, 1340-1350 (2019).

Qian et al., "Engineered microbial production of 2-pyrone-4, 6-dicarboxylic acid from lignin residues for use as an industrial platform chemical." BioResources. 11, 6097-6109 (2016).

Shih et al., "A robust gene-stacking method utilizing yeast assembly for plant synthetic biology." Nat. Commun. 7, 13215 (2016).

Shikinaka et al., "Thermoplastic polyesters of 2-pyrone-4,6-dicarboxylic acid (PDC) obtained from a metabolic intermediate of lignin." Sen'i Gakkaishi 69, 39-47 (2013).

Shikinaka et al., "Preferential cesium ion trapping by 2-pyrone-4,6-dicarboxylic acid (PDC) obtained from a metabolic intermediate of lignin, a woody biomass resource." J. Nucl. Sci. Technol. 53, 1256-1259 (2016).

Shikinaka et al., "Utilization of lignocellulosic biomass via novel sustainable process." J. Oleo Sci. 67, 1059-1070 (2018).

Snell et al., "Production of novel biopolymers in plants: recent technological advances and future prospects." Curr. Opin. Biotech. 32, 68-75 (2015).

Somleva et al., "Production of polyhydroxybutyrate in switchgrass, a value-added co-product in an important lignocellulosic biomass crop." Plant Biotechnol. J. 6, 663-678 (2008).

Sparkes et al., "Rapid, transient expression of fluorescent fusion proteins in tobacco plants and generation of stably transformed plants." Nat. Protoc. 1, 2019-2025 (2006).

Suzuki et al., "High-throughput determination of thioglycolic acid lignin from rice." Plant Biotechnol. 26, 337-340 (2009).

Tzin et al., "Expression of a bacterial feedback-insensitive 3-deoxy-d-arabino-heptulosonate 7-phosphate synthase of the shikimate pathway in Arabidopsis elucidates potential metabolic bottlenecks between primary and secondary metabolism." New Phytol. 194, 430-439 (2012).

Vanhercke et al., "Metabolic engineering for enhanced oil in biomass. Prog." Lipid Res. 74, 103-129 (2019).

Van Der Weijde et al., "The potential of C4 grasses for cellulosic biofuel production." Front. Plant Sci. 4, 1-18 (2013).

Vaucheret et al., "Transgene-induced gene silencing in plants." Plant J. 16, 651-659 (1998).

Vermaas et al., "Passive membrane transport of lignin-related compounds." Proc. Natl. Acad. Sci. U S A 116, 23117-23123 (2019).

Wilkes et al., "Isolation, characterization, and systematic significance of 2-pyrone-4,6-dicarboxylic acid in Rosaceae." Phytochemistry 58, 441-449 (2001).

Wu et al., "Lignin valorization: Two hybrid biochemical routes for the conversion of polymeric lignin into value-added chemicals." Sci. Rep. 7, 8420 (2017).

Yang et al., "Accumulation of high-value bioproducts in planta can improve the economics of advanced biofuels." Proc. Natl. Acad. Sci. U.S.A 117, 8639-8648 (2020).

Wu, J., et al., 2003. Thermotoga maritima 3-deoxy-D-arabino-heptulosonate 7-phosphate (DAHP) synthase: the ancestral eubacterial DAHP synthase ?. Journal of Biological Chemistry, 278(30), pp. 27525-27531.

Yuan, L. and Grotewold, E., 2015. Metabolic engineering to enhance the value of plants as green factories. Metabolic Engineering, 27, pp. 83-91.

* cited by examiner

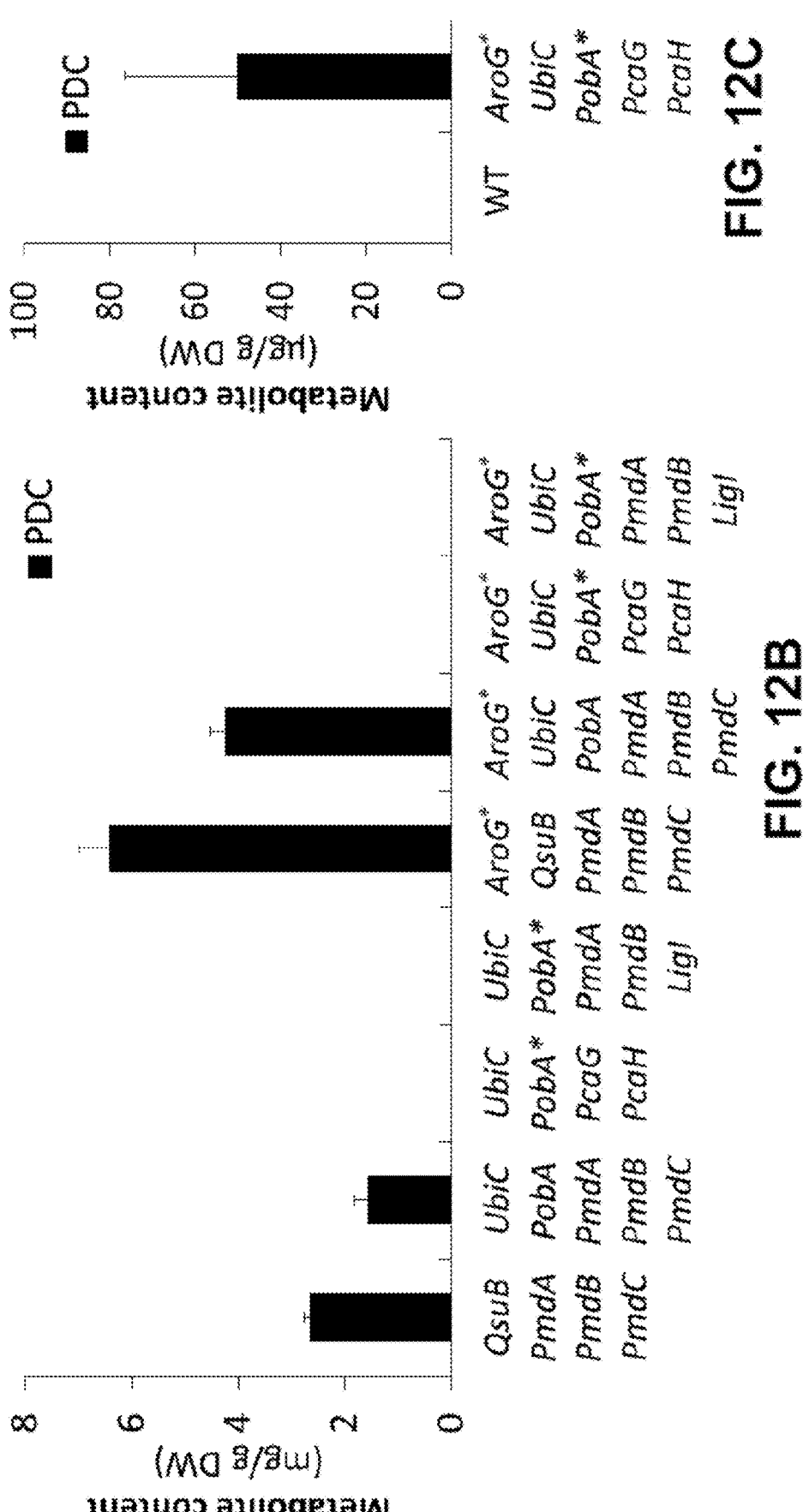

SEQUENCE LISTING

```
<160> NUMBER OF SEQ ID NOS: 106

<210> SEQ ID NO 1
<211> LENGTH: 149
<212> TYPE: PRT
<213> ORGANISM: Comamonas testosteroni

<400> SEQUENCE: 1

Met Ala Leu Glu Lys Pro Tyr Leu Asp Val Pro Gly Thr Ile Ile Phe
1               5                   10                  15

Asp Ala Glu Gln Ser Arg Lys Gly Tyr Trp Leu Asn Gln Phe Cys Met
            20                  25                  30

Ser Leu Met Lys Ala Glu Asn Arg Glu Arg Phe Arg Ala Asp Glu Arg
        35                  40                  45

Ala Tyr Leu Asp Glu Trp Ala Met Thr Glu Glu Gln Lys Gln Ala Val
    50                  55                  60

Leu Ala Arg Asp Leu Asn Trp Cys Met Arg Thr Gly Gly Asn Ile Tyr
65                  70                  75                  80

Phe Leu Ala Lys Ile Gly Ala Thr Asp Gly Lys Ser Phe Gln Gln Met
                85                  90                  95

Ala Gly Ser Met Thr Gly Met Thr Glu Glu Glu Tyr Arg Ala Met Met
            100                 105                 110

Met Gly Gly Gly Arg Ser Ala Glu Gly Asn Arg Tyr Val Gly Glu Asp
        115                 120                 125

Gly Asp Ala Gln Ala His His Gln Pro Gln Gly Ser Ala Gly Asn Gln
    130                 135                 140

Asn Lys Glu Gly Asn
145

<210> SEQ ID NO 2
<211> LENGTH: 289
<212> TYPE: PRT
<213> ORGANISM: Comamonas testosteroni

<400> SEQUENCE: 2

Met Ala Arg Ile Thr Ala Ser Val Phe Thr Ser His Val Pro Ala Ile
1               5                   10                  15

Gly Ala Ala Met Asp Met Gly Lys Thr Gln Glu Ala Tyr Trp Ala Pro
            20                  25                  30
```

-continued

```
Leu Phe Lys Gly Tyr Asp Phe Ser Arg Gln Trp Met Lys Asp Asn Lys
        35              40              45

Pro Asp Val Ile Phe Leu Val Tyr Asn Asp His Ala Thr Ala Phe Ser
    50              55              60

Leu Asp Cys Ile Pro Thr Phe Ala Ile Gly Thr Ala Ala Glu Phe Gln
65              70              75              80

Pro Ala Asp Glu Gly Trp Gly Pro Arg Pro Val Pro Lys Val Val Gly
                85              90              95

His Pro Asp Leu Ala Ser His Ile Ala Gln Ser Val Ile Gln Gln Asp
                100             105             110

Phe Asp Leu Thr Ile Val Asn Lys Met Asp Val Asp His Gly Leu Thr
            115             120             125

Val Pro Leu Ser Leu Met Cys Gly Glu Gln Asp Pro Lys Thr Gly Ser
    130             135             140

Trp Pro Cys Pro Val Ile Pro Phe Ala Val Asn Val Val Gln Tyr Pro
145             150             155             160

Val Pro Thr Gly Gln Arg Cys Phe Asn Leu Gly Arg Ala Ile Arg Lys
                165             170             175

Ala Val Glu Ser Tyr Asp Gln Asp Ile Asn Val His Ile Trp Gly Thr
                180             185             190

Gly Gly Met Ser His Gln Leu Gln Gly Ala Arg Ala Gly Leu Ile Asn
            195             200             205

Lys Glu Trp Asp Asn Gln Phe Leu Asp Leu Leu Val Glu Asn Pro His
    210             215             220

Gly Leu Ala Gln Met Pro His Ile Asp Tyr Val Arg Glu Ala Gly Ser
225             230             235             240

Glu Gly Ile Glu Leu Val Met Trp Leu Ile Ala Arg Gly Ala Met Ser
                245             250             255

Asp Val Asp Gly Pro Ala Pro Leu Pro Lys Val Ala His Arg Phe Tyr
                260             265             270

His Val Pro Ala Ser Asn Thr Ala Val Gly His Leu Ile Leu Glu Asn
    275             280             285

Gln
```

```
<210> SEQ ID NO 3
<211> LENGTH: 319
<212> TYPE: PRT
<213> ORGANISM: Comamonas testosteroni

<400> SEQUENCE: 3

Met Ser Lys Thr Ile Lys Val Ala Leu Ala Gly Ala Gly Ala Phe Gly
1               5               10              15

Ile Lys His Leu Asp Gly Ile Lys Asn Ile Asp Gly Val Glu Val Val
            20              25              30

Ser Leu Val Gly Arg Arg Phe Asp Gln Thr Lys Glu Val Ala Asp Lys
        35              40              45

Tyr Gly Ile Ala His Val Ala Thr Asp Leu Ala Glu Ser Leu Ala Leu
    50              55              60

Pro Glu Val Asp Ala Val Ile Leu Cys Thr Pro Thr Gln Met His Ala
65              70              75              80

Glu Gln Ala Ile Ala Cys Met Lys Ala Gly Lys His Val Gln Val Glu
                85              90              95

Ile Pro Leu Ala Asp Ala Leu Lys Asp Ala Gln Glu Val Ala Glu Leu
                100             105             110
```

-continued

```
Gln Lys Gln Thr Gly Leu Val Ala Met Val Gly His Thr Arg Arg Phe
        115                 120                 125

Asn Pro Ser His Gln Trp Val His Lys Lys Ile Glu Ala Gly Glu Phe
        130                 135                 140

Asn Ile Gln Gln Met Asp Val Gln Thr Tyr Phe Phe Arg Arg Thr Asn
145                 150                 155                 160

Met Asn Ala Leu Gly Gln Ala Arg Ser Trp Thr Asp His Leu Leu Trp
                165                 170                 175

His His Ala Ala His Thr Val Asp Leu Phe Ala Tyr Gln Ala Gly Ser
        180                 185                 190

Pro Ile Val Lys Ala Asn Ala Val Gln Gly Pro Ile His Lys Asp Leu
        195                 200                 205

Gly Ile Ala Met Asp Met Ser Ile Gln Leu Lys Ala Ala Asn Gly Ala
        210                 215                 220

Ile Cys Thr Leu Ser Leu Ser Phe Asn Asn Asp Gly Pro Leu Gly Thr
225                 230                 235                 240

Phe Phe Arg Tyr Ile Gly Asp Thr Gly Thr Tyr Leu Ala Arg Tyr Asp
                245                 250                 255

Asp Leu Tyr Thr Gly Lys Asp Glu Lys Ile Asp Val Ser Gln Val Asp
        260                 265                 270

Val Ser Met Asn Gly Ile Glu Leu Gln Asp Arg Glu Phe Phe Ala Ala
        275                 280                 285

Ile Arg Glu Gly Arg Glu Pro Asn Ser Ser Val Gln Gln Val Phe Asn
        290                 295                 300

Cys Tyr Lys Val Leu His Asp Leu Glu Gln Gln Leu Asn Ala Asp
305                 310                 315

<210> SEQ ID NO 4
<211> LENGTH: 350
<212> TYPE: PRT
<213> ORGANISM: Escherichia coli

<400> SEQUENCE: 4

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
                20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
        50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
        100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
        130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
```

```
                    165                 170                 175
Ser Gly Leu Ser Cys Pro Val Gly Phe Lys Asn Gly Thr Asp Gly Thr
                180                 185                 190

Ile Lys Val Ala Ile Asp Ala Ile Asn Ala Ala Gly Ala Pro His Cys
            195                 200                 205

Phe Leu Ser Val Thr Lys Trp Gly His Ser Ala Ile Val Asn Thr Ser
        210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
        290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350

<210> SEQ ID NO 5
<211> LENGTH: 350
<212> TYPE: PRT
<213> ORGANISM: Escherichia coli

<400> SEQUENCE: 5

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
                20                  25                  30

Ala Asn Thr Val Ala His Ala Arg Lys Ala Ile His Lys Ile Leu Lys
            35                  40                  45

Gly Asn Asp Asp Arg Leu Leu Val Val Ile Gly Pro Cys Ser Ile His
        50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
    130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Gln Ala
                165                 170                 175

Ser Gly Leu Ser Cys Pro Val Gly Phe Lys Asn Gly Thr Asp Gly Thr
                180                 185                 190
```

```
Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
        210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
                260                 265                 270

Lys Gln Phe Lys Lys Gln Met Asp Val Cys Ala Asp Val Cys Gln Gln
                275                 280                 285

Ile Ala Gly Gly Glu Lys Ala Ile Ile Gly Val Met Val Glu Ser His
        290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
                340                 345                 350

<210> SEQ ID NO 6
<211> LENGTH: 394
<212> TYPE: PRT
<213> ORGANISM: Pseudomonas aeruginosa

<400> SEQUENCE: 6

Met Lys Thr Gln Val Ala Ile Ile Gly Ala Gly Pro Ser Gly Leu Leu
1               5                   10                  15

Leu Gly Gln Leu Leu His Lys Ala Gly Ile Asp Asn Val Ile Leu Glu
                20                  25                  30

Arg Gln Thr Pro Asp Tyr Val Leu Gly Arg Ile Arg Ala Gly Val Leu
            35                  40                  45

Glu Gln Gly Met Val Asp Leu Leu Arg Glu Ala Gly Val Asp Arg Arg
        50                  55                  60

Met Ala Arg Asp Gly Leu Val His Glu Gly Val Glu Ile Ala Phe Ala
65                  70                  75                  80

Gly Gln Arg Arg Arg Ile Asp Leu Lys Arg Leu Ser Gly Gly Lys Thr
                85                  90                  95

Val Thr Val Tyr Gly Gln Thr Glu Val Thr Arg Asp Leu Met Glu Ala
                100                 105                 110

Arg Glu Ala Cys Gly Ala Thr Thr Val Tyr Gln Ala Ala Glu Val Arg
            115                 120                 125

Leu His Asp Leu Gln Gly Glu Arg Pro Tyr Val Thr Phe Glu Arg Asp
        130                 135                 140

Gly Glu Arg Leu Arg Leu Asp Cys Asp Tyr Ile Ala Gly Cys Asp Gly
145                 150                 155                 160

Phe His Gly Ile Ser Arg Gln Ser Ile Pro Ala Glu Arg Leu Lys Val
                165                 170                 175

Phe Glu Arg Val Tyr Pro Phe Gly Trp Leu Gly Leu Leu Ala Asp Thr
                180                 185                 190

Pro Pro Val Ser His Glu Leu Ile Tyr Ala Asn His Pro Arg Gly Phe
            195                 200                 205

Ala Leu Cys Ser Gln Arg Ser Ala Thr Arg Ser Arg Tyr Tyr Val Gln
        210                 215                 220
```

-continued

```
Val Pro Leu Thr Glu Lys Val Glu Asp Trp Ser Asp Glu Arg Phe Trp
225                 230                 235                 240

Thr Glu Leu Lys Ala Arg Leu Pro Ala Glu Val Ala Glu Lys Leu Val
                245                 250                 255

Thr Gly Pro Ser Leu Glu Lys Ser Ile Ala Pro Leu Arg Ser Phe Val
                260                 265                 270

Val Glu Pro Met Gln His Gly Arg Leu Phe Leu Ala Gly Asp Ala Ala
                275                 280                 285

His Ile Val Pro Pro Thr Gly Ala Lys Gly Leu Asn Leu Ala Ala Ser
                290                 295                 300

Asp Val Ser Thr Leu Tyr Arg Leu Leu Leu Lys Ala Tyr Arg Glu Gly
305                 310                 315                 320

Arg Gly Glu Leu Leu Glu Arg Tyr Ser Ala Ile Cys Leu Arg Arg Ile
                325                 330                 335

Trp Lys Ala Glu Arg Phe Ser Trp Trp Met Thr Ser Val Leu His Arg
                340                 345                 350

Phe Pro Asp Thr Asp Ala Phe Ser Gln Arg Ile Gln Gln Thr Glu Leu
                355                 360                 365

Glu Tyr Tyr Leu Gly Ser Glu Ala Gly Leu Ala Thr Ile Ala Glu Asn
                370                 375                 380

Tyr Val Gly Leu Pro Tyr Glu Glu Ile Glu
385                 390
```

```
<210> SEQ ID NO 7
<211> LENGTH: 394
<212> TYPE: PRT
<213> ORGANISM: Pseudomonas aeruginosa

<400> SEQUENCE: 7
```

```
Met Lys Thr Gln Val Ala Ile Ile Gly Ala Gly Pro Ser Gly Leu Leu
1                   5                   10                  15

Leu Gly Gln Leu Leu His Lys Ala Gly Ile Asp Asn Val Ile Leu Glu
                20                  25                  30

Arg Gln Thr Pro Asp Tyr Val Leu Gly Arg Ile Arg Ala Gly Val Leu
                35                  40                  45

Glu Gln Gly Met Val Asp Leu Leu Arg Glu Ala Gly Val Asp Arg Arg
        50                  55                  60

Met Ala Arg Asp Gly Leu Val His Glu Gly Val Glu Ile Ala Phe Ala
65                  70                  75                  80

Gly Gln Arg Arg Arg Ile Asp Leu Lys Arg Leu Ser Gly Gly Lys Thr
                85                  90                  95

Val Thr Val Tyr Gly Gln Thr Glu Val Thr Arg Asp Leu Met Glu Ala
                100                 105                 110

Arg Glu Ala Cys Gly Ala Thr Thr Val Tyr Gln Ala Ala Glu Val Arg
                115                 120                 125

Leu His Asp Leu Gln Gly Glu Arg Pro Tyr Val Thr Phe Glu Arg Asp
        130                 135                 140

Gly Glu Arg Leu Arg Leu Asp Cys Asp Tyr Ile Ala Gly Cys Asp Gly
145                 150                 155                 160

Phe His Gly Ile Ser Arg Gln Ser Ile Pro Ala Glu Arg Leu Lys Val
                165                 170                 175

Phe Glu Arg Val Tyr Pro Phe Gly Trp Leu Gly Leu Leu Ala Asp Thr
                180                 185                 190

Pro Pro Val Ser His Glu Leu Ile Tyr Ala Asn His Pro Arg Gly Phe
```

-continued

```
            195                 200                 205
Ala Leu Cys Ser Gln Arg Ser Ala Thr Arg Ser Arg Tyr Tyr Val Gln
    210                 215                 220

Val Pro Leu Thr Glu Lys Val Glu Asp Trp Ser Asp Glu Arg Phe Trp
225                 230                 235                 240

Thr Glu Leu Lys Ala Arg Leu Pro Ala Glu Val Ala Glu Lys Leu Val
                245                 250                 255

Thr Gly Pro Ser Leu Glu Lys Ser Ile Ala Pro Leu Arg Ser Phe Val
                260                 265                 270

Val Glu Pro Met Gln His Gly Arg Leu Phe Leu Ala Gly Asp Ala Ala
                275                 280                 285

His Ile Val Pro Pro Ala Gly Ala Lys Gly Leu Asn Leu Ala Ala Ser
    290                 295                 300

Asp Val Ser Thr Leu Tyr Arg Leu Leu Leu Lys Ala Tyr Arg Glu Gly
305                 310                 315                 320

Arg Gly Glu Leu Leu Glu Arg Tyr Ser Ala Ile Cys Leu Arg Arg Ile
                325                 330                 335

Trp Lys Ala Glu Arg Phe Ser Trp Trp Met Thr Ser Val Leu His Arg
                340                 345                 350

Phe Pro Asp Thr Asp Ala Phe Ser Gln Arg Ile Gln Gln Thr Glu Leu
                355                 360                 365

Glu Tyr Tyr Leu Gly Ser Glu Ala Gly Leu Ala Thr Ile Ala Glu Asn
    370                 375                 380

Phe Val Gly Leu Pro Tyr Glu Glu Ile Glu
385                 390
```

```
<210> SEQ ID NO 8
<211> LENGTH: 201
<212> TYPE: PRT
<213> ORGANISM: Escherichia coli

<400> SEQUENCE: 8

Met Pro Ile Glu Leu Leu Pro Glu Thr Pro Ser Gln Thr Ala Gly Pro
1               5                   10                  15

Tyr Val His Ile Gly Leu Ala Leu Glu Ala Ala Gly Asn Pro Thr Arg
            20                  25                  30

Asp Gln Glu Ile Trp Asn Cys Leu Ala Lys Pro Asp Ala Pro Gly Glu
        35                  40                  45

His Ile Leu Leu Ile Gly His Val Tyr Asp Gly Asn Gly His Leu Val
    50                  55                  60

Arg Asp Ser Phe Leu Glu Val Trp Gln Ala Asp Ala Asn Gly Glu Tyr
65                  70                  75                  80

Gln Asp Ala Tyr Asn Leu Glu Asn Ala Phe Asn Ser Phe Gly Arg Thr
                85                  90                  95

Ala Thr Thr Phe Asp Ala Gly Glu Trp Thr Leu Gln Thr Val Lys Pro
            100                 105                 110

Gly Val Val Asn Asn Ala Ala Gly Val Pro Met Ala Pro His Ile Asn
            115                 120                 125

Ile Ser Leu Phe Ala Arg Gly Ile Asn Ile His Leu His Thr Arg Leu
    130                 135                 140

Tyr Phe Asp Asp Glu Ala Gln Ala Asn Ala Lys Cys Pro Val Leu Asn
145                 150                 155                 160

Leu Ile Glu Gln Pro Gln Arg Arg Glu Thr Leu Ile Ala Lys Arg Cys
                165                 170                 175
```

```
Glu Val Asp Gly Lys Thr Ala Tyr Arg Phe Asp Ile Arg Ile Gln Gly
            180                 185                 190

Glu Gly Glu Thr Val Phe Phe Asp Phe
        195                 200

<210> SEQ ID NO 9
<211> LENGTH: 239
<212> TYPE: PRT
<213> ORGANISM: Escherichia coli

<400> SEQUENCE: 9

Met Pro Ala Gln Asp Asn Ser Arg Phe Val Ile Arg Asp Arg Asn Trp
1               5                   10                  15

His Pro Lys Ala Leu Thr Pro Asp Tyr Lys Thr Ser Val Ala Arg Ser
            20                  25                  30

Pro Arg Gln Ala Leu Val Ser Ile Pro Gln Ser Ile Ser Glu Thr Thr
            35                  40                  45

Gly Pro Asp Phe Ser His Leu Gly Phe Gly Ala His Asp His Asp Leu
    50                  55                  60

Leu Leu Asn Phe Asn Asn Gly Gly Leu Pro Ile Gly Glu Arg Ile Ile
65                  70                  75                  80

Val Ala Gly Arg Val Val Asp Gln Tyr Gly Lys Pro Val Pro Asn Thr
                85                  90                  95

Leu Val Glu Met Trp Gln Ala Asn Ala Gly Gly Arg Tyr Arg His Lys
            100                 105                 110

Asn Asp Arg Tyr Leu Ala Pro Leu Asp Pro Asn Phe Gly Gly Val Gly
            115                 120                 125

Arg Cys Leu Thr Asp Arg Asp Gly Tyr Tyr Ser Phe Arg Thr Ile Lys
        130                 135                 140

Pro Gly Pro Tyr Pro Trp Arg Asn Gly Pro Asn Asp Trp Arg Pro Ala
145                 150                 155                 160

His Ile His Phe Ala Ile Ser Gly Pro Ser Ile Ala Thr Lys Leu Ile
                165                 170                 175

Thr Gln Leu Tyr Phe Glu Gly Asp Pro Leu Ile Pro Met Cys Pro Ile
            180                 185                 190

Val Lys Ser Ile Ala Asn Pro Gln Ala Val Gln Gln Leu Ile Ala Lys
            195                 200                 205

Leu Asp Met Ser Asn Ala Asn Pro Met Asp Cys Leu Ala Tyr Arg Phe
        210                 215                 220

Asp Ile Val Leu Arg Gly Gln Arg Lys Thr His Phe Glu Asn Cys
225                 230                 235

<210> SEQ ID NO 10
<211> LENGTH: 293
<212> TYPE: PRT
<213> ORGANISM: Sphingomonas paucimobilis

<400> SEQUENCE: 10

Met Thr Asn Asp Glu Arg Ile Leu Ser Trp Asn Glu Thr Pro Ser Lys
1               5                   10                  15

Pro Arg Tyr Thr Pro Pro Gly Ala Ile Asp Ala His Cys His Val
            20                  25                  30

Phe Gly Pro Met Ala Gln Phe Pro Phe Ser Pro Lys Ala Lys Tyr Leu
            35                  40                  45

Pro Arg Asp Ala Gly Pro Asp Met Leu Phe Ala Leu Arg Asp His Leu
    50                  55                  60
```

-continued

```
Gly Phe Ala Arg Asn Val Ile Val Gln Ala Ser Cys His Gly Thr Asp
65                  70                  75                  80

Asn Ala Ala Thr Leu Asp Ala Ile Ala Arg Ala Gln Gly Lys Ala Arg
                85                  90                  95

Gly Ile Ala Val Val Asp Pro Ala Ile Asp Glu Ala Glu Leu Ala Ala
            100                 105                 110

Leu His Glu Gly Gly Met Arg Gly Ile Arg Phe Asn Phe Leu Lys Arg
            115                 120                 125

Leu Val Asp Asp Ala Pro Lys Asp Lys Phe Leu Glu Val Ala Gly Arg
            130                 135                 140

Leu Pro Ala Gly Trp His Val Val Ile Tyr Phe Glu Ala Asp Ile Leu
145                 150                 155                 160

Glu Glu Leu Arg Pro Phe Met Asp Ala Ile Pro Val Pro Ile Val Ile
                165                 170                 175

Asp His Met Gly Arg Pro Asp Val Arg Gln Gly Pro Asp Gly Ala Asp
            180                 185                 190

Met Lys Ala Phe Arg Arg Leu Leu Asp Ser Arg Glu Asp Ile Trp Phe
            195                 200                 205

Lys Ala Thr Cys Pro Asp Arg Leu Asp Pro Ala Gly Pro Pro Trp Asp
            210                 215                 220

Asp Phe Ala Arg Ser Val Ala Pro Leu Val Ala Asp Tyr Ala Asp Arg
225                 230                 235                 240

Val Ile Trp Gly Thr Asp Trp Pro His Pro Asn Met Gln Asp Ala Ile
                245                 250                 255

Pro Asp Asp Gly Leu Val Val Asp Met Ile Pro Arg Ile Ala Pro Thr
            260                 265                 270

Pro Glu Leu Gln His Lys Met Leu Val Thr Asn Pro Met Arg Leu Tyr
            275                 280                 285

Trp Ser Glu Glu Met
            290
```

```
<210> SEQ ID NO 11
<211> LENGTH: 618
<212> TYPE: PRT
<213> ORGANISM: Corynebacterium glutamicum

<400> SEQUENCE: 11
```

```
Met Arg Thr Ser Ile Ala Thr Val Cys Leu Ser Gly Thr Leu Ala Glu
1               5                   10                  15

Lys Leu Arg Ala Ala Ala Asp Ala Gly Phe Asp Gly Val Glu Ile Phe
                20                  25                  30

Glu Gln Asp Leu Val Val Ser Pro His Ser Ala Glu Gln Ile Arg Gln
            35                  40                  45

Arg Ala Gln Asp Leu Gly Leu Thr Leu Asp Leu Phe Gln Pro Phe Arg
            50                  55                  60

Asp Phe Glu Gly Val Glu Glu Glu Gln Phe Leu Lys Asn Leu His Arg
65                  70                  75                  80

Leu Glu Glu Lys Phe Lys Leu Met Asn Arg Leu Gly Ile Glu Met Ile
                85                  90                  95

Leu Leu Cys Ser Asn Val Gly Thr Ala Thr Ile Asn Asp Asp Asp Leu
            100                 105                 110

Phe Ala Glu Gln Leu His Arg Ala Ala Asp Leu Ala Glu Lys Tyr Asn
            115                 120                 125

Val Lys Ile Ala Tyr Glu Ala Leu Ala Trp Gly Lys Phe Val Asn Asp
            130                 135                 140
```

```
Phe Glu His Ala His Ala Leu Val Glu Lys Val Asn His Lys Ala Leu
145                 150                 155                 160

Gly Thr Cys Leu Asp Thr Phe His Ile Leu Ser Arg Gly Trp Glu Thr
                165                 170                 175

Asp Glu Val Glu Asn Ile Pro Ala Glu Lys Ile Phe Phe Val Gln Leu
                180                 185                 190

Ala Asp Ala Pro Lys Leu Ser Met Asp Ile Leu Ser Trp Ser Arg His
                195                 200                 205

His Arg Val Phe Pro Gly Glu Gly Asp Phe Asp Leu Val Lys Phe Met
        210                 215                 220

Val His Leu Ala Lys Thr Gly Tyr Asp Gly Pro Ile Ser Leu Glu Ile
225                 230                 235                 240

Phe Asn Asp Ser Phe Arg Lys Ala Glu Val Gly Arg Thr Ala Ile Asp
                245                 250                 255

Gly Leu Arg Ser Leu Arg Trp Leu Glu Asp Gln Thr Trp His Ala Leu
                260                 265                 270

Ser Ala Glu Asp Arg Pro Ser Ala Leu Glu Leu Arg Ala Leu Pro Glu
        275                 280                 285

Val Ala Glu Pro Glu Gly Val Asp Phe Ile Glu Ile Ala Thr Gly Arg
        290                 295                 300

Leu Gly Glu Thr Ile Arg Val Leu His Gln Leu Gly Phe Arg Leu Gly
305                 310                 315                 320

Gly His His Cys Ser Lys Gln Asp Tyr Gln Val Trp Thr Gln Gly Asp
                325                 330                 335

Val Arg Ile Val Val Cys Asp Arg Gly Ala Thr Gly Ala Pro Thr Thr
                340                 345                 350

Ile Ser Ala Met Gly Phe Asp Thr Pro Asp Pro Glu Ala Ala His Ala
                355                 360                 365

Arg Ala Glu Leu Leu Arg Ala Gln Thr Ile Asp Arg Pro His Ile Glu
        370                 375                 380

Gly Glu Val Asp Leu Lys Gly Val Tyr Ala Pro Asp Gly Val Glu Leu
385                 390                 395                 400

Phe Phe Ala Gly Pro Ser Pro Asp Gly Met Pro Glu Trp Leu Pro Glu
                405                 410                 415

Phe Gly Val Glu Lys Gln Glu Ala Gly Leu Ile Glu Ala Ile Asp His
                420                 425                 430

Val Asn Phe Ala Gln Pro Trp Gln His Phe Asp Glu Ala Val Leu Phe
        435                 440                 445

Tyr Thr Ala Leu Met Ala Leu Glu Thr Val Arg Glu Asp Glu Phe Pro
        450                 455                 460

Ser Pro Ile Gly Leu Val Arg Asn Gln Val Met Arg Ser Pro Asn Asp
465                 470                 475                 480

Ala Val Arg Leu Leu Leu Ser Val Ala Pro Glu Asp Gly Glu Gln Gly
                485                 490                 495

Asp Phe Leu Asn Ala Ala Tyr Pro Glu His Ile Ala Leu Ala Thr Ala
                500                 505                 510

Asp Ile Val Ala Val Ala Glu Arg Ala Arg Lys Arg Gly Leu Asp Phe
                515                 520                 525

Leu Pro Val Pro Glu Asn Tyr Tyr Asp Asp Val Gln Ala Arg Phe Asp
        530                 535                 540

Leu Pro Gln Glu Phe Leu Asp Thr Leu Lys Glu Asn His Leu Leu Tyr
545                 550                 555                 560
```

```
Asp Arg Asp Glu Asn Gly Glu Phe Leu His Phe Tyr Thr Arg Thr Leu
                565                 570                 575

Gly Thr Leu Phe Phe Glu Val Val Glu Arg Arg Gly Gly Phe Ala Gly
            580                 585                 590

Trp Gly Glu Thr Asn Ala Pro Val Arg Leu Ala Ala Gln Tyr Arg Glu
        595                 600                 605

Val Arg Asp Leu Glu Arg Gly Ile Pro Asn
    610                 615

<210> SEQ ID NO 12
<211> LENGTH: 9
<212> TYPE: PRT
<213> ORGANISM: Comamonas testosteroni

<400> SEQUENCE: 12

Lys Pro Tyr Leu Asp Val Pro Gly Thr
1               5

<210> SEQ ID NO 13
<211> LENGTH: 29
<212> TYPE: PRT
<213> ORGANISM: Comamonas testosteroni

<400> SEQUENCE: 13

Ile Phe Asp Ala Glu Gln Ser Arg Lys Gly Tyr Trp Leu Asn Gln Phe
1               5                   10                  15

Cys Met Ser Leu Met Lys Ala Glu Asn Arg Glu Arg Phe
            20                  25

<210> SEQ ID NO 14
<211> LENGTH: 27
<212> TYPE: PRT
<213> ORGANISM: Comamonas testosteroni

<400> SEQUENCE: 14

Asp Glu Arg Ala Tyr Leu Asp Glu Trp Ala Met Thr Glu Glu Gln Lys
1               5                   10                  15

Gln Ala Val Leu Ala Arg Asp Leu Asn Trp Cys
            20                  25

<210> SEQ ID NO 15
<211> LENGTH: 34
<212> TYPE: PRT
<213> ORGANISM: Comamonas testosteroni

<400> SEQUENCE: 15

Gly Gly Asn Ile Tyr Phe Leu Ala Lys Ile Gly Ala Thr Asp Gly Lys
1               5                   10                  15

Ser Phe Gln Gln Met Ala Gly Ser Met Thr Gly Met Thr Glu Glu Glu
            20                  25                  30

Tyr Arg

<210> SEQ ID NO 16
<211> LENGTH: 5
<212> TYPE: PRT
<213> ORGANISM: Comamonas testosteroni

<400> SEQUENCE: 16

Gly Gly Arg Ser Ala
1               5
```

-continued

```
<210> SEQ ID NO 17
<211> LENGTH: 10
<212> TYPE: PRT
<213> ORGANISM: Comamonas testosteroni

<400> SEQUENCE: 17

Val Gly Glu Asp Gly Asp Ala Gln Ala His
1               5                   10

<210> SEQ ID NO 18
<211> LENGTH: 8
<212> TYPE: PRT
<213> ORGANISM: Comamonas testosteroni

<400> SEQUENCE: 18

Met Ala Arg Ile Thr Ala Ser Val
1               5

<210> SEQ ID NO 19
<211> LENGTH: 10
<212> TYPE: PRT
<213> ORGANISM: Comamonas testosteroni

<400> SEQUENCE: 19

Thr Ser His Val Pro Ala Ile Gly Ala Ala
1               5                   10

<210> SEQ ID NO 20
<211> LENGTH: 18
<212> TYPE: PRT
<213> ORGANISM: Comamonas testosteroni

<400> SEQUENCE: 20

Pro Asp Val Ile Phe Leu Val Tyr Asn Asp His Ala Thr Ala Phe Ser
1               5                   10                  15

Leu Asp

<210> SEQ ID NO 21
<211> LENGTH: 12
<212> TYPE: PRT
<213> ORGANISM: Comamonas testosteroni

<400> SEQUENCE: 21

Ile Pro Thr Phe Ala Ile Gly Thr Ala Ala Glu Phe
1               5                   10

<210> SEQ ID NO 22
<211> LENGTH: 12
<212> TYPE: PRT
<213> ORGANISM: Comamonas testosteroni

<400> SEQUENCE: 22

Ile Pro Thr Phe Ala Ile Gly Thr Ala Ala Glu Phe
1               5                   10

<210> SEQ ID NO 23
<211> LENGTH: 11
<212> TYPE: PRT
<213> ORGANISM: Comamonas testosteroni

<400> SEQUENCE: 23

Leu Ala Ser His Ile Ala Gln Ser Val Ile Gln
1               5                   10
```

-continued

```
<210> SEQ ID NO 24
<211> LENGTH: 26
<212> TYPE: PRT
<213> ORGANISM: Comamonas testosteroni

<400> SEQUENCE: 24

Asp Phe Asp Leu Thr Ile Val Asn Lys Met Asp Val Asp His Gly Leu
1               5                   10                  15

Thr Val Pro Leu Ser Leu Met Cys Gly Glu
            20                  25

<210> SEQ ID NO 25
<211> LENGTH: 14
<212> TYPE: PRT
<213> ORGANISM: Comamonas testosteroni

<400> SEQUENCE: 25

Val Ile Pro Phe Ala Val Asn Val Val Gln Tyr Pro Val Pro
1               5                   10

<210> SEQ ID NO 26
<211> LENGTH: 20
<212> TYPE: PRT
<213> ORGANISM: Comamonas testosteroni

<400> SEQUENCE: 26

Ile Trp Gly Thr Gly Gly Met Ser His Gln Leu Gln Gly Ala Arg Ala
1               5                   10                  15

Gly Leu Ile Asn
            20

<210> SEQ ID NO 27
<211> LENGTH: 22
<212> TYPE: PRT
<213> ORGANISM: Comamonas testosteroni

<400> SEQUENCE: 27

Tyr Val Arg Glu Ala Gly Ser Glu Gly Ile Glu Leu Val Met Trp Leu
1               5                   10                  15

Ile Ala Arg Gly Ala Met
            20

<210> SEQ ID NO 28
<211> LENGTH: 16
<212> TYPE: PRT
<213> ORGANISM: Comamonas testosteroni

<400> SEQUENCE: 28

His Val Pro Ala Ser Asn Thr Ala Val Gly His Leu Ile Leu Glu Asn
1               5                   10                  15

<210> SEQ ID NO 29
<211> LENGTH: 9
<212> TYPE: PRT
<213> ORGANISM: Comamonas testosteroni

<400> SEQUENCE: 29

Ala Leu Ala Gly Ala Gly Ala Phe Gly
1               5

<210> SEQ ID NO 30
<211> LENGTH: 7
<212> TYPE: PRT
<213> ORGANISM: Comamonas testosteroni
```

```
<400> SEQUENCE: 30

Lys Asn Ile Asp Gly Val Glu
1               5

<210> SEQ ID NO 31
<211> LENGTH: 21
<212> TYPE: PRT
<213> ORGANISM: Comamonas testosteroni

<400> SEQUENCE: 31

Val Asp Ala Val Ile Leu Cys Thr Pro Thr Gln Met His Ala Glu Gln
1               5                   10                  15

Ala Ile Ala Cys Met
            20

<210> SEQ ID NO 32
<211> LENGTH: 13
<212> TYPE: PRT
<213> ORGANISM: Comamonas testosteroni

<400> SEQUENCE: 32

Ala Gly Lys His Val Gln Val Glu Ile Pro Leu Ala Asp
1               5                   10

<210> SEQ ID NO 33
<211> LENGTH: 13
<212> TYPE: PRT
<213> ORGANISM: Comamonas testosteroni

<400> SEQUENCE: 33

Ile Gln Gln Met Asp Val Gln Thr Tyr Phe Phe Arg Arg
1               5                   10

<210> SEQ ID NO 34
<211> LENGTH: 13
<212> TYPE: PRT
<213> ORGANISM: Comamonas testosteroni

<400> SEQUENCE: 34

Ile Gln Gln Met Asp Val Gln Thr Tyr Phe Phe Arg Arg
1               5                   10

<210> SEQ ID NO 35
<211> LENGTH: 24
<212> TYPE: PRT
<213> ORGANISM: Comamonas testosteroni

<400> SEQUENCE: 35

Arg Ser Trp Thr Asp His Leu Leu Trp His His Ala Ala His Thr Val
1               5                   10                  15

Asp Leu Phe Ala Tyr Gln Ala Gly
            20

<210> SEQ ID NO 36
<211> LENGTH: 9
<212> TYPE: PRT
<213> ORGANISM: Comamonas testosteroni

<400> SEQUENCE: 36

Ala Asn Ala Val Gln Gly Pro Ile His
1               5
```

```
<210> SEQ ID NO 37
<211> LENGTH: 12
<212> TYPE: PRT
<213> ORGANISM: Comamonas testosteroni

<400> SEQUENCE: 37

Leu Gly Ile Ala Met Asp Met Ser Ile Gln Leu Lys
1               5                   10

<210> SEQ ID NO 38
<211> LENGTH: 23
<212> TYPE: PRT
<213> ORGANISM: Comamonas testosteroni

<400> SEQUENCE: 38

Gly Ala Ile Cys Thr Leu Ser Leu Ser Phe Asn Asn Asp Gly Pro Leu
1               5                   10                  15

Gly Thr Phe Phe Arg Tyr Ile
            20

<210> SEQ ID NO 39
<211> LENGTH: 6
<212> TYPE: PRT
<213> ORGANISM: Comamonas testosteroni

<400> SEQUENCE: 39

Ala Arg Tyr Asp Asp Leu
1               5

<210> SEQ ID NO 40
<211> LENGTH: 15
<212> TYPE: PRT
<213> ORGANISM: Comamonas testosteroni

<400> SEQUENCE: 40

Val Asp Val Ser Met Asn Gly Ile Glu Leu Gln Asp Arg Glu Phe
1               5                   10                  15

<210> SEQ ID NO 41
<211> LENGTH: 13
<212> TYPE: PRT
<213> ORGANISM: Comamonas testosteroni

<400> SEQUENCE: 41

Ala Ala Ile Arg Glu Gly Arg Glu Pro Asn Ser Ser Val
1               5                   10

<210> SEQ ID NO 42
<211> LENGTH: 10
<212> TYPE: PRT
<213> ORGANISM: Escherichia coli

<400> SEQUENCE: 42

Met Arg Val Tyr Phe Glu Lys Pro Arg Thr
1               5                   10

<210> SEQ ID NO 43
<211> LENGTH: 8
<212> TYPE: PRT
<213> ORGANISM: Escherichia coli

<400> SEQUENCE: 43

Val Gly Trp Lys Gly Leu Ile Asn
1               5
```

-continued

```
<210> SEQ ID NO 44
<211> LENGTH: 7
<212> TYPE: PRT
<213> ORGANISM: Escherichia coli

<400> SEQUENCE: 44

Gly Leu Arg Ile Ala Arg Lys
1               5

<210> SEQ ID NO 45
<211> LENGTH: 15
<212> TYPE: PRT
<213> ORGANISM: Escherichia coli

<400> SEQUENCE: 45

Trp Gly Ala Ile Gly Ala Arg Thr Thr Glu Ser Gln Val His Arg
1               5               10              15

<210> SEQ ID NO 46
<211> LENGTH: 7
<212> TYPE: PRT
<213> ORGANISM: Escherichia coli

<400> SEQUENCE: 46

His Ile Ile Leu Arg Gly Gly
1               5

<210> SEQ ID NO 47
<211> LENGTH: 5
<212> TYPE: PRT
<213> ORGANISM: Escherichia coli

<400> SEQUENCE: 47

Ser His Ala Asn Ser
1               5

<210> SEQ ID NO 48
<211> LENGTH: 8
<212> TYPE: PRT
<213> ORGANISM: Pseudomonas aeruginosa

<400> SEQUENCE: 48

Gly Leu Leu Leu Gly Gln Leu Leu
1               5

<210> SEQ ID NO 49
<211> LENGTH: 5
<212> TYPE: PRT
<213> ORGANISM: Pseudomonas aeruginosa

<400> SEQUENCE: 49

Arg Ile Arg Ala Gly
1               5

<210> SEQ ID NO 50
<211> LENGTH: 10
<212> TYPE: PRT
<213> ORGANISM: Pseudomonas aeruginosa

<400> SEQUENCE: 50

Val Thr Val Tyr Gly Gln Thr Glu Val Thr
1               5               10

<210> SEQ ID NO 51
```

```
<211> LENGTH: 6
<212> TYPE: PRT
<213> ORGANISM: Pseudomonas aeruginosa

<400> SEQUENCE: 51

Ile Ala Gly Cys Asp Gly
1               5

<210> SEQ ID NO 52
<211> LENGTH: 8
<212> TYPE: PRT
<213> ORGANISM: Pseudomonas aeruginosa

<400> SEQUENCE: 52

Val Tyr Pro Phe Gly Trp Leu Gly
1               5

<210> SEQ ID NO 53
<211> LENGTH: 7
<212> TYPE: PRT
<213> ORGANISM: Pseudomonas aeruginosa

<400> SEQUENCE: 53

Arg Gly Phe Ala Leu Cys Ser
1               5

<210> SEQ ID NO 54
<211> LENGTH: 6
<212> TYPE: PRT
<213> ORGANISM: Pseudomonas aeruginosa

<400> SEQUENCE: 54

Thr Arg Ser Arg Tyr Tyr
1               5

<210> SEQ ID NO 55
<211> LENGTH: 8
<212> TYPE: PRT
<213> ORGANISM: Pseudomonas aeruginosa

<400> SEQUENCE: 55

Glu Lys Leu Val Thr Gly Pro Ser
1               5

<210> SEQ ID NO 56
<211> LENGTH: 11
<212> TYPE: PRT
<213> ORGANISM: Pseudomonas aeruginosa

<400> SEQUENCE: 56

Glu Lys Ser Ile Ala Pro Leu Arg Ser Phe Val
1               5                   10

<210> SEQ ID NO 57
<211> LENGTH: 16
<212> TYPE: PRT
<213> ORGANISM: Pseudomonas aeruginosa

<400> SEQUENCE: 57

Glu Lys Ser Ile Ala Pro Leu Arg Ser Phe Val Leu Ala Ala Ser Asp
1               5                   10                  15

<210> SEQ ID NO 58
<211> LENGTH: 11
<212> TYPE: PRT
```

<213> ORGANISM: Pseudomonas aeruginosa

<400> SEQUENCE: 58

Trp Lys Ala Glu Arg Phe Ser Trp Trp Met Thr
1               5                   10

<210> SEQ ID NO 59
<211> LENGTH: 10
<212> TYPE: PRT
<213> ORGANISM: Pseudomonas aeruginosa

<400> SEQUENCE: 59

Ala Glu Asn Tyr Val Gly Leu Pro Tyr Glu
1               5                   10

<210> SEQ ID NO 60
<211> LENGTH: 10
<212> TYPE: PRT
<213> ORGANISM: Pseudomonas aeruginosa

<400> SEQUENCE: 60

Ala Glu Asn Phe Val Gly Leu Pro Tyr Glu
1               5                   10

<210> SEQ ID NO 61
<211> LENGTH: 38
<212> TYPE: PRT
<213> ORGANISM: Escherichia coli

<400> SEQUENCE: 61

Met Pro Ile Glu Leu Leu Pro Glu Thr Pro Ser Gln Thr Ala Gly Pro
1               5                   10                  15

Tyr Val His Ile Gly Leu Ala Leu Glu Ala Ala Gly Asn Pro Thr Arg
            20                  25                  30

Asp Gln Glu Ile Trp Asn
        35

<210> SEQ ID NO 62
<211> LENGTH: 13
<212> TYPE: PRT
<213> ORGANISM: Escherichia coli

<400> SEQUENCE: 62

Val Tyr Asp Gly Asn Gly His Leu Val Arg Asp Ser Phe
1               5                   10

<210> SEQ ID NO 63
<211> LENGTH: 7
<212> TYPE: PRT
<213> ORGANISM: Escherichia coli

<400> SEQUENCE: 63

Trp Gln Ala Asp Ala Asn Gly
1               5

<210> SEQ ID NO 64
<211> LENGTH: 17
<212> TYPE: PRT
<213> ORGANISM: Escherichia coli

<400> SEQUENCE: 64

Phe Asn Ser Phe Gly Arg Thr Ala Thr Thr Phe Asp Ala Gly Glu Trp
1               5                   10                  15

-continued

Thr

```
<210> SEQ ID NO 65
<211> LENGTH: 7
<212> TYPE: PRT
<213> ORGANISM: Escherichia coli

<400> SEQUENCE: 65

Thr Val Lys Pro Gly Val Val
1               5

<210> SEQ ID NO 66
<211> LENGTH: 34
<212> TYPE: PRT
<213> ORGANISM: Escherichia coli

<400> SEQUENCE: 66

Asn Ala Ala Gly Val Pro Met Ala Pro His Ile Asn Ile Ser Leu Phe
1               5                   10                  15

Ala Arg Gly Ile Asn Ile His Leu His Thr Arg Leu Tyr Phe Asp Asp
            20                  25                  30

Glu Ala

<210> SEQ ID NO 67
<211> LENGTH: 20
<212> TYPE: PRT
<213> ORGANISM: Escherichia coli

<400> SEQUENCE: 67

Ala Asn Ala Lys Cys Pro Val Leu Asn Leu Ile Glu Gln Pro Gln Arg
1               5                   10                  15

Arg Glu Thr Leu
            20

<210> SEQ ID NO 68
<211> LENGTH: 29
<212> TYPE: PRT
<213> ORGANISM: Escherichia coli

<400> SEQUENCE: 68

Ala Lys Arg Cys Glu Val Asp Gly Lys Thr Ala Tyr Arg Phe Asp Ile
1               5                   10                  15

Arg Ile Gln Gly Glu Gly Glu Thr Val Phe Phe Asp Phe
            20                  25

<210> SEQ ID NO 69
<211> LENGTH: 28
<212> TYPE: PRT
<213> ORGANISM: Escherichia coli

<400> SEQUENCE: 69

Met Pro Ala Gln Asp Asn Ser Arg Phe Val Ile Arg Asp Arg Asn Trp
1               5                   10                  15

His Pro Lys Ala Leu Thr Pro Asp Tyr Lys Thr Ser
            20                  25

<210> SEQ ID NO 70
<211> LENGTH: 21
<212> TYPE: PRT
<213> ORGANISM: Escherichia coli

<400> SEQUENCE: 70
```

-continued

```
Ala Arg Ser Pro Arg Gln Ala Leu Val Ser Ile Pro Gln Ser Ile Ser
1               5                   10                  15

Glu Thr Thr Gly Pro
            20

<210> SEQ ID NO 71
<211> LENGTH: 21
<212> TYPE: PRT
<213> ORGANISM: Escherichia coli

<400> SEQUENCE: 71

His Leu Gly Phe Gly Ala His Asp His Asp Leu Leu Leu Asn Phe Asn
1               5                   10                  15

Asn Gly Gly Leu Pro
            20

<210> SEQ ID NO 72
<211> LENGTH: 15
<212> TYPE: PRT
<213> ORGANISM: Escherichia coli

<400> SEQUENCE: 72

Gly Glu Arg Ile Ile Val Ala Gly Arg Val Val Asp Gln Tyr Gly
1               5                   10                  15

<210> SEQ ID NO 73
<211> LENGTH: 8
<212> TYPE: PRT
<213> ORGANISM: Escherichia coli

<400> SEQUENCE: 73

Pro Val Pro Asn Thr Leu Val Glu
1               5

<210> SEQ ID NO 74
<211> LENGTH: 33
<212> TYPE: PRT
<213> ORGANISM: Escherichia coli

<400> SEQUENCE: 74

Trp Gln Ala Asn Ala Gly Gly Arg Tyr Arg His Lys Asn Asp Arg Tyr
1               5                   10                  15

Leu Ala Pro Leu Asp Pro Asn Phe Gly Gly Val Gly Arg Cys Leu Thr
            20                  25                  30

Asp

<210> SEQ ID NO 75
<211> LENGTH: 24
<212> TYPE: PRT
<213> ORGANISM: Escherichia coli

<400> SEQUENCE: 75

Phe Arg Thr Ile Lys Pro Gly Pro Tyr Pro Trp Arg Asn Gly Pro Asn
1               5                   10                  15

Asp Trp Arg Pro Ala His Ile His
            20

<210> SEQ ID NO 76
<211> LENGTH: 22
<212> TYPE: PRT
<213> ORGANISM: Escherichia coli

<400> SEQUENCE: 76
```

Ser Gly Pro Ser Ile Ala Thr Lys Leu Ile Thr Gln Leu Tyr Phe Glu
1               5                   10                  15

Gly Asp Pro Leu Ile Pro
            20

<210> SEQ ID NO 77
<211> LENGTH: 10
<212> TYPE: PRT
<213> ORGANISM: Escherichia coli

<400> SEQUENCE: 77

Cys Pro Ile Val Lys Ser Ile Ala Asn Pro
1               5                   10

<210> SEQ ID NO 78
<211> LENGTH: 26
<212> TYPE: PRT
<213> ORGANISM: Escherichia coli

<400> SEQUENCE: 78

Ala Val Gln Gln Leu Ile Ala Lys Leu Asp Met Ser Asn Ala Asn Pro
1               5                   10                  15

Met Asp Cys Leu Ala Tyr Arg Phe Asp Ile
            20                  25

<210> SEQ ID NO 79
<211> LENGTH: 10
<212> TYPE: PRT
<213> ORGANISM: Escherichia coli

<400> SEQUENCE: 79

Leu Arg Gly Gln Arg Lys Thr His Phe Glu
1               5                   10

<210> SEQ ID NO 80
<211> LENGTH: 52
<212> TYPE: DNA
<213> ORGANISM: Artificial Sequence
<220> FEATURE:
<223> OTHER INFORMATION: Forward primer for Part isolation of schl1-aroG

<400> SEQUENCE: 80
cgctaaggat gatttctgga attcggtctc taatggcttc tatgatatcc tc          52

<210> SEQ ID NO 81
<211> LENGTH: 50
<212> TYPE: DNA
<213> ORGANISM: Artificial sequence
<220> FEATURE:
<223> OTHER INFORMATION: Reverse Primer for Part isolation of schl1-aroG

<400> SEQUENCE: 81
cagctcgagt taggatccgg tctctaagct caaccccttc ttgccttaac              50

<210> SEQ ID NO 82
<211> LENGTH: 51
<212> TYPE: DNA
<213> ORGANISM: Artificial Sequence
<220> FEATURE:
<223> OTHER INFORMATION: Forward Primer for Part isolation of schl3-QsuB

<400> SEQUENCE: 82
cgctaaggat gatttctgga attcggtctc taatggcttc gatctcctcc t           51

-continued

```
<210> SEQ ID NO 83
<211> LENGTH: 56
<212> TYPE: DNA
<213> ORGANISM: Artificial Sequence
<220> FEATURE:
<223> OTHER INFORMATION: Reverse Primer for Part isolation of schl3-QsuB

<400> SEQUENCE: 83
cagctcgagt taggatccgg tctctaagct cagtttggga tacctctctc taaatc          56

<210> SEQ ID NO 84
<211> LENGTH: 61
<212> TYPE: DNA
<213> ORGANISM: Artificial Sequence
<220> FEATURE:
<223> OTHER INFORMATION: Forward primer for Part isolation of pAtRef8

<400> SEQUENCE: 84
cgctaaggat gatttctgga attcggtctc tggagtaaca cctatctcaa ttcatattga          60
a                                                                          61

<210> SEQ ID NO 85
<211> LENGTH: 54
<212> TYPE: DNA
<213> ORGANISM: Artificial Sequence
<220> FEATURE:
<223> OTHER INFORMATION: Reverse primer for Part isolation of pAtRef8

<400> SEQUENCE: 85
cagctcgagt taggatccgg tctcacatta gttttgcttc tatttttatt ttcg          54

<210> SEQ ID NO 86
<211> LENGTH: 21
<212> TYPE: DNA
<213> ORGANISM: Artificial Sequence
<220> FEATURE:
<223> OTHER INFORMATION: Forward primer for genotyping of AroG* from
      pAroG and lines AroG* x QsuB

<400> SEQUENCE: 86
agaagttgga agctcaagca a                                                21

<210> SEQ ID NO 87
<211> LENGTH: 24
<212> TYPE: DNA
<213> ORGANISM: Artificial Sequence
<220> FEATURE:
<223> OTHER INFORMATION: Reverse primer for genotyping of AroG* from
      pAroG and lines AroG* x QsuB

<400> SEQUENCE: 87
cccatctcat aaataacgtc atgc                                             24

<210> SEQ ID NO 88
<211> LENGTH: 21
<212> TYPE: DNA
<213> ORGANISM: Artificial Sequence
<220> FEATURE:
<223> OTHER INFORMATION: Forward primer for Genotyping of QsuB from
      lines AroG* x QsuB

<400> SEQUENCE: 88
cgctacagga aggttaggtg a                                                21

<210> SEQ ID NO 89
```

```
<211> LENGTH: 22
<212> TYPE: DNA
<213> ORGANISM: Artificial Sequence
<220> FEATURE:
<223> OTHER INFORMATION: Reverse primer for Genotyping of QsuB from
      lines AroG* x QsuB

<400> SEQUENCE: 89
cacagttcga tagcgaaaac cg                                                     22

<210> SEQ ID NO 90
<211> LENGTH: 21
<212> TYPE: DNA
<213> ORGANISM: Artificial Sequence
<220> FEATURE:
<223> OTHER INFORMATION: Forward primer for genotyping of AroG* in
      pPDC-4G and lines PDC-4G x QsuB

<400> SEQUENCE: 90
agaagttgga agctcaagca a                                                      21

<210> SEQ ID NO 91
<211> LENGTH: 21
<212> TYPE: DNA
<213> ORGANISM: Artificial Sequence
<220> FEATURE:
<223> OTHER INFORMATION: Reverse primer for Genotyping of AroG* in
      pPDC-4G and lines PDC-4G x QsuB

<400> SEQUENCE: 91
cgtagatgaa agactgagtg c                                                      21

<210> SEQ ID NO 92
<211> LENGTH: 20
<212> TYPE: DNA
<213> ORGANISM: Artificial Sequence
<220> FEATURE:
<223> OTHER INFORMATION: Forward primer for Genotyping of PmdA in
      pPDC-4G and lines PDC-4G x QsuB

<400> SEQUENCE: 92
agcgcataac cgagaaaacc                                                        20

<210> SEQ ID NO 93
<211> LENGTH: 22
<212> TYPE: DNA
<213> ORGANISM: Artificial Sequence
<220> FEATURE:
<223> OTHER INFORMATION: Forward primer for Genotyping of PmdB in
      pPDC-4G and lines PDC-4G x QsuB

<400> SEQUENCE: 93
ctccaccaac tttcccctac tt                                                     22

<210> SEQ ID NO 94
<211> LENGTH: 22
<212> TYPE: DNA
<213> ORGANISM: Artificial Sequence
<220> FEATURE:
<223> OTHER INFORMATION: Reverse primer for Genotyping of PmdB in
      pPDC-4G and lines PDC-4G x QsuB

<400> SEQUENCE: 94
cacagttcga tagcgaaaac cg                                                     22

<210> SEQ ID NO 95
<211> LENGTH: 20
```

-continued

```
<212> TYPE: DNA
<213> ORGANISM: Artificial Sequence
<220> FEATURE:
<223> OTHER INFORMATION: Forward primer for Genotyping of PmdC in
      pPDC-4G and lines PDC-4G x QsuB

<400> SEQUENCE: 95
ggaaaccgcg acgatgaaag                                        20

<210> SEQ ID NO 96
<211> LENGTH: 24
<212> TYPE: DNA
<213> ORGANISM: Artificial Sequence
<220> FEATURE:
<223> OTHER INFORMATION: Reverse primer for genotyping of PmdC in
      pPDC-4G and lines PDC-4G x QsuB

<400> SEQUENCE: 96
cccatctcat aaataacgtc atgc                                   24

<210> SEQ ID NO 97
<211> LENGTH: 21
<212> TYPE: DNA
<213> ORGANISM: Artificial sequence
<220> FEATURE:
<223> OTHER INFORMATION: Forward primer for Genotyping of AroG* in
      pPDC-5G and lines PDC-5G

<400> SEQUENCE: 97
agaagttgga agctcaagca a                                      21

<210> SEQ ID NO 98
<211> LENGTH: 21
<212> TYPE: DNA
<213> ORGANISM: Artificial sequence
<220> FEATURE:
<223> OTHER INFORMATION: Reverse primer for Genotyping of AroG* in
      pPDC-5G and lines PDC-5G

<400> SEQUENCE: 98
cgtagatgaa agactgagtg c                                      21

<210> SEQ ID NO 99
<211> LENGTH: 21
<212> TYPE: DNA
<213> ORGANISM: Artificial sequence
<220> FEATURE:
<223> OTHER INFORMATION: Forward primer for Genotyping of QsuB in
      pPDC-5G and lines PDC-5G

<400> SEQUENCE: 99
cgctacagga aggttaggtg a                                      21

<210> SEQ ID NO 100
<211> LENGTH: 21
<212> TYPE: DNA
<213> ORGANISM: Artificial sequence
<220> FEATURE:
<223> OTHER INFORMATION: Reverse primer for Genotyping of QsuB in
      pPDC-5G and lines PDC-5G

<400> SEQUENCE: 100
agacagataa agccacgcac a                                      21

<210> SEQ ID NO 101
<211> LENGTH: 20
<212> TYPE: DNA
```

-continued

```
<213> ORGANISM: Artificial sequence
<220> FEATURE:
<223> OTHER INFORMATION: Forward primer for Genotyping of PmdA in
      pPDC-5G and lines PDC-5G

<400> SEQUENCE: 101
agcgcataac cgagaaaacc                                              20

<210> SEQ ID NO 102
<211> LENGTH: 22
<212> TYPE: DNA
<213> ORGANISM: Artificial sequence
<220> FEATURE:
<223> OTHER INFORMATION: Reverse primer for Genotyping of PmdA in
      pPDC-5G and lines PDC-5G

<400> SEQUENCE: 102
cacagttcga tagcgaaaac cg                                           22

<210> SEQ ID NO 103
<211> LENGTH: 22
<212> TYPE: DNA
<213> ORGANISM: Artificial sequence
<220> FEATURE:
<223> OTHER INFORMATION: Forward primer for Genotyping of PmdB in
      pPDC-5G and lines PDC-5G

<400> SEQUENCE: 103
ctccaccaac tttcccctac tt                                           22

<210> SEQ ID NO 104
<211> LENGTH: 24
<212> TYPE: DNA
<213> ORGANISM: Artificial sequence
<220> FEATURE:
<223> OTHER INFORMATION: Reverse primer for Genotyping of PmdB in
      pPDC-5G and lines PDC-5G

<400> SEQUENCE: 104
gggaacaaaa ggaataaaga ggca                                         24

<210> SEQ ID NO 105
<211> LENGTH: 20
<212> TYPE: DNA
<213> ORGANISM: Artificial sequence
<220> FEATURE:
<223> OTHER INFORMATION: Forward primer for Genotyping of PmdC in
      pPDC-5G and lines PDC-5G

<400> SEQUENCE: 105
ggaaaccgcg acgatgaaag                                             20

<210> SEQ ID NO 106
<211> LENGTH: 24
<212> TYPE: DNA
<213> ORGANISM: Artificial sequence
<220> FEATURE:
<223> OTHER INFORMATION: Reverse primer for Genotyping of PmdC in
      pPDC-5G and lines PDC-5G

<400> SEQUENCE: 106
cccatctcat aaataacgtc atgc                                         24
```

PLANTS AND METHODS FOR PRODUCING 2-PYRONE-4, 6-DICARBOXYLIC ACID (PDC)

CROSS-REFERENCE TO RELATED APPLICATIONS

This application claims priority to U.S. Provisional Patent Application Ser. No. 63/091,820, filed on Oct. 14, 2020, which is hereby incorporated by reference.

STATEMENT OF GOVERNMENTAL SUPPORT

This invention was made with government support under Contract No. DE-AC02-05CH11231 awarded by the United States Department of Energy. The government has certain rights in the invention.

FIELD OF THE INVENTION

This invention relates generally to producing 2-pyrone-4,6-dicarboxylic acid (PDC).

BACKGROUND OF THE INVENTION

2-Pyrone-4,6-dicarboxylic acid (PDC) is a promising building block chemical that can serve as a starting monomer for the manufacturing of performance-advantaged polymers (Shikinaka et al., 2018). For example, various PDC-based polyesters feature strong adhesive properties (Hishida et al., 2009), high rigidity and elasticity (Michinobu et al., 2008; Michinobu et al., 2010), and enhanced biodegradability (Bito et al., 2008; Michinobu et al., 2009). Recently, PDC was used for the synthesis of microspheres that potentially find useful applications in agriculture, biomedicine, and tribology (Johnson et al., 2019). Moreover, PDC also represents a valuable functional monomer with possible uses as disinfection chemical and decontaminating agent (Bito et al., 2008; Shikinaka et al., 2016).

To date, only bio-based routes for the synthesis of PDC have been reported, whereas chemical synthesis of PDC remains to be demonstrated. Engineered microbial hosts for the production of PDC include *Escherichia coli* (Nakajima et al., 2009; Luo et al., 2018; Kang et al., 2020), *Pseudomonas putida* (Otsuka et al., 2006; Qian et al., 2016; Johnson et al., 2019), and *Novosphingobium aromaticivorans* (Perez et al., 2019). Notably, the engineered *E. coli* and *P. putida* strains contain genes from *Sphingobium* sp. SYK-6 or *Comamonas testosterone* encoding protocatechuate 4,5-dioxygenase and 4-carboxy-2-hydroxymuconate-6-semialdehyde (CHMS) dehydrogenase to enable the conversion of protocatechuate (PCA) into PDC. In this pathway, CHMS produced from PCA by PCA 4,5-dioxygenase—an enzyme that comprises two subunits—is non-enzymatically converted to its intramolecular hemiacetal form prior conversion into PDC by CHMS dehydrogenase (FIG. 1). To the best of our knowledge, the use of plants as a platform for PDC production has never been reported.

Leveraging metabolic engineering approaches based on genetic engineering appears indispensable for the design of bioenergy crops towards developing sustainable biorefineries and enabling our future bioeconomy (Amore et al., 2016; Baral et al., 2019). With the advancement of biotechnological tools in both synthetic biology and plant transformation capabilities, the implementation of complex metabolic pathways in crops has become feasible (Altpeter et al., 2016; Shih et al., 2016). In particular, several desired traits for lignocellulosic bioenergy crops include higher yield, stress resilience, low biomass recalcitrance, and supply of value-added co-products (Eudes et al., 2014; Loqué et al., 2015; Bailey-Serres et al., 2019; Markel et al., 2020). Since plants are autotrophs able to capture solar energy, they represent attractive hosts for implementing de-novo metabolic pathways for cost-effective production of important chemicals in green tissues (Yuan and Grotewold, 2015). In support of these concepts, a recent techno-economic analysis indicated that in-planta production of chemicals in bioenergy crops can improve the economics of second-generation biofuel (Yang et al., 2020). Such renewable bioproducts made in plants include novel polymers (Börnke and Broer, 2010; Snell et al., 2015), platform chemicals (Eudes et al., 2018), pharmaceuticals, flavors and fragrances (Lin and Eudes, 2020), and triacylglycerols (Vanhercke et al., 2019).

Although the occurrence of PDC has been described within the Rosaceae family, no PDC biosynthetic genes have been characterized in plants (Wilkes and Glasl, 2001).

SUMMARY OF THE INVENTION

The present invention provides a genetically modified plant or plant cell comprising a nucleic acid encoding one or more heterologous enzymes operably linked a promoter, wherein one or more heterologous enzymes synthesizes 2-pyrone-4,6-dicarboxylic acid (PDC). The genetically modified host cell can comprise one of the enzymatic pathways necessary for producing a PDC described herein.

The present invention provides a genetically modified plant or plant cell comprising one or more nucleic acids encoding protocatechuate 4,5-dioxygenase (PmdAB), or homologous enzyme thereof, and/or 4-carboxy-2-hydroxy-muconate-6-semialdehyde dehydrogenase (PmdC), or homologous enzyme thereof, or operably linked to one or more promoters, wherein the genetically modified plant or plant cell is capable of producing protocatechuate (PCA) and produces 2-pyrone-4,6-dicarboxylic acid (PDC).

In some embodiments, the genetically modified plant or plant cell further comprises one or more nucleic acids encoding 3-deoxy-D-arabinoheptulosonate 7-phosphate synthase (AroG), or feedback-resistant DAHP synthase (AroG*), or homologous enzyme thereof, and 3-dehydro-shikimate dehydratase (QsuB), or homologous enzyme thereof, wherein the genetically modified plant or plant cell is capable of producing erythrose 4-phosphate (E4P) and phosphoenolpyruvate (PEP).

The present invention provides a genetically modified plant or plant cell comprising one or more nucleic acids encoding one or more of the following enzymes: 3-deoxy-D-arabinoheptulosonate 7-phosphate synthase (AroG), or feedback-resistant DAHP synthase (AroG*), chorismate pyruvate-lyase (UbiC), 3-dehydroshikimate dehydratase (QsuB), p-hydroxybenzoate 3-monooxygenase (PobA), or PobA* (such as a Y385F/1294A PobA mutant), protocatechuate 4,5-dioxygenase (PmdAB), 4-carboxy-2-hydroxy-muconate-6-semialdehyde dehydrogenase (PmdC), protocatechuate 3,4-dioxygenase (PcaGH), and 2-pyrone-4,6-dicarboxylate hydrolase (LigI), or any homologous enzyme of any of the enzymes thereof, operably linked to one or more promoters, wherein the genetically modified plant or plant cell is capable of producing chorismate (CHA) and produces 2-pyrone-4,6-dicarboxylic acid (PDC).

In some embodiments, the genetically modified plant or plant cell comprising one or more nucleic acids encoding one or more of the following enzymes: chorismate pyruvate-lyase (UbiC), p-hydroxybenzoate 3-monooxygenase (PobA), or PobA*, protocatechuate 4,5-dioxygenase (PmdAB), 4-carboxy-2-hydroxymuconate-6-semialdehyde dehydrogenase (PmdC), PcaGH, and LigI, or any homologous enzyme of any of the enzymes thereof, operably linked to one or more promoters.

In some embodiments, the genetically modified plant or plant cell comprising one or more nucleic acids encoding one or more of the following enzymes: 3-deoxy-D-arabinoheptulosonate 7-phosphate synthase (AroG), or feedback-resistant DAHP synthase (AroG*), chorismate pyruvate-lyase (UbiC), p-hydroxybenzoate 3-monooxygenase (PobA), or PobA*, protocatechuate 4,5-dioxygenase (PmdAB), PcaGH, and LigI, or any homologous enzyme of any of the enzymes thereof, operably linked to one or more promoters.

In some embodiments, the genetically modified plant or plant cell comprising one or more nucleic acids encoding one or more of the following enzymes: chorismate pyruvate-lyase (UbiC), PobA*, protocatechuate 4,5-dioxygenase (PmdAB), and LigI, or any homologous enzyme of any of the enzymes thereof, operably linked to one or more promoters. In some embodiments, the feedback-resistant DAHP synthase (L175Q) (AroG*) is bacterial or *E. coli* DAHP synthase (AroG) that has a L175Q mutation which causes the AroG to be feedback resistant.

In some embodiments, the genetically modified plant or plant cell comprising one or more nucleic acids encoding one or more of the following enzymes: chorismate pyruvate-lyase (UbiC), PobA*, and PcaGH, or any homologous enzyme of any of the enzymes thereof, operably linked to one or more promoters.

In some embodiments, the genetically modified plant or plant cell comprising one or more nucleic acids encoding one or more of the following enzymes: chorismate pyruvate-lyase (UbiC), p-hydroxybenzoate 3-monooxygenase (PobA), protocatechuate 4,5-dioxygenase (PmdAB), and 4-carboxy-2-hydroxymuconate-6-semialdehyde dehydrogenase (PmdC), or any homologous enzyme of any of the enzymes thereof, operably linked to one or more promoters.

In some embodiments, the genetically modified plant or plant cell further comprises a nucleic acid encoding 3-deoxy-D-arabinoheptulosonate 7-phosphate synthase (AroG), or feedback-resistant DAHP synthase (AroG*) operably linked to a promoter. In some embodiments, the genetically modified plant or plant cell further comprises a nucleic acid encoding 3-dehydroshikimate dehydratase (QsuB) operably linked to a promoter.

In some embodiments, the genetically modified plant or plant cell comprises one or more nucleic acids encoding protocatechuate 4,5-dioxygenase (PmdAB), or a homologous enzyme thereof, and/or 4-carboxy-2-hydroxymuconate-6-semialdehyde dehydrogenase (PmdC), or a homologous enzyme thereof, or operably linked to one or more promoters, wherein the genetically modified plant or plant cell is capable of producing protocatechuate (PCA) and produces 2-pyrone-4,6-dicarboxylic acid (PDC).

In some embodiments, the genetically modified plant or plant cell comprises a nucleic acid encoding 3-dehydroshikimate dehydratase (QsuB), or a homologous enzyme thereof.

In some embodiments, the genetically modified plant or plant cell comprises a nucleic acid encoding feedback-resistant DAHP synthase (AroG*), or a homologous enzyme thereof.

In some embodiments, the genetically modified plant or plant cell comprises a nucleic acid encoding p-hydroxybenzoate 3-monooxygenase (PobA), or PobA*, or a homologous enzyme thereof, and chorismate pyruvate-lyase (UbiC), or a homologous enzyme thereof.

In some embodiments, the genetically modified plant or plant cell comprises one or more nucleic acids encoding 3-deoxy-D-arabinoheptulosonate 7-phosphate synthase (AroG), or feedback-resistant DAHP synthase (AroG*), or a homologous enzyme thereof, and 3-dehydroshikimate dehydratase (QsuB), or a homologous enzyme thereof, wherein the genetically modified plant or plant cell is capable of producing erythrose 4-phosphate (E4P) and phosphoenolpyruvate (PEP).

In some embodiments, the genetically modified plant or plant cell comprises one or more nucleic acids encoding PobA*, or a homologous enzyme thereof, chorismate pyruvate-lyase (UbiC), or a homologous enzyme thereof, feedback-resistant DAHP synthase (AroG*), or a homologous enzyme thereof, protocatechuate 3,4-dioxygenase subunit alpha (PcaG), or a homologous enzyme thereof, and protocatechuate 3,4-dioxygenase subunit beta (PcaH), or a homologous enzyme thereof, wherein the genetically modified plant or plant cell synthesizes 2-pyrone-4,6-dicarboxylic acid (PDC).

2-pyrone-4-6-dicarboxylic acid (PDC) is a pseudoaromatic dicarboxylic acid and is a promising biobased building block chemical that can be used to make diverse polyesters with novel functionalities. There are currently no reports on the chemical synthesis of PDC. In some embodiments, the biological synthesis of PDC in a plant or plant cell is mediated by heterologous expression of bacterial genes. Using plants (or any other photosynthetic organisms) for PDC production presents an advantage over other hosts due to their capacity to use light as energy source.

In some embodiments, the PmdAB and/or PmdC are *Comamonas testosterone* PmdAB and/or PmdC. In some embodiments, the DAHP synthase (AroG) comprises one or more of the following amino acid residues acting as metal-binding sites: C at position 61, H at position 268, E at position 302, and/or D at position 326, and/or any conserved amino acid residues disclosed in Wu et al., *J. Biol. Chem.* 278(30):27525-27531 (2003). In some embodiments, the PcaGH are *Streptomyces* sp. 2065 PcaGH. In some embodiments, the PobA is a *Pseudomonas aeruginosa* PobA. In some embodiments, the PobA* is a *Pseudomonas aeruginosa* PobA Y385F/T294A PobA mutant.

In some embodiments, one or more, or all, of the enzymes are heterologous to another enzyme, or heterologous to the host cell. In some embodiments, each nucleic acid resides on a vector, such as a vector capable of stable residency in a plant or plant cell. In some embodiments, each nucleic acid is stably integrated in a chromosome of a plant or plant cell. In some embodiments, each promoter is capable of constitutive expression, or a tissue-specific or organelle-specific, such as plastid-specific, in the plant or plant cell.

The present invention provides for a method for producing a PDC comprising: (a) optionally genetically modifying a plant or plant cell to produce a genetically modified plant or plant cell of the present invention, (b) growing or culturing the genetically modified plant or plant cell to produce a PDC, and (c) optionally recovering the PDC produced from the plant or plant cell.

In some embodiments, the genetically modified plant or plant cell endogenously produces E4P and PEP, 3-dehydroshikimate, and/or CHA. In some embodiments, the genetically modified plant or plant cell further comprises one or more enzymes that in the pathway that converts PEP and/or E4P into 3-dehydroshikimate, and/or CHA.

In some embodiments, each enzyme is expressed in, or expressed and transport to, a plastid in the genetically modified plant or plant cell.

In some embodiments, the promoter is tissue-specific.

In some embodiments, synthetic genes encoding bacterial enzymes targeted to plastids are expressed in a plant to convert intermediates of the shikimate pathway (e.g., 3-de-hydroshikimate, chorismate) into PDC. This is a new method for PDC production. Other methods have used microbes such as *E. coli* for PDC production.

One or more parameters of the following are validated for the present invention: (1) Expression and stability of bacterial enzymes in plant plastids. (2) Occurrence in plastids of the spontaneous reaction that allows formation of the hemi-acetal form of CHMS (LigC substrate). (3) Stability and extractability of PDC once produced in plant tissues.

The present invention is useful for leading to cheaper manufacturing of PDC for use as a functional monomer (building block) for novel biopolymers and composites with improved properties. PDC can also be used to produce new biological antibacterial agents (such as for dairy products) or for decontamination of polluted water (such as radioactive cesium).

In some embodiments, the promoter is a plastid-specific promoter. In some embodiments, the promoter is a CER1, CER2, CER3, CER4, CER5, CER6, CER10, WSD1, Mah1, WBC11, KCS1, KCS2, FATB, LACS1, LACS2, CYP864A, CYP86A7, CYP86A5, KCS10, or KCS5 promoter. In some embodiments, the tissue-specific promoter are as described herein. In embodiments, the fiber-specific promoter is an NST, NST1, NST2, NST3, or LAC17 promoter. In some embodiments, the vessel-specific promoter is a VND1, VND2, VND3, VND4, VND5, VND6, VND7, VNI2, REF4, or RFR1 promoter. In some embodiments, the secondary cell wall-specific promoter is an IRX1, IRX3, IRX5, IRX8, IRX9, IRX14, IRX7, IRX10, GAUT13, GAUT14, or CESA4 promoter. Suitable tissue-specific secondary wall promoters, and other transcription factors, promoters, regulatory systems, and the like, suitable for this present invention are taught in U.S. Patent Application Pub. Nos. 2014/0298539, 2015/0051376, 2016/0017355, and 2016/0251672.

BRIEF DESCRIPTION OF THE DRAWINGS

The foregoing aspects and others will be readily appreciated by the skilled artisan from the following description of illustrative embodiments when read in conjunction with the accompanying drawings.

PmdA (c), PmdB (d), and PmdC (e) in six independent transformants containing the pPDC-5G construct. The pPDC-5G plasmid (PC) and gDNA obtained from Arabidopsis wildtype (WT) were used as controls.

Figure 6A:
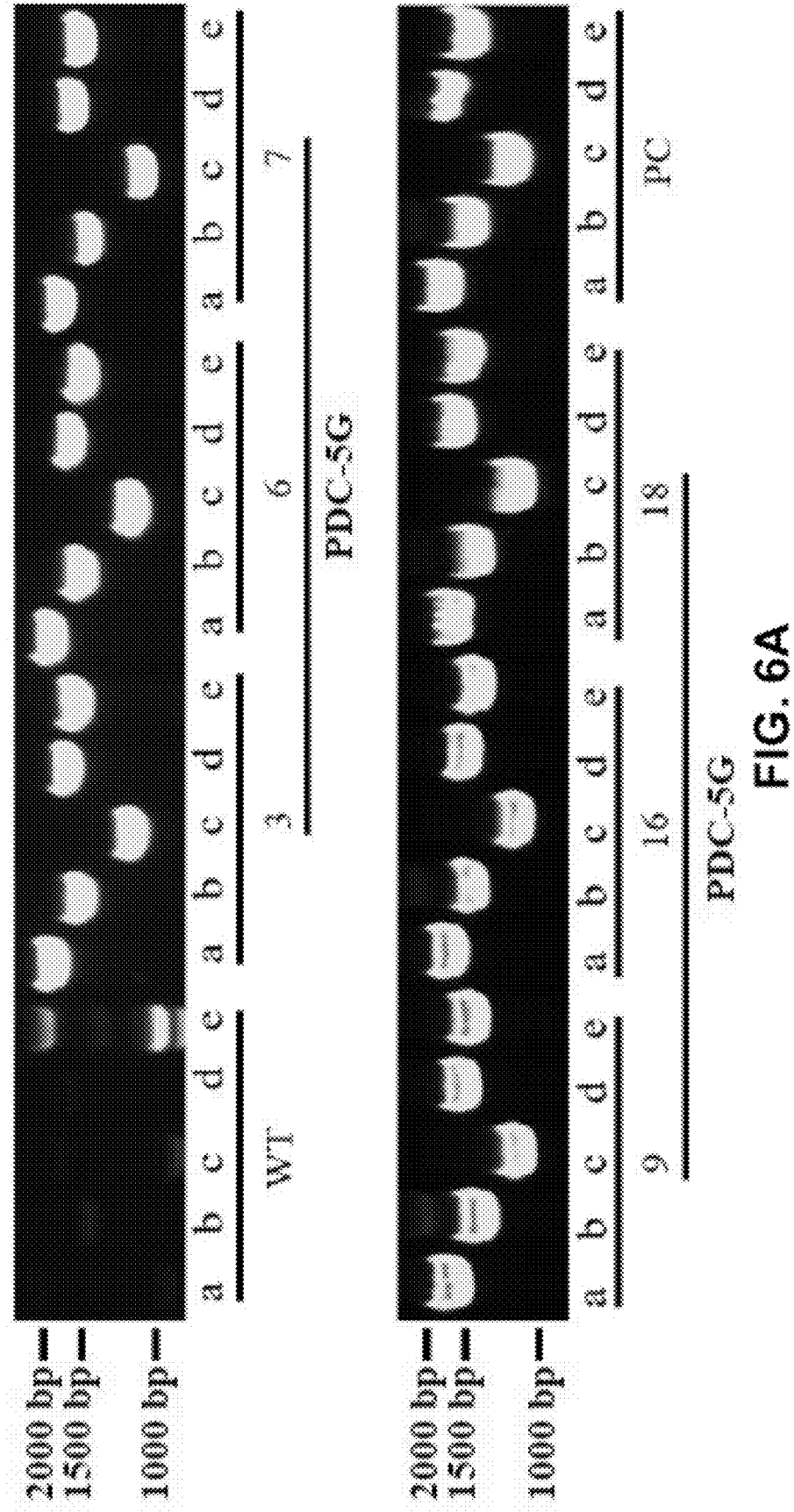
FIG. 6A. Production of PDC production in wildtype Arabidopsis. Detection by PCR of AroG* (a), QsuB (b)
Figure 6B:
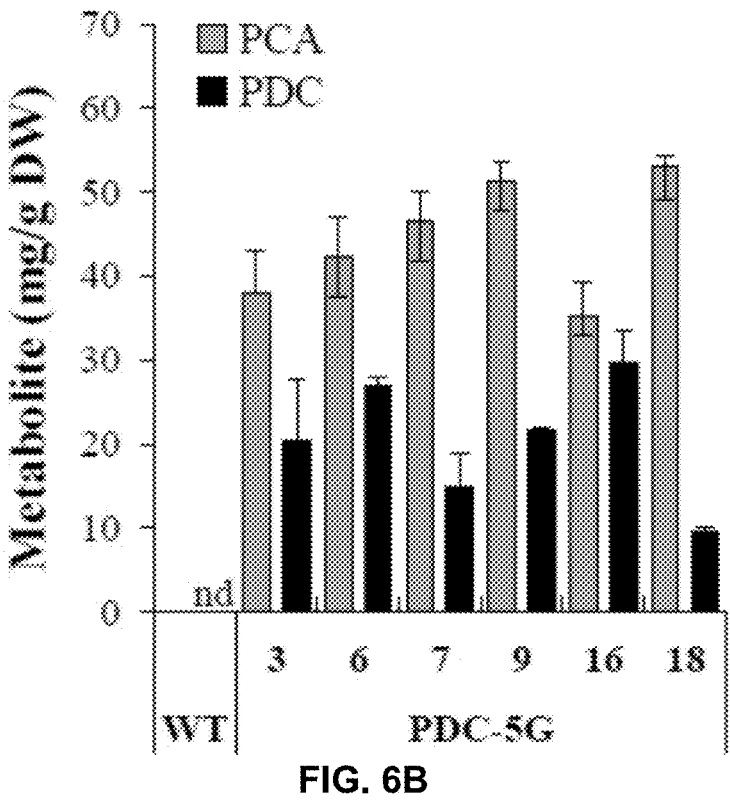

FIG. 6B. Production of PDC production in wildtype Arabidopsis. PCA and PDC titers in Arabidopsis wildtype (WT) and PDC-5G lines. Nd, not detected. Error bars represent the SE from four biological replicates (n=4). Asterisks indicate significant differences from the wild type using the unpaired Student's t-test (**P<0.01, *P<0.05).

Figure 6C:
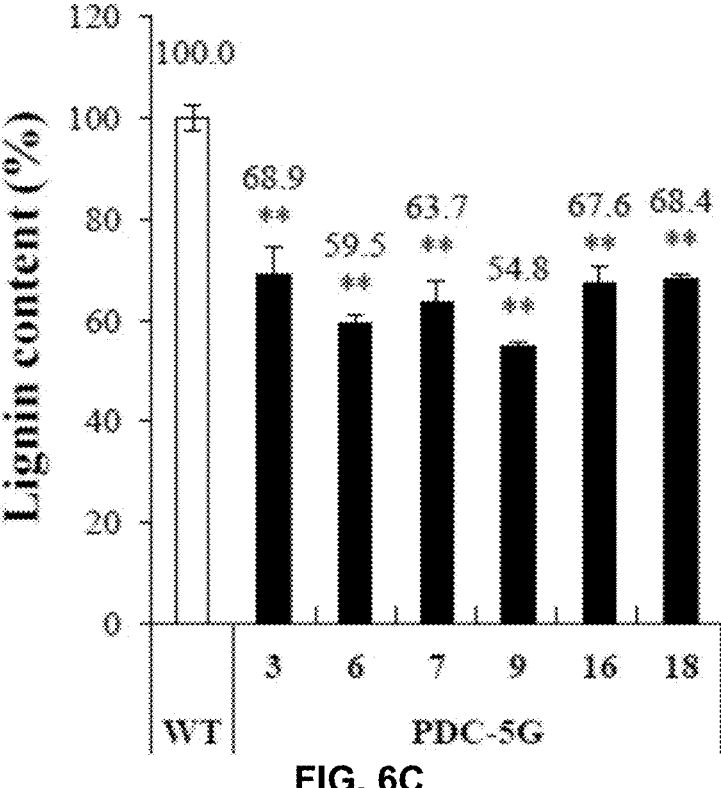

FIG. 6C. Production of PDC production in wildtype Arabidopsis. Lignin contents in Arabidopsis wildtype (WT) and PDC-5G lines. Nd, not detected. Error bars represent the SE from four biological replicates (n=4). Asterisks indicate significant differences from the wild type using the unpaired Student's t-test (**P<0.01, *P<0.05).

Figure 6D:
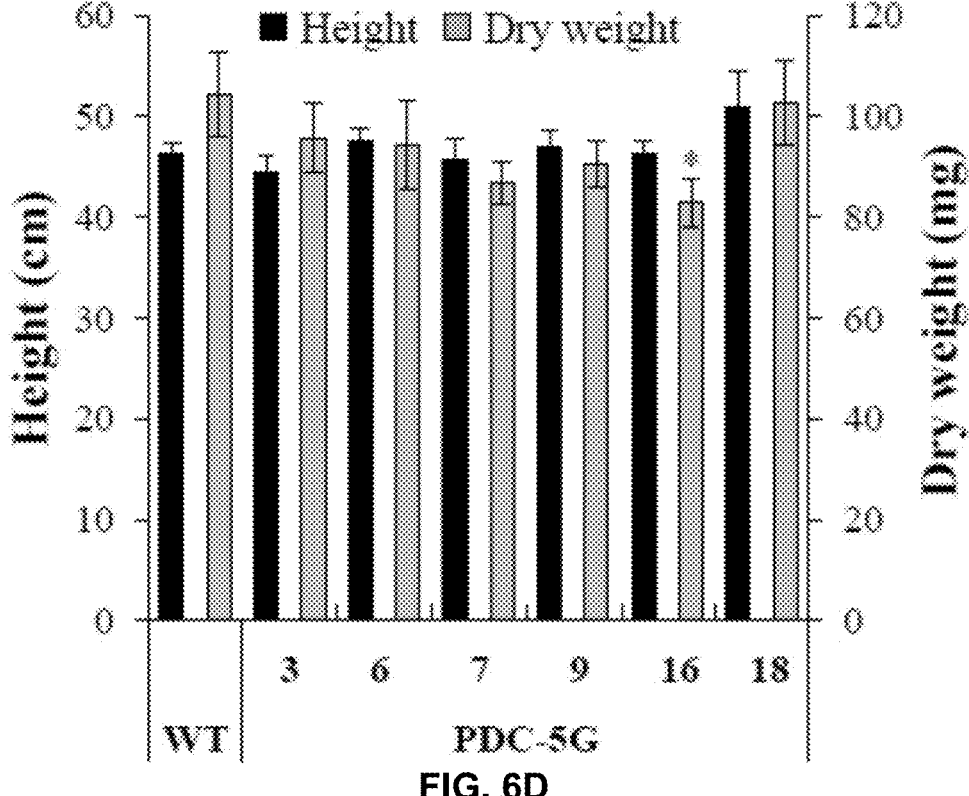

FIG. 6D. Production of PDC production in wildtype Arabidopsis. Growth parameters (height and dry weight) of wild-type (WT) and transgenic Arabidopsis lines. Error bars represent the SE from eight biological replicates (n=8). Asterisks indicate significant differences from the wild type using the unpaired Student's t-test (**P<0.01,*P<0.05).

Figure 7:
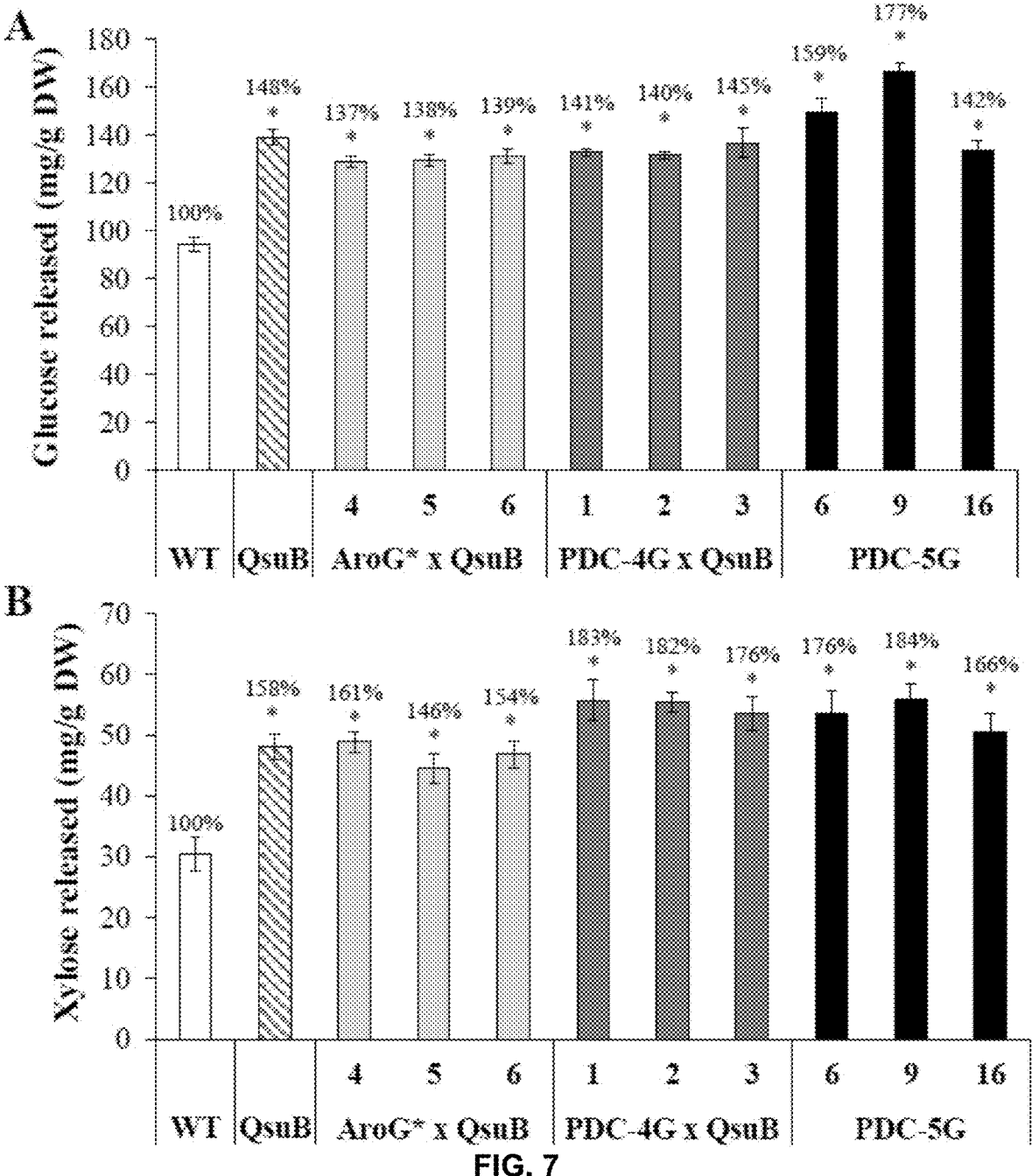

FIG. 7. Biomass saccharification of wild-type (WT) and representative transgenic lines. Amounts of (A) glucose and (B) xylose released from biomass after 96-h enzymatic digestion are shown. Values are means±SE of four biological replicates (n=4). Asterisks indicate significant differences from the wild type using the unpaired Student's t-test (*p<0.01).

Figure 8:
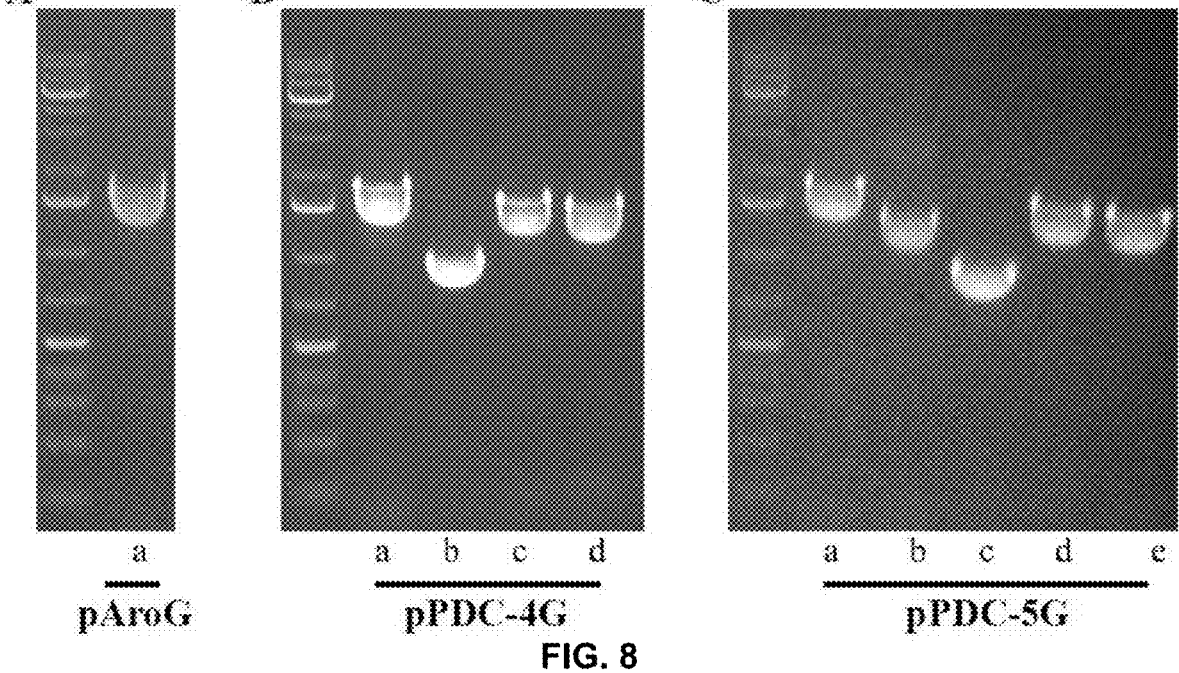

FIG. 8. Verification by PCR of the integrity of plasmids extracted from *Agrobacterium* strains used for Arabidopsis transformations using the primers listed in Table 1. Plasmids are pAroG (A), pPDC-4G (B), and pPDC-5G (C). Amplified DNA correspond to the genes AroG* (a), PmdA (b), PmdB (c), PmdC (d), and QsuB (e).

Figure 9:
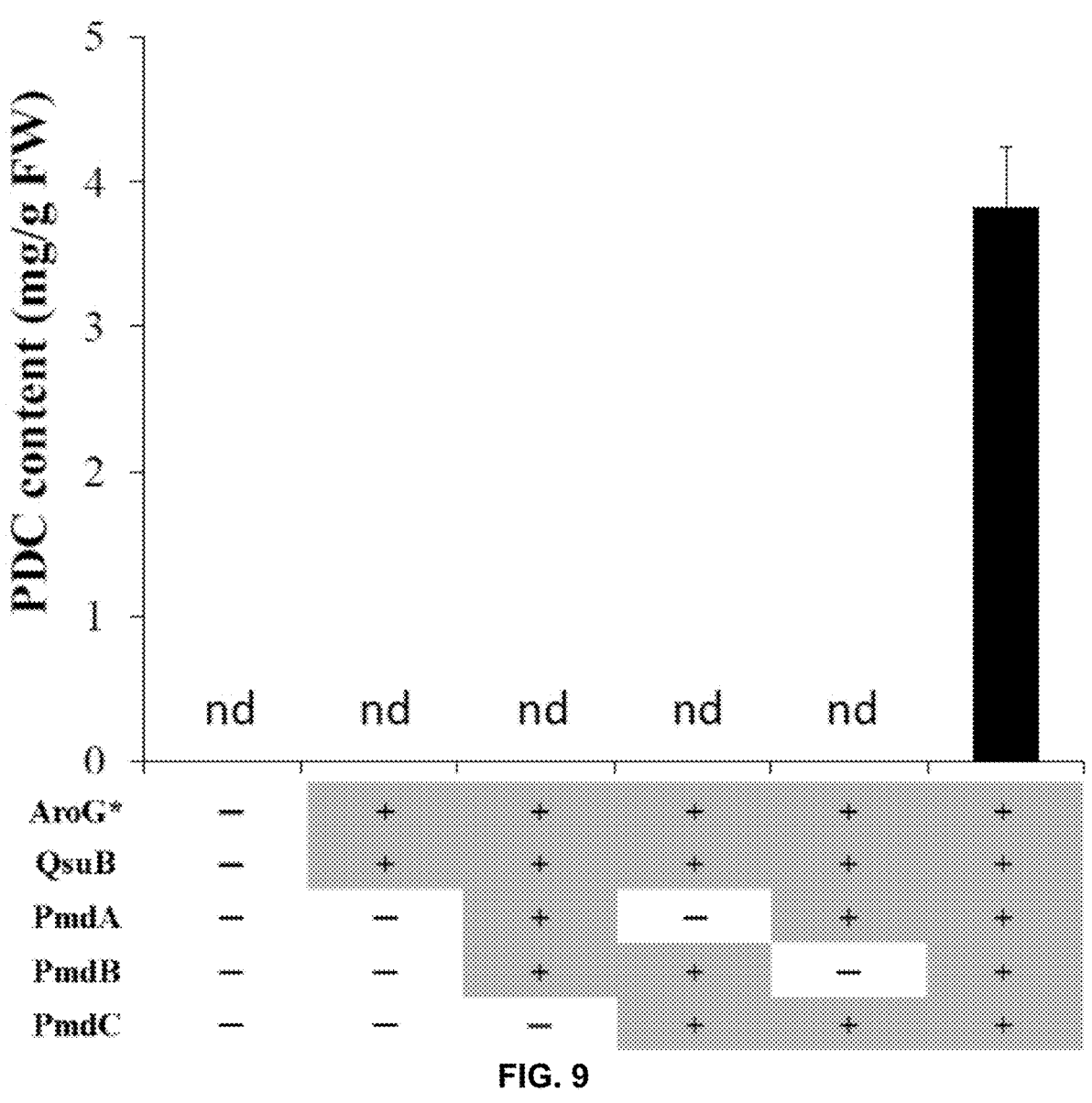

FIG. 9. Identification of the essential PDC biosynthetic enzymes in tobacco leaves by combinatorial transient expression of AroG* and QsuB with PmdA, PmdB, and PmdC. Error bars represent the SE from three biological replicates (n=3). nd, not detected.

Figure 10:
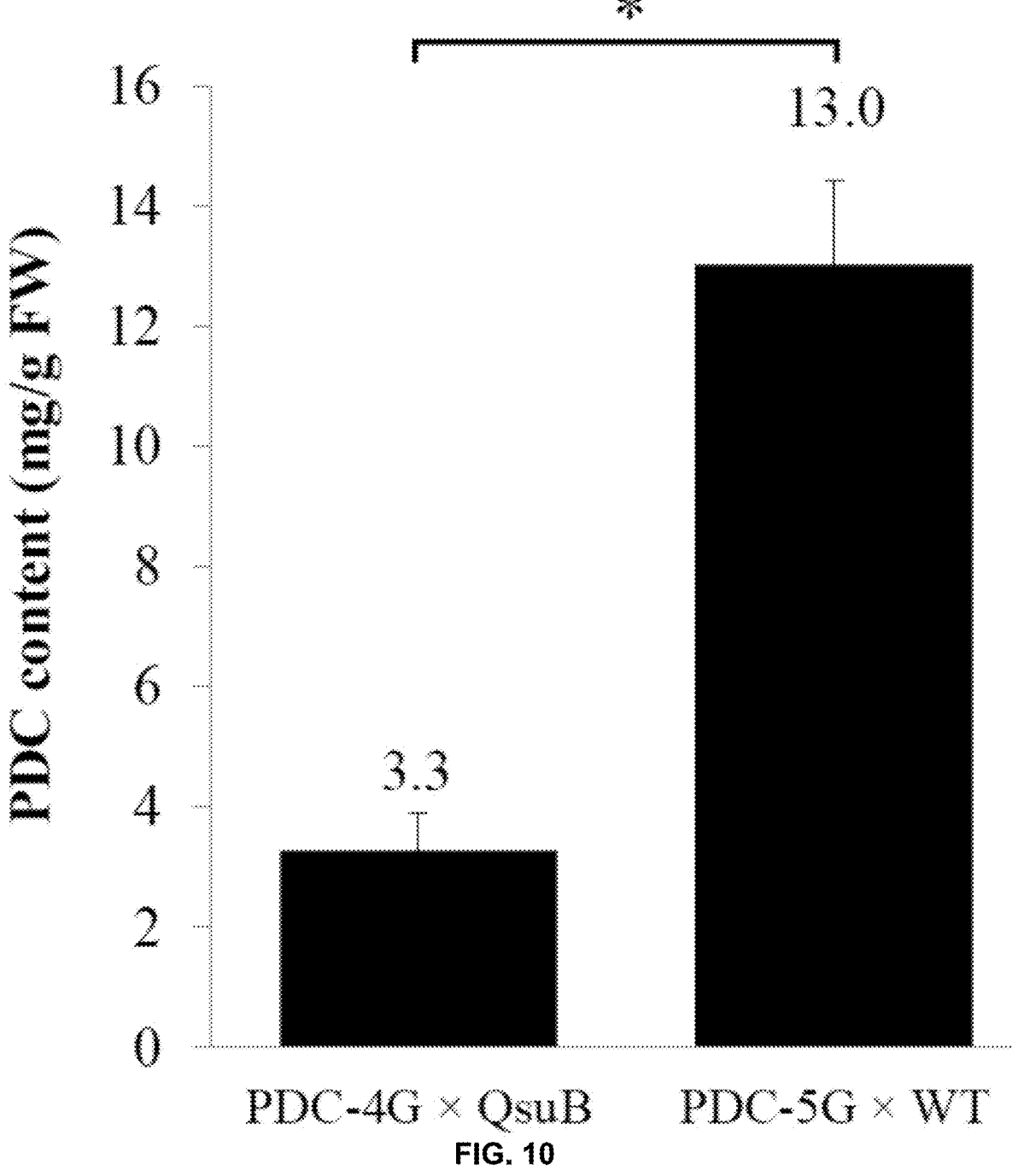

FIG. 10. Average PDC titers from Arabidopsis PDC-4G× QsuB and PDC-5G transgenic lines at the T1 generation (primary transformants). Error bars represent the SE from twelve and thirteen independent lines, respectively. Asterisks indicate a significant difference using the unpaired Student's t-test (*P<0.01).

Figure 11:
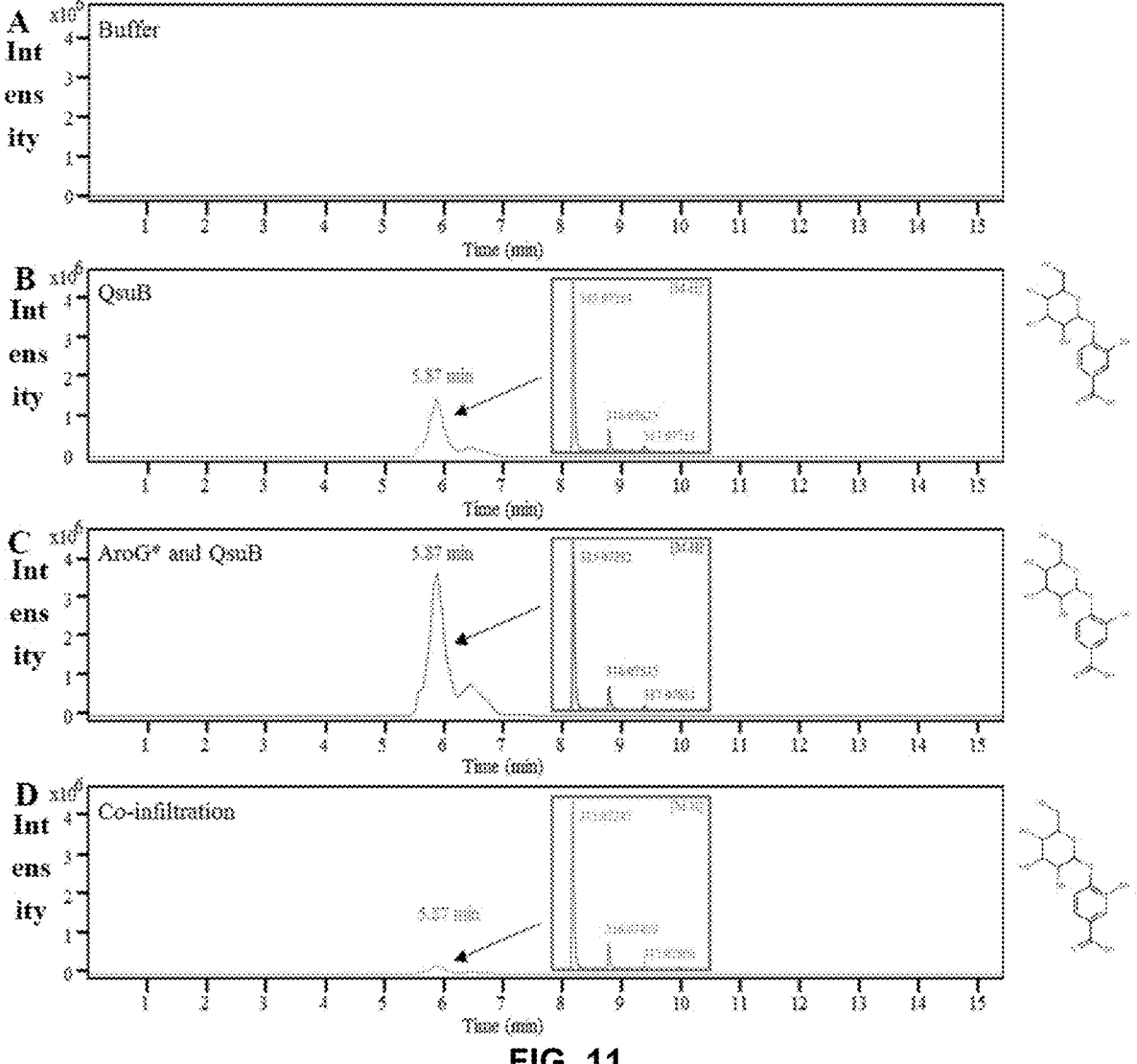

FIG. 11. Representative HPLC-ESI-TOF MS (high-performance liquid chromatography—electrospray ionization—time-of-flight mass spectrometry) chromatograms of the PCA glucose conjugate detected in non-hydrolysed metabolite extracts obtained from tobacco leaves transiently expressing QsuB alone (B), AroG* and QsuB (C), or the five enzymes AroG*, QsuB, PmdA, PmdB, and PmdC (D). Metabolite extracts obtained from tobacco leaves inoculated with the infiltration buffer were used as control (A). Insets in each chromatogram show the mass spectra of the PCA glucose conjugate (PCA-4-O-glucose is arbitrary shown).

Figure 12A:
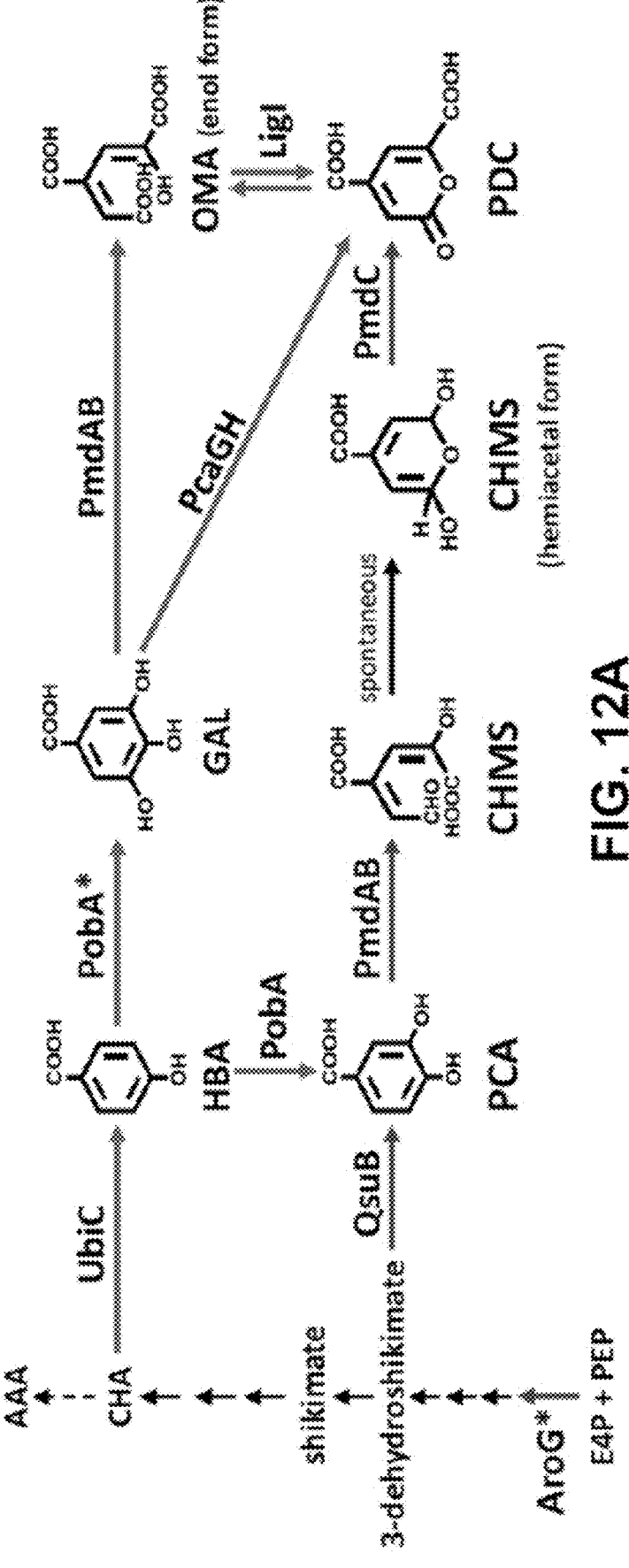

FIG. 12A. Strategy used for the production of PDC in plants. De novo biosynthetic pathway for PDC synthesis. Abbreviations are: E4P, erythrose 4-phosphate; PEP, phosphoenolpyruvate; CHA, chorismate; AAA, aromatic amino acids; PCA, protocatechuic acid; CHMS, 4-carboxy-2-hydroxymuconate-6-semialdehyde; PDC, 2-pyrone-4,6-dicarboxylic acid; HBA, 4-hydroxybenzoate; GAL, gallic acid; OMA, 4-oxalomesaconate. Enzymes names: AroG*, feedback-insensitive 3-deoxy-D-arabino-heptulosonate (DAHP) synthase with L175Q mutation; PmdA, PCA 4,5-dioxygenase alpha subunit; PmdB, PCA 4,5-dioxygenase beta subunit; PmdC, CHMS dehydrogenase; QsuB, 3-dehydroshikimate dehydratase; UbiC, chorismate pyruvate lyase; PobA, 4-hydroxybenzoate hydroxylase; PcaGH, protocatechuate 3,4-dioxygenase; LigI, 2-pyrone-4,6-dicarboxylate hydrolase.

FIG. 12B. Strategy used for the production of PDC in plants. Production of PDC in tobacco leaves by the transient expression of the proposed de novo biosynthetic pathway.

FIG. 12C. Strategy used for the production of PDC in plants. Production of PDC in tobacco leaves by the transient expression of pcaG and pcaH through GAL route.

DETAILED DESCRIPTION OF THE INVENTION

The foregoing aspects and others will be readily appreciated by the skilled artisan from the following description of illustrative embodiments when read in conjunction with the accompanying drawings.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The term "about" refers to a value including 10% more than the stated value and 10% less than the stated value.

As used herein, the term "promoter" refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. Promoters are located 5' to the transcribed gene, and as used herein, include the sequence 5' from the translation start codon.

A "constitutive promoter" is one that is capable of initiating transcription in nearly all cell types, whereas a "cell type-specific promoter" initiates transcription only in one or a few particular cell types or groups of cells forming a tissue. In some embodiments, the promoter is secondary cell wall-specific and/or fiber cell-specific. A "fiber cell-specific promoter" refers to a promoter that initiates substantially higher levels of transcription in fiber cells as compared to other non-fiber cells of the plant. A "secondary cell wall-specific promoter" refers to a promoter that initiates substantially higher levels of transcription in cell types that have secondary cell walls, e.g., lignified tissues such as vessels and fibers, which may be found in wood and bark cells of a tree, as well as other parts of plants such as the leaf stalk. In some embodiments, a promoter is fiber cell-specific or secondary cell wall-specific if the transcription levels initiated by the promoter in fiber cells or secondary cell walls, respectively, are at least 3-fold, 4-fold, 5-fold, 6-fold, 7-fold, 8-fold, 9-fold, 10-fold, 50-fold, 100-fold, 500-fold, 1000-fold higher or more as compared to the transcription levels initiated by the promoter in other tissues, resulting in the encoded protein substantially localized in plant cells that possess fiber cells or secondary cell wall, e.g., the stem of a plant. Non-limiting examples of fiber cell and/or secondary cell wall specific promoters include the promoters directing expression of the genes IRX1, IRX3, IRX5, IRX7, IRX8, IRX9, IRX10, IRX14, NST1, NST2, NST3, MYB46, MYB58, MYB63, MYB83, MYB85, MYB103, PAL1, PAL2, C3H, CcOAMT, CCR1, FSH, LAC4, LAC17, CADc, and CADd. See, e.g., Turner et al 1997; Meyer et al 1998; Jones et al 2001; Franke et al 2002; Ha et al 2002; Rohde et al 2004; Chen et al 2005; Stobout et al 2005; Brown et al 2005; Mitsuda et al 2005; Zhong et al 2006; Mitsuda et al 2007; Zhong et al 2007a, 2007b; Zhou et al 2009; Brown et al 2009; McCarthy et al 2009; Ko et al 2009; Wu et al 2010; Berthet et al 2011. In some embodiments, a promoter is substantially identical to a promoter from the lignin biosynthesis pathway. A promoter originated from one plant species may be used to direct gene expression in another plant species.

A polynucleotide or amino acid sequence is "heterologous" to an organism or a second polynucleotide or amino acid sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety, or a gene that is not naturally expressed in the target tissue).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

A homologous enzyme is an enzyme that has a polypeptide sequence that is at least 70%, 75%, 80%, 85%, 90%, 95% or 99% identical to any one of the enzymes described in this specification or in an incorporated reference. The homologous enzyme comprises or retains amino acid residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

The terms "host cell" of "host organism" is used herein to refer to a living biological cell that can be transformed via insertion of an expression vector.

The terms "expression vector" or "vector" refer to a compound and/or composition that transduces, transforms, or infects a host cell, thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "plant" as used herein can refer to a whole plant or part of a plant, e.g., seeds, and includes plants of a variety of ploidy levels, including aneuploid, polyploid, diploid and haploid. The term "plant part," as used herein, refers to shoot vegetative organs and/or structures (e.g., leaves, stems and tubers), branches, roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, and plant tissue (e.g., vascular tissue, ground tissue, and the like), as well as individual plant cells, groups of plant cells (e.g., cultured plant cells), protoplasts, plant extracts, and seeds. The class of plants that can be used in the methods of the invention is generally as broad as the class of higher and lower plants amenable to transformation techniques, including angiosperms (monocotyledonous and dicotyledonous plants), gymnosperms, ferns, bryophytes, and multicellular algae.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The amino acid sequence of *Comamonas testosteroni* (*Pseudomonas testosteroni*) protocatechuate 4,5-dioxygenase alpha subunit (PmdA) is as follows:

```
                                          (SEQ ID NO: 1)
          10         20         30         40
MALEKPYLDV PGTIIFDAEQ SRKGYWLNQF CMSLMKAENR 50         60         70         80
ERFRADERAY LDEWAMTEEQ KQAVLARDLN WCMRTGGNIY 90        100        110        120
FLAKIGATDG KSFQQMAGSM TGMTEEEYRA MMMGGGRSAE 130        140
GNRYVGEDGD AQAHHQPQGS AGNQNKEGN
```

In some embodiment, the PmdA, or homologous enzyme thereof, comprises an amino acid sequence having equal to or more than about 70%, 75%, 80%, 85%, 90%, 95%, or 99% amino acid sequence identity to SEQ ID NO:1. In some embodiments, the PmdA, or homologous enzyme thereof, comprises one or more of the following conserved amino acid sequences:

```
                                          (SEQ ID NO: 12)
    KPYLDVPGT, (SEQ ID NO: 13)
    IFDAEQSRKGYWLNQFCMSLMKAENRERF, (SEQ ID NO: 14)
    DERAYLDEWAMTEEQKQAVLARDLNWC, (SEQ ID NO: 15)
    GGNIYFLAKIGATDGKSFQQMAGSMTGMTEEEYR, (SEQ ID NO: 16)
    GGRSA,
    and (SEQ ID NO: 17)
    VGEDGDAQAH.
```

The amino acid sequence of *Comamonas testosteroni* (*Pseudomonas testosteroni*) protocatechuate 4,5-dioxygenase beta subunit (PmdB) is as follows:

```
                                          (SEQ ID NO: 2)
          10         20         30         40
MARITASVFT SHVPAIGAAM DMGKTQEAYW APLFKGYDFS 50         60         70         80
RQWMKDNKPD VIFLVYNDHA TAFSLDCIPT FAIGTAAEFQ 90        100        110        120
PADEGWGPRP VPKVVGHPDL ASHIAQSVIQ QDFDLTIVNK 130        140        150        160
MDVDHGLTVP LSLMCGEQDP KTGSWPCPVI PFAVNVVQYP 170        180        190        200
VPTGQRCFNL GRAIRKAVES YDQDINVHIW GTGGMSHQLQ 210        220        230        240
GARAGLINKE WDNQFLDLLV ENPHGLAQMP HIDYVREAGS 250        260        270        280
EGIELVMWLI ARGAMSDVDG PAPLPKVAHR FYHVPASNTA

VGHLILENQ
```

In some embodiment, the PmdB, or homologous enzyme thereof, comprises an amino acid sequence having equal to or more than about 70%, 75%, 80%, 85%, 90%, 95%, or 99% amino acid sequence identity to SEQ ID NO:2. In some embodiments, the PmdB, or homologous enzyme thereof, comprises one or more of the following conserved amino acid sequences:

```
                            (SEQ ID NO: 18)
     MARITASV, (SEQ ID NO: 19)
     TSHVPAIGAA, (SEQ ID NO: 20)
     PDVIFLVYNDHATAFSLD, (SEQ ID NO: 21)
     IPTFAIGTAAEF, (SEQ ID NO: 22)
     IPTFAIGTAAEF, (SEQ ID NO: 23)
     LASHIAQSVIQ, (SEQ ID NO: 24)
     DFDLTIVNKMDVDHGLTVPLSLMCGE, (SEQ ID NO: 25)
     VIPFAVNVVQYPVP, (SEQ ID NO: 26)
     IWGTGGMSHQLQGARAGLIN, (SEQ ID NO: 27)
     YVREAGSEGIELVMWLIARGAM,
     and (SEQ ID NO: 28)
     HVPASNTAVGHLILEN.
```

The amino acid sequence of *Comamonas testosteroni* 4-carboxy-2-hydroxymuconate-6-semialdehyde dehydrogenase (PmdC) is as follows:

```
                            (SEQ ID NO: 3)
          10        20        30        40
MSKTIKVALA GAGAFGIKHL DGIKNIDGVE VVSLVGRRFD 50        60        70        80
QTKEVADKYG IAHVATDLAE SLALPEVDAV ILCTPTQMHA 90       100       110       120
EQAIACMKAG KHVQVEIPLA DALKDAQEVA ELQKQTGLVA 130       140       150       160
MVGHTRRFNP SHQWVHKKIE AGEFNIQQMD VQTYFFRRTN 170       180       190       200
MNALGQARSW TDHLLWHHAA HTVDLFAYQA GSPIVKANAV 210       220       230       240
QGPIHKDLGI AMDMSIQLKA ANGAICTLSL SFNNDGPLGT 250       260       270       280
FFRYIGDTGT YLARYDDLYT GKDEKIDVSQ VDVSMNGIEL 290       300       310
QDREFFAAIR EGREPNSSVQ QVFNCYKVLH DLEQQLNAD
```

In some embodiment, the PmdC, or homologous enzyme thereof, comprises an amino acid sequence having equal to or more than about 70%, 75%, 80%, 85%, 90%, 95%, or 99% amino acid sequence identity to SEQ ID NO:3. In some embodiments, the PmdC, or homologous enzyme thereof, comprises one or more of the following conserved amino acid sequences:

```
                            (SEQ ID NO: 29)
     ALAGAGAFG, (SEQ ID NO: 30)
     KNIDGVE, (SEQ ID NO: 31)
     VDAVILCTPTQMHAEQAIACM, (SEQ ID NO: 32)
     AGKHVQVEIPLAD, (SEQ ID NO: 33)
     MVGHTRRFNPSHQ, (SEQ ID NO: 34)
     IQQMDVQTYFFRR, (SEQ ID NO: 35)
     RSWTDHLLWHHAAHTVDLFAYQAG, (SEQ ID NO: 36)
     ANAVQGPIH, (SEQ ID NO: 37)
     LGIAMDMSIQLK, (SEQ ID NO: 38)
     GAICTLSLSFNNDGPLGTFFRYI, (SEQ ID NO: 39)
     ARYDDL, (SEQ ID NO: 40)
     VDVSMNGIELQDREF,
     and (SEQ ID NO: 41)
     AAIREGREPNSSV.
```

The amino acid sequence of *E. coli* 3-deoxy-D-arabino-heptulosonate 7-phosphate synthase (AroG) is as follows:

```
                            (SEQ ID NO: 4)
          10        20        30        40
MNYQNDDLRI KEIKELLPPV ALLEKFPATE NAANTVAHAR 50        60        70        80
KAIHKILKGN DDRLLVVIGP CSIHDPVAAK EYATRLLALR 90       100       110       120
EELKDELEIV MRVYFEKPRT TVGWKGLIND PHMDNSFQIN 130       140       150       160
DGLRIARKLL LDINDSGLPA AGEFLDMITP QYLADLMSWG 170       180       190       200
AIGARTTESQ VHRELASGLS CPVGFKNGTD GTIKVAIDAI 210       220       230       240
NAAGAPHCFL SVTKWGHSAI VNTSGNGDCH IILRGGKEPN 250       260       270       280
YSAKHVAEVK EGLNKAGLPA QVMIDFSHAN SSKQFKKQMD 290       300       310       320
VCADVCQQIA GGEKATTGVM VESHLVEGNQ SLESGEPLAY 330       340       350
GKSITDACIG WEDTDALLRQ LANAVKARRG
```

In some embodiment, the AroG, or homologous enzyme thereof, comprises an amino acid sequence having equal to or more than about 70%, 75%, 80%, 85%, 90%, 95%, or 99% amino acid sequence identity to SEQ ID NO:4. In some embodiments, the AroG, or homologous enzyme thereof, comprises one or more of the following conserved amino acid sequences:

```
                                       (SEQ ID NO: 42)
          MRVYFEKPRT, (SEQ ID NO: 43)
          VGWKGLIN, (SEQ ID NO: 44)
          GLRIARK, (SEQ ID NO: 45)
          WGAIGARTTESQVHR, (SEQ ID NO: 46)
          HIILRGG,
          and (SEQ ID NO: 47)
          SHANS.
```

In a particular embodiment, the feedback-resistant DAHP synthase (L175Q) (AroG*) has the following amino acid sequence:

```
                                       (SEQ ID NO: 5)
                 10         20         30         40
          MNYQNDDLRI KEIKELLPPV ALLEKFPATE NAANTVAHAR 50         60         70         80
          KAIHKILKGN DDRLLVVIGP CSIHDPVAAK EYATRLLALR 90        100        110        120
          EELKDELEIV MRVYFEKPRT TVGWKGLIND PHMDNSFQIN 130        140        150        160
          DGLRIARKLL LDINDSGLPA AGEFLDMITP QYLADLMSWG 170        180        190        200
          AIGARTTESQ VHREQASGLS CPVGENNGTD GTIKVAIDAI 210        220        230        240
          NAAGAPHCFL SVTKWGHSAI VNTSGNGDCH IILRGGKEPN 250        260        270        280
          YSAKHVAEVK EGLNKAGLPA QVMIDFSHAN SSKQFKKQMD 290        300        310        320
          VCADVCQQIA GGEKAIIGVM VESHLVEGNQ SLESGEPLAY 330        340        350
          GKSITDACIG WEDTDALLRQ LANAVKARRG
```

In some embodiment, the AroG*, or homologous enzyme thereof, comprises an amino acid sequence having equal to or more than about 70%, 75%, 80%, 85%, 90%, 95%, or 99% amino acid sequence identity to SEQ ID NO:5. In some embodiments, the AroG*, or homologous enzyme thereof, comprises the Q at position 175. In some embodiments, the AroG*, or homologous enzyme thereof, comprises one or more of the following conserved amino acid sequences:

```
                                       (SEQ ID NO: 42)
          MRVYFEKPRT, (SEQ ID NO: 43)
          VGWKGLIN, (SEQ ID NO: 44)
          GLRIARK, (SEQ ID NO: 45)
          WGAIGARTTESQVHR,
```

-continued
```
                                       (SEQ ID NO: 46)
          HIILRGG,
          and (SEQ ID NO: 47)
          SHANS.
```

The amino acid sequence of *Pseudomonas aeruginosa* p-hydroxybenzoate 3-monooxygenase (p-hydroxybenzoate hydroxylase) (PobA) is as follows:

```
                                       (SEQ ID NO: 6)
                 10         20         30         40
          MKTQVAIIGA GPSGLLLGQL LHKAGIDNVI LERQTPDYVL 50         60         70         80
          GRIRAGVLEQ GMVDLLREAG VDRRMARDGL VHEGVEIAFA 90        100        110        120
          GQRRRIDLKR LSGGKTVTVY GQTEVTRDLM EAREACGATT 130        140        150        160
          VYQAAEVRLH DLQGERPYVT FERDGERLRL DCDYIAGCDG 170        180        190        200
          FHGISRQSIP AERLKVFERV YPFGWLGLLA DTPPVSHELI 210        220        230        240
          YANHPRGFAL CSQRSATRSR YYVQVPLTEK VEDWSDERFW 250        260        270        280
          TELKARLRAE VAEKLVTGPS LEKSIAPLRS FVVEPMQHGR 290        300        310        330
          LFLAGDAAHI VPPTGAKGLN LAASDVSTLY RLLLKAYREG 340        350        360        370
          RGELLERYSA ICLRRIWKAE RFSWWMTSVL HRFPDTDAFS 380        390
          QRIQQTELEY YLGSEAGLAT IAENYVGLPY EEIE
```

In some embodiment, the PobA, or homologous enzyme thereof, comprises an amino acid sequence having equal to or more than about 70%, 75%, 80%, 85%, 90%, 95%, or 99% amino acid sequence identity to SEQ ID NO:6. In some embodiments, the PobA, or homologous enzyme thereof, comprises one or more of the following conserved amino acid sequences:

```
                                       (SEQ ID NO: 48)
          GLLLGQLL, (SEQ ID NO: 49)
          RIRAG, (SEQ ID NO: 50)
          VTVYGQTEVT, (SEQ ID NO: 51)
          IAGCDG, (SEQ ID NO: 52)
          VYPFGWLG, (SEQ ID NO: 53)
          RGFALCS, (SEQ ID NO: 54)
          TRSRYY, (SEQ ID NO: 55)
          EKLVTGPS,
```

-continued

```
                                        (SEQ ID NO: 56)
EKSIAPLRSFV, (SEQ ID NO: 57)
EKSIAPLRSFVLAASD, (SEQ ID NO: 58)
WKAERFSWWMT,
and (SEQ ID NO: 59)
AENYVGLPYE.
```

PobA* is a p-hydroxybenzoate 3-monooxygenase that is mutant such that it catalyzes HBA into GAL. In some embodiments, the PobA* is reduced (as compared to the unmodified wild-type PobA) or unable to catalyze HBA into PCA. In some embodiments, the PobA* has the analogous Y385F and/or T294A mutations (the amino acid residue positions as corresponding to SEQ ID NO:6).

In a particular embodiment, the PobA* has the following amino acid sequence:

```
                                        (SEQ ID NO: 7)
        10         20         30         40
MKTQVAIIGA GPSGLLLGQL LHKAGIDNVI LERQTPDYVL 50         60         70         80
GRIRAGVLEQ GMVDLLREAG VDRRMARDGL VHEGVEIAFA 90        100        110        120
GQRRRIDLKR LSGGKTVTVY GQTEVTRDLM EAREACGATT 130        140        150        160
VYQAAEVRLH DLQGERPYVT FERDGERLRL DCDYIAGCDG 170        180        190        200
FHGISRQSIP AERLKVFERV YPFGWLGLLA DTPPVSHELI 210        220        230        240
YANHPRGFAL CSQRSATRSR YYVQVPLTEK VEDWEDERFW 250        260        270        280
TELKARLPAE VAEKLVTGPS LEKSIAPLRS FVVEPMQHGR 290        300        310        320
LFLAGDAAHI VPPAGAKGLN LAASDVSTLY RLLLKAYREG 330        340        350        360
RGELLERYSA ICLRRIWKAE RFSWWMTSVL HRFPDTDAFS 370        380        390
QRIQQTELEY YLGSEAGLAT IAENFVGLPY EEIE
```

In some embodiment, the PobA*, or homologous enzyme thereof, comprises an amino acid sequence having equal to or more than about 70%, 75%, 80%, 85%, 90%, 95%, or 99% amino acid sequence identity to SEQ ID NO:7. The PobA*, or homologous enzyme thereof, comprises the F at position 385 and/or the A at position 294. These two amino acid residues are each alone or together important for the enzymatic activity of catalyzing HBA into GAL. In some embodiments, the PobA*, or homologous enzyme thereof, comprises one or more of the following conserved amino acid sequences: GLLLGQLL (SEQ ID NO:48), RIRAG (SEQ ID NO:49), VTVYGQTEVT (SEQ ID NO:50), IAGCDG (SEQ ID NO:51), VYPFGWLG (SEQ ID NO:52), RGFALCS (SEQ ID NO:53), TRSRYY (SEQ ID NO:54), EKLVTGPS (SEQ ID NO:55), EKSIAPLRSFV (SEQ ID NO:56), EKSIAPLRSFVLAASD (SEQ ID NO:57), WKAERFSWWMT (SEQ ID NO:58), and AENFVGLPYE (SEQ ID NO:60).

TABLE 6

| Suitable PcaG for the invention. | |
| --- | --- |
| Enzyme name [Organism] | Accession number |
| protocatechuate 3,4-dioxygenase subunit alpha [Aeromonas caviae] | GJB79204.1 |
| MULTISPECIES: protocatechuate 3,4-dioxygenase subunit alpha [Gammaproteobacteria] | WP_010955312.1 |
| protocatechuate 3,4-dioxygenase subunit alpha [Stenotrophomonas rhizophila] | AXQ49722.1 |
| protocatechuate 3,4-dioxygenase subunit alpha [Pantoea sp. Ap-967] | WP_167065900.1 |
| protocatechuate 3,4-dioxygenase alpha subunit [Stenotrophomonas maltophilia] | AFH89644.1 |
| protocatechuate 3,4-dioxygenase subunit alpha [Escherichia coli] | MRF38928.1 |
| protocatechuate 3,4-dioxygenase subunit alpha [Pantoea sp. Tr-811] | WP_167271347.1 |
| protocatechuate 3,4-dioxygenase subunit alpha [Gammaproreobacteria bacterium] | NPA19495.1 |
| protocatechuate 3,4-dioxygenase subunit alpha [Priestia aryabhattai] | QPN46230.1 |
| protocatechuate 3,4-dioxygenase subunit ] alpha [Gammaproteobacteria bacterium | NOY04354.1 |

The amino acid sequence of *E. coli* protocatechuate 3,4-dioxygenase subunit alpha (PcaG) is as follows:

```
                                        (SEQ ID NO: 8)
        10         20         30         40
MPIELLPETP SQTAGPYVHI GLALEAAGNP TRDQEIWNCL 50         60         70         80
AKPDAPGEHI LLIGHVYDGN GHLVRDSFLE VWQADANGEY 90        100        110        120
QDAYNLENAF NSFGRTATTF DAGEWTLQTV KPGVVNNAAG 130        140        150        160
VPMAPHINIS LFARGINIHL HTRLYFDDEA QANAKCPVLN 170        180        190        200
LIEQPQRRET LIAKRCEVDG KTAYRFDIRI QGEGETVFFD F
```

In some embodiment, the PcaG, or homologous enzyme thereof, comprises an amino acid sequence having equal to or more than about 70%, 75%, 80%, 85%, 90%, 95%, or 99% amino acid sequence identity to SEQ ID NO:8. In some embodiments, the PcaG, or homologous enzyme thereof, comprises one or more of the following conserved amino acid sequences:

```
                                        (SEQ ID NO: 61)
MPIELLPETPSQTAGPYVHIGLALEAAGNPTRDQEIWN, (SEQ ID NO: 62)
VYDGNGHLVRDSF, (SEQ ID NO: 63)
WQADANG, (SEQ ID NO: 64)
FNSFGRTATTFDAGEWT, (SEQ ID NO: 65)
TVKPGVV, (SEQ ID NO: 66)
NAAGVPMAPHINISLFARGINIHLHTRLYFDDEA, (SEQ ID NO: 67)
ANAKCPVLNLIEQPQRRETL,
and
```

-continued (SEQ ID NO: 68)

AKRCEVDGKTAYRFDIRIQGEGETVFFDF.

Suitable PcaG for the invention are listed in Table 6.

TABLE 7

Suitable PcaH for the invention.

| Enzyme name [Organism] | Accession number |
|---|---|
| protocatechuate 3,4-dioxygenase subunit beta [*Stenotrophomonas rhizophila*] | AXQ49723.1 |
| MULTISPECIES: protocatechuate 3,4-dioxygenase subunit alpha [unclassified Pantoea] | WP_167065903.1 |
| protocatechuate 3,4-dioxygenase subunit beta [*Aeromonas caviae*] | GJB79205.1 |
| MULTISPECIES: protocatechuate 3,4-dioxygenase subunit beta [Gammaproteobacteria] | WP_009682255.1 |
| protocatechuate 3,4-dioxygenase subunit beta [*Escherichia coli*] | MRF38927.1 |
| protocatechuate 3,4-dioxygenase subunit alpha [*Priestia aryabhattai*] | QPN46229.1 |
| protocatechuate 3,4-dioxygenase alpha subunit [*Stenotrophomonas maltophilia*] | AFH89645.1 |

The amino acid sequence of *E. coli* protocatechuate 3,4-dioxygenase subunit beta (PcaH) is as follows:

```
                                      (SEQ ID NO: 9)
          10         20         30         40
MPAQDNSRFV IRDRNWHPKA LTPDYKTSVA RSPRQALVSI 50         60         70         80
PQSISETTGP DFSHLGFGAH DHDLLLNFNN GGLPIGERII 90        100        110        120
VAGRVVDQYG KPVPNTLVEM WQANAGGRYR HKNDRYLAPL 130        140        150        160
DPNFGGVGRC LTDRDGYYSF RTIKPGPYPW RNGPNDWRPA 170        180        190        200
HIHFAISGPS IATKLITQLY FEGDPLIPMC PIVKSIANPQ 210        220        230
AVQQLIAKLD MSNANPMDCL AYRFDIVLRG QRKTHFENC
```

In some embodiment, the PcaH, or homologous enzyme thereof, comprises an amino acid sequence having equal to or more than about 70%, 75%, 80%, 85%, 90%, 95%, or 99% amino acid sequence identity to SEQ ID NO:9. In some embodiments, the PcaH, or homologous enzyme thereof, comprises one or more of the following conserved amino acid sequences: MPAQDNSRFVIRDRNWHPKA-LTPDYKTS (SEQ ID NO:69), ARSPRQALVSIPQSI-SETTGP (SEQ ID NO:70), HLGFGAHDHDLLLNFNNG-GLP (SEQ ID NO:71), GERIIVAGRVVDQYG (SEQ ID NO:72), PVPNTLVE (SEQ ID NO:73), WQANAG-GRYRHKNDRYLAPLDPNFGGVGRCLTD (SEQ ID NO:74), FRTIKPGPYPWRNGPNDWRPAHIH (SEQ ID NO:75), SGPSIATKLITQLYFEGDPLIP (SEQ ID NO:76), CPIVKSIANP (SEQ ID NO:77), AVQQLIAK-LDMSNANPMDCLAYRFDI (SEQ ID NO:78), and LRGQRKTHFE (SEQ ID NO:79). Suitable PcaH for the invention are listed in Table 7.

The amino acid sequence of *Sphingomonas paucimobilis* 2-pyrone-4,6-dicarboxylate hydrolase (LigI) is as follows:

```
                                      (SEQ ID NO: 10)
          10         20         30         40
MTNDERILSW NETPSKPRYT PPPGAIDAHC HVFGPMAQFP 50         60         70         80
FSPKAKYLPR DAGPDMLFAL RDHLGFARNV IVQASCHGTD 90        100        110        120
NAATLDAIAR AQGKARGIAV VDPAIDEAEL AALHEGGMRG 130        140        150        160
IRFNFLKRLV DDAPKDKFLE VAGRLPAGWH VVIYFEADIL 170        180        190        200
EELRPFMDAI PVPIVIDHMG RPDVRQGPDG ADMKAFRRLL 210        220        230        240
DSREDIWFKA TCPDRLDPAG PPWDDFARSV APLVADYADR 250        260        270        280
VIWGTDWPHP NMQDAIPDDG LVVDMIPRIA PTPELQHKML

290
VTNPMRLYWS EEM
```

In some embodiment, the LigI, or homologous enzyme thereof, comprises an amino acid sequence having equal to or more than about 70%, 75%, 80%, 85%, 90%, 95%, or 99% amino acid sequence identity to SEQ ID NO:10. In some embodiments, the LigI, or homologous enzyme thereof, comprises one or more of the following conserved amino acid residues of SEQ ID NO:10 at positions: 47, 75, 122, 128, 154, 178, and 251, which are each independently or all important for the enzymatic activity of LigI in that they involved in the substrate binding site. A LigI, or homologous enzyme thereof, comprises the following conserved amino acid residue of SEQ ID NO:10 at position 246 which is the active site for the enzymatic activity of LigI.

The amino acid sequence of *Corynebacterium glutami-cum* 3-dehydroshikimate dehydratase (QsuB) is as follows:

```
                                      (SEQ ID NO: 11)
          10         20         30         40
MRTSIATVCL SGTLAEKLRA AADAGFDGVE IFEQDLVVSP 50         60         70         80
HSAEQIRQRA QDLGLTLDLF QPFRDFEGVE EEQFLKNLHR 90        100        110        120
LEEKFKLMNR LGIEMILLCS NVGTATINDD DLFAEQLHRA 130        140        150        160
ADLAEKYNVK IAYEALAWGK FVNDFEHAHA LVEKVNHKAL 170        180        190        200
GTCLDTFHIL SRGWETDEVE NIPAEKIFFV QLADAPKLSM 210        220        230        240
DILSWSRHHR VFPGEGDFDL VKFMVHLAKT GYDGPISLEI 250        260        270        280
FNDSFRKAEV GRTAIDGLRS LRWLEDQTWH ALSAEDRPSA 290        300        310        320
LELRALPEVA EPEGVDFIEI ATGRLGETIR VLHQLGFRLG 330        340        350        360
GHHCSKQDYQ VWTQGDVRIV VCDRGATGAP TTISAMGFDT 370        380        390        400
PDPEAAHARA ELLRAQTIDR PHIEGEVDLK GVYAPDGVEL
```

```
                    -continued
        410       420       430       440
FFAGPSPDGM PEWLPEFGVE KQEAGLIEAI DHVNFAQPWQ 450       460       470       480
HFDEAVLFYT ALMALETVRE DEFPSPIGLV RNQVMRSPND 490       500       510       520
AVRLLLSVAP EDGEQGDFLN AAYPEHIALA TADIVAVAER 530       540       550       560
ARKRGLDFLP VPENYYDDVQ ARFDLPQEFL DTLKENHLLY 570       580       590       600
DRDENGEFLH FYTRTLGTLF FEVVERRGGF AGWGETNAPV

610
RLAAQYREVR DLERGIPN
```

In some embodiment, the QsuB, or homologous enzyme thereof, comprises an amino acid sequence having equal to or more than about 70%, 75%, 80%, 85%, 90%, 95%, or 99% amino acid sequence identity to SEQ ID NO:11. In some embodiments, the QsuB, or homologous enzyme thereof, comprises one or more of the following conserved amino acid residues of SEQ ID NO:11 at positions: 134, 165, 191, 239, 432, 506, and 582, which are each independently or all important for the enzymatic activity of QsuB in that they involved in metal binding.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

In-Planta Production of the Biodegradable Polyester
Precursor 2-pyrone-4,6-dicarboxylic Acid (PDC):
Stacking Reduced Biomass Recalcitrance with
Value-Added Co-Product 2-pyrone-4,6-dicarboxylic acid (PDC), a chemically stable intermediate that naturally occurs during microbial degradation of lignin by bacteria, represents a promising building block for diverse biomaterials and polyesters such as biodegradable plastics. The lack of chemical synthesis method has hindered large-scale utilization of PDC and metabolic engineering approaches for its biosynthesis have recently emerged. In this study, a strategy for the production of PDC via manipulation of the shikimate pathway using plants as green factories is demonstrated. In tobacco leaves, it is first shown that transient expression of bacterial feedback-resistant 3-deoxy-D-arabinoheptulosonate 7-phosphate synthase (AroG) and 3-dehydroshikimate dehydratase (QsuB) produces high titers of protocatechuate (PCA), which is in turn efficiently converted into PDC upon co-expression of PCA 4,5-dioxygenase (PmdAB) and 4-carboxy-2-hydroxymuconate-6-semialdehyde dehydrogenase (PmdC) from *Comamonas testosterone*. It is validated in Arabidopsis that stable expression of AroG in a genetic background containing the QsuB gene enhances PCA content in plant biomass, presumably via an increase of the carbon flux through the shikimate pathway. Further, introducing AroG and the PDC biosynthetic genes (PmdA, PmdB, and PmdC) into the Arabidopsis QsuB background, or introducing the five genes (AroG, QsuB, PmdA, PmdB, and PmdC) stacked on a single construct into wild-type plants resulted in PDC titers of ~1% and ~3% dry weight in plant biomass, respectively. Consistent with previous observations, all PDC producing lines show strong reductions of lignin content in stems as a consequence of QsuB expression. This low lignin trait is accompanied with improvements of biomass saccharification efficiency due reduced cell wall recalcitrance to enzymatic degradation. Importantly, most transgenic lines show no reduction in biomass yields. Therefore, it is concluded that engineering plants with the proposed de-novo PDC pathway provides an avenue to enrich biomass with a value-added co-product and to improve biomass quality for the supply of fermentable sugars. Implementing this strategy into bioenergy crops has the potential to support existing microbial fermentation approaches that exploit lignocellulosic biomass feedstocks for PDC production.

Figure 1:
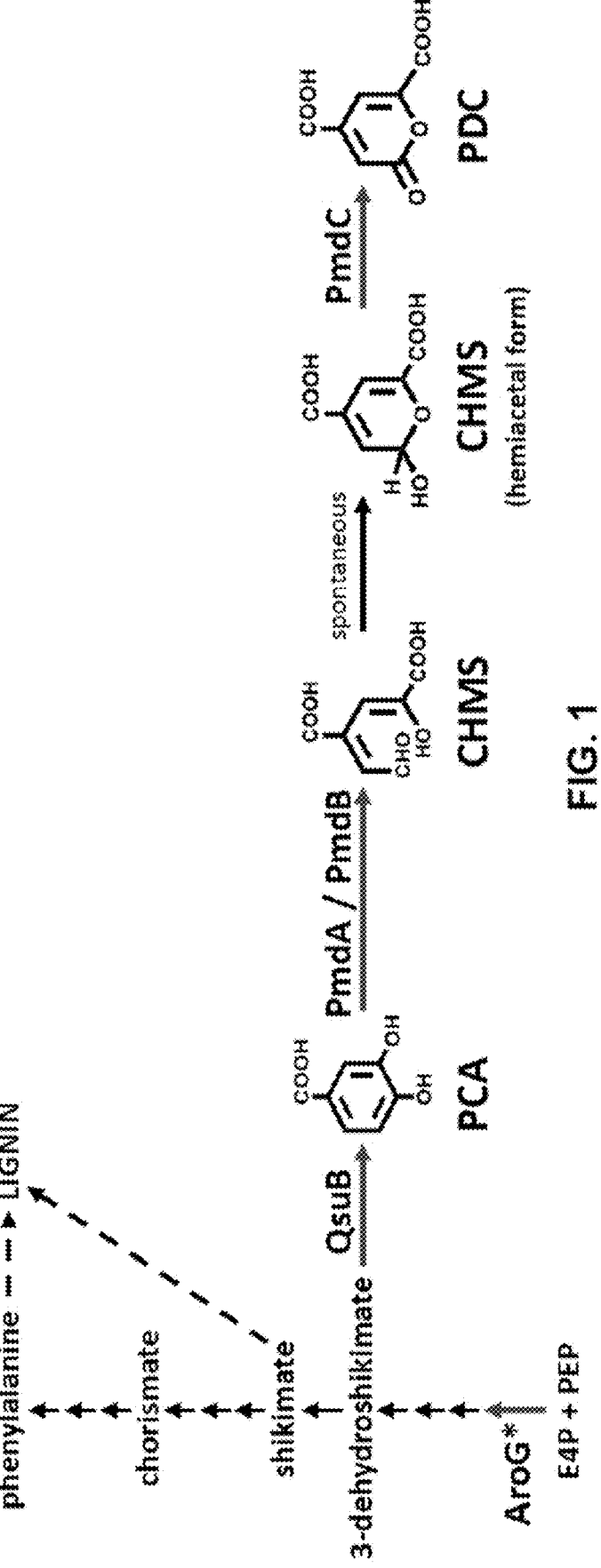
FIG. 1. Schematic diagram of the metabolic pathway implemented in plant plastids to produce PDC. Red arrows indicate biosynthetic steps catalyzed by bacterial enzymes introduced in Arabidopsis. Abbreviation are: E4P, erythrose 4-phosphate; PEP, phosphoenolpyruvate; PCA, protocatechuic acid; CHMS, 4-carboxy-2-hydroxymuconate-6-semialdehyde; PDC, 2-pyrone-4,6-dicarboxylic acid. Enzymes names: AroG*, feedback-insensitive 3-deoxy-D-arabino-heptulosonate (DAHP) synthase with L175Q mutation; PmdA, PCA 4,5-dioxygenase alpha subunit; PmdB, PCA 4,5-dioxygenase beta subunit; PmdC, CHMS dehydrogenase; QsuB, 3-dehydroshikimate dehydratase.

In this example, it is exploited that the *C. testosteroni* genes encoding the alpha and beta subunits of PCA 4,5-dioxygenase (PmdA and PmdB) and CHMS dehydrogenase (PmdC) for PDC production in plants (FIG. 1). This approach also leverages previously reported engineering strategies in Arabidopsis that (1) enable PCA overproduction by expression of a 3-dehydroshikimate dehydratase (QsuB) (Eudes et al., 2015) and (2) increase the metabolic flux through the shikimate pathway by expression of feedback-resistant 3-deoxy-D-arabinoheptulosonate 7-phosphate synthase (DAHPS, hereafter AroG*) (Tzin et al., 2012; Eudes et al., 2018).

Using a leaf transient expression system in tobacco (*Nicotiana benthamiana*), it is first shown that all three enzymes (PmdA, PmdB, and PmdC) are essential for the conversion of PCA into PDC, while co-expression of AroG* with QsuB increases the production of PCA. Using Arabidopsis as a model for stable transformation, it is confirmed that introducing AroG* into a transgenic background that contains QsuB increases PCA titers, which are up ~3.5-fold compared the parental line. Next, a gene-stacking approach for introducing the four enzymes AroG*, PmdA, PmdB, and PmdC into the QsuB parental line (PDC-4GxQsuB) resulted in PDC production (up to 1% dry weight). Furthermore, transformation of wild-type Arabidopsis with a construct consisting of the five genes located on a single plasmid for co-expression of AroG*, QsuB, PmdA, PmdB, and PmdC (PDC-5G) enabled higher PDC titers in plant biomass (~3% dry weight). Importantly, the different Arabidopsis PDC-producing lines show reduced lignin contents and improved biomass saccharification efficiencies compared to wild-type control plants, which is presumably a consequence of QsuB expression in lignifying tissues as previously observed in other Arabidopsis plants engineered with the same QsuB gene (Eudes et al., 2015; Aznar et al., 2018).

Consequently, it is successfully demonstrated in this example an engineering strategy for enriching plant biomass with PDC as a value-added co-product while conferring a reduced biomass recalcitrance trait that enables higher yields of fermentable sugars for downstream biorefinery applications.

Material and Methods

Chemicals and Plant Growth Condition

Chemicals and culture media for plant cultivation are purchased from PhytoTechnology Laboratories (Lenexa, KS). Hygromycin B is purchased from Gold Biotechnology (St. Louis, MO). All other chemicals are purchased from Sigma-Aldrich (St. Louis, MO).

Plant Material and Growth Conditions

*Arabidopsis thaliana* (ecotype Columbia, Col-0) is grown in a growth chamber (Percival Scientific, Perry, IA) with 150 $\mu$mol/m$^2$/s of light for 16 h per 24-h day cycle, 22° C., and 60% humidity. Prior transfer to soil, the selection of trans- genic plants is made on Murashige and Skoog vitamin medium, supplemented with 1% sucrose, 1.5% agar, and 25 $\mu$g/mL hygromycin. The Arabidopsis line pC4H::QsuB-1 is grown on the same medium supplemented with 50 $\mu$g/mL kanamycin prior transfer to soil (Eudes et al., 2015). For Arabidopsis biomass yields, the height of the main stem is measured at the mature senesced stage and all stems are harvested without leaves and siliques for total biomass dry weight measurements. Wild-type tobacco (*Nicotiana ben- thamiana*) seeds are germinated directly on soil and plants are grown in a growth chamber with 150 $\mu$mol/m$^2$/s of light for 16 h per 24-h day cycle, 25° C., and 60% humidity.

Cloning of Level-0 DNA Parts

The DNA coding sequences of plastid-targeted PmdA, PmdB, and PmdC from *C. testosteroni* are codon-optimized for expression in *A. thaliana* and synthesized as gene fragments by GenScript (Piscataway, NJ). All coding sequences contain at their 5'-end the sequence of the plastid transit peptide Schl2 from the *A. thaliana* chloroplastic photosystem II subunit S (AT1G44575) and flanking BsaI restriction sites plus extra homologous sequences for down- stream integration into pBca9145 using In-Fusion cloning (Takara Bio USA, Mountain View, CA) (Shih et al., 2016; Table 1). A gene sequence encoding feedback-insensitive AroG (L175Q) from *E. coli* preceded with a sequence encoding the chloroplast transit peptide Schl1 of the pea (*Pisum sativum*) ribulose-1,5-bisphosphate carboxylase small subunit (GenBank: AAG45569.1) is amplified by PCR with primers containing flanking BsaI restriction sites (Table 2) using the pDONR221-P3-schl1-aroG$^{L175Q}$-P2 construct as template (Eudes et al., 2018) and subcloned into the backbone pBca9145 by In-Fusion cloning. Similarly, a gene sequence encoding a 3-dehydroshikimate dehydratase (QsuB) from *C. glutamicum* preceded with a sequence encoding the synthetic chloroplast transit peptide Schl3 is amplified by PCR with primers containing flanking BsaI restriction sites (Table 2) using the plasmid pTKan-pC4H:: schl3::QsuB as template (Eudes et al., 2015) and subcloned into pBca9145. Finally, a 2377-bp sequence corresponding to the promoter pC3'H of the Arabidopsis coumarate 3'-hy- droxylase gene (At2g40890) is amplified by PCR with primers containing flanking BsaI restriction sites (Table 2) using *Arabidopsis thaliana* genomic DNA as template, and subcloned into pBca9145. All corresponding level-0 con- structs are listed in Table 3.

Plasmid Constructions

For transient expression in tobacco, synthetic sequences encoding Schl1-AroG*, Schl2-PmdA, Schl2-PmdB, Schl2- PmdC, schl1-LigI, schl2-pcaG, schl3-pcaH, and Schl3- QsuB are released by BsaI digest from the pBca9145 backbone and ligated individually into the binary vector pPMS057 which contains a 35S promoter (p35S) from the cauliflower mosaic virus (Belcher et al., 2020; Table 1). The resulting vectors containing p35S::Schl1-AroG*, p35S:: Schl2-PmdA, p35S::Schl2-PmdB, p35S::Schl2-PmdC, p35S::Schl2-pcaG, p35S::Schl3-pcaH, p35S::Schl1-LigI, and p35S::Schl3-QsuB are listed in Table 4. For stable Arabidopsis transformation, the jStack cloning method is used to generate the level-2 constructs pAroG, pPDC-4G, and pPDC-5G (Shih et al., 2016). Detailed information about the level-0, level-1, and level-2 plasmids used for jStack assemblies are listed in Tables 1, 3 and 5. Plasmid sequences are available at the Inventory of Composable Elements (ICE) source registry (website for: public-regis- try.jbei.org).

Tobacco Infiltration and Arabidopsis Transformation

Binary vectors are transformed into *Agrobacterium tume- faciens* strain GV3101 by electroporation and selection is made on Luria-Bertani (LB) solid medium with 50 mg/mL kanamycin, 30 mg/mL gentamycin, and 100 mg/mL rifam- picin. For transient expression in tobacco, leaves of 4-week- old plants are infiltrated with *Agrobacterium* strains (OD$_{600}$=1.0) carrying pPMS057 vectors of interest follow- ing the procedures described previously (Sparkes et al., 2006). For stable expression, the constructs are introduced into Arabidopsis via *Agrobacterium*-mediated transforma- tion (Bechtold and Pelletier, 1998). The stability in *Agro- bacterium* of the large binary vectors used for Arabidopsis transformation is verified by PCR using plasmid preps from overnight-grown *Agrobacterium* cultures as template (FIG. 1).

DNA Extraction and PCR Analysis

Arabidopsis genomic DNA is extracted using the DNeasy Plant Mini Kit (Qiagen, Valencia, CA) following the manu- facturer's protocol. Detection by PCR of the transgenes AroG*, QsuB, PmdA, PmdB, and PmdC from the pAroG, pPDC-4G, or pPDC-5G construct was conducted using the primers listed in Table 2.

Metabolite Extraction for LC-MS Metabolite Analysis

Metabolites are extracted from mature senesced dried Arabidopsis stems using 80% (v/v) methanol-water as sol- vent as previously described (Eudes et al., 2018). For each sample, 30 mg of ball-milled biomass is sequentially extracted four times with 1 mL of solvent at 70° C. The 4 mL extracts are mixed with 2 mL of HPLC grade water and cleared by centrifugation at 4,000× g for 5 minutes. After centrifugation, extracts are filtered through Amicon Ultra centrifugal filters (3 kDa MW cut off, EMD Millipore, Billerica, MA) at 12,000× g for 60 min at 4° C. For PCA quantification, a 500 $\mu$L aliquot of the filtered extracts is dried under vacuum and hydrolyzed with 1N HCl for 3 h at 90° C. to release the PCA aglycone form, followed by three ethyl acetate partitioning steps as previously described (Eudes et al., 2015). Metabolites are extracted with the same method from the harvested tobacco leaves, which are frozen, and pulverized in liquid nitrogen five days post-infiltration. Around 200 mg of frozen leaf disc is used for each extrac- tion.

LC-MS Metabolite Analysis

PCA and PDC are analyzed using an HPLC-ESI-TOF-MS as previously described (Eudes et al., 2013). Quantification of metabolites is performed via 6-point calibration curves of standard compounds. The theoretical m/z (negative ionization) of deprotonated PCA, PCA-glucose conjugate, and PDC are 153.01933, 315.07216, and 182.99351, respectively.

Lignin Measurements

Lignin is quantified from mature senesced dried Arabidopsis stems using the thioglycolic acid method as previously described (Suzuki et al., 2009). Dried cell wall residues (~15 mg) obtained after sequential metabolite extractions (see section 2.7) are used.

Biomass Pretreatment and Saccharification

Ball-milled senesced stems (10 mg) are mixed with 340 µL of 0.25% w/v NaOH and shaken at 1400 rpm (50° C., 60 min) for dilute alkaline pretreatment. Saccharification is initiated by adding 650 µL of 100 mM sodium citrate buffer pH 5 containing 80 µg/mL tetracycline and 0.05% w/w Cellic CTec3 cellulase (Novozymes, Davis, CA). After 96 h of incubation at 50° C. with shaking (800 rpm), samples are centrifuged and the supernatant is filtered through 0.45-µm nylon membrane centrifugal filters (VWR International, Radnor, PA) for glucose and xylose measurements using high-performance liquid chromatography (HPLC). The system is equipped with an Aminex cation-exchange resin column HPX-87H, 300×7.8 mm (Bio-Rad, Hercules, CA) and the eluant was 4 mM $H_2SO_4$ at a flow rate of 0.4 mL/min at 60° C. Glucose and xylose are identified by refractive index and their amount quantified using standard curves of authentic compounds.

Results

Production of PDC in Tobacco Leaves by Transient Expression of AroG*, QsuB, PCA 4,5-dioxygenase (PmdAB) and CHMS Dehydrogenase (PmdC)

Figure 2A:
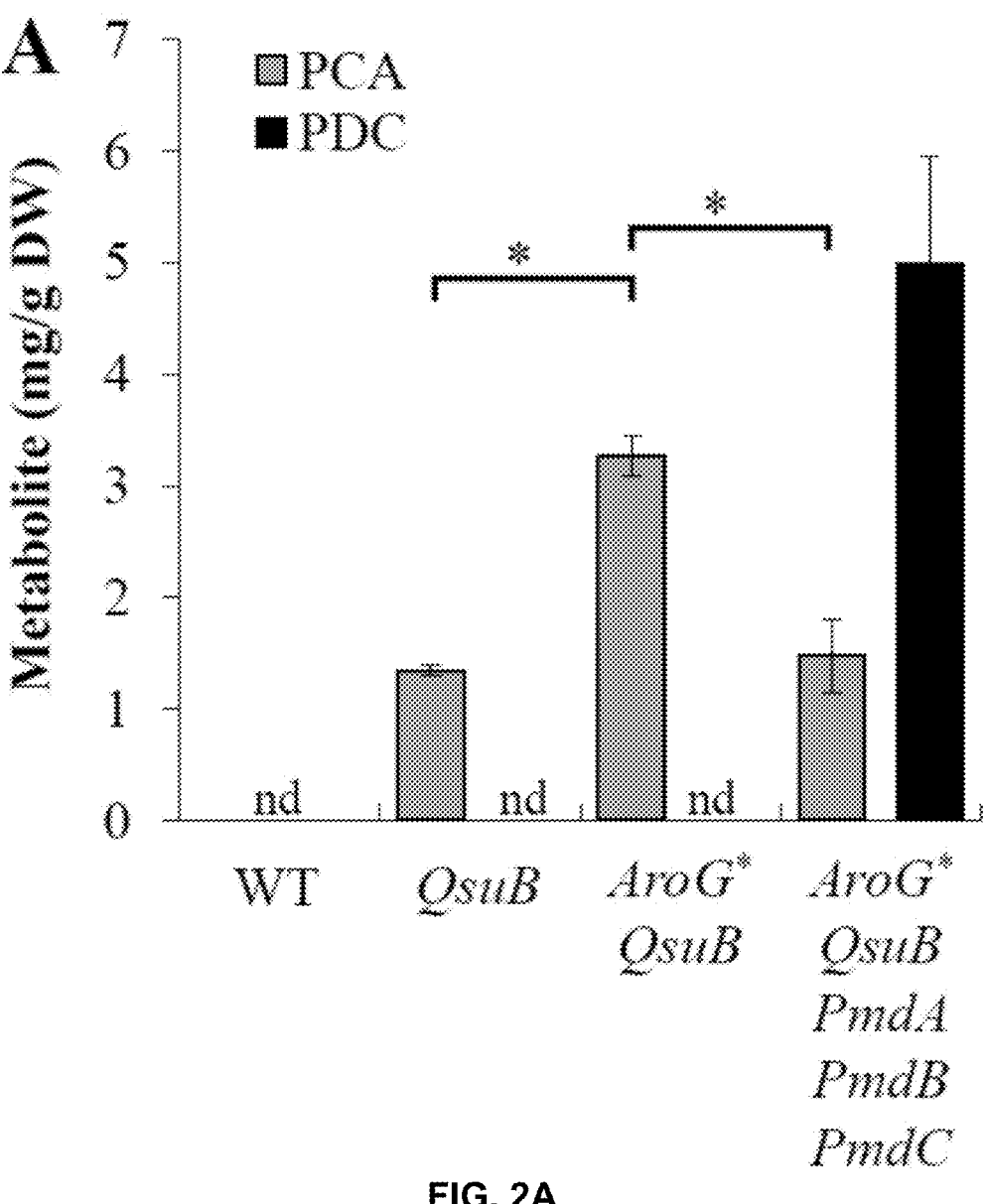
FIG. 2A. Production of PDC in tobacco leaves by transient expression of AroG*, QsuB, and the proposed PDC biosynthetic enzymes PmdA, PmdB, and PmdC. In-planta conversion of PCA into PDC requires co-expression of the PmdA, PmdB, and PmdC genes. Error bars represent the SE from three biological replicates (n=3). Asterisks indicate significant differences using the unpaired Student's t-test (*P<0.01). Nd, not detected.
Figure 2B:
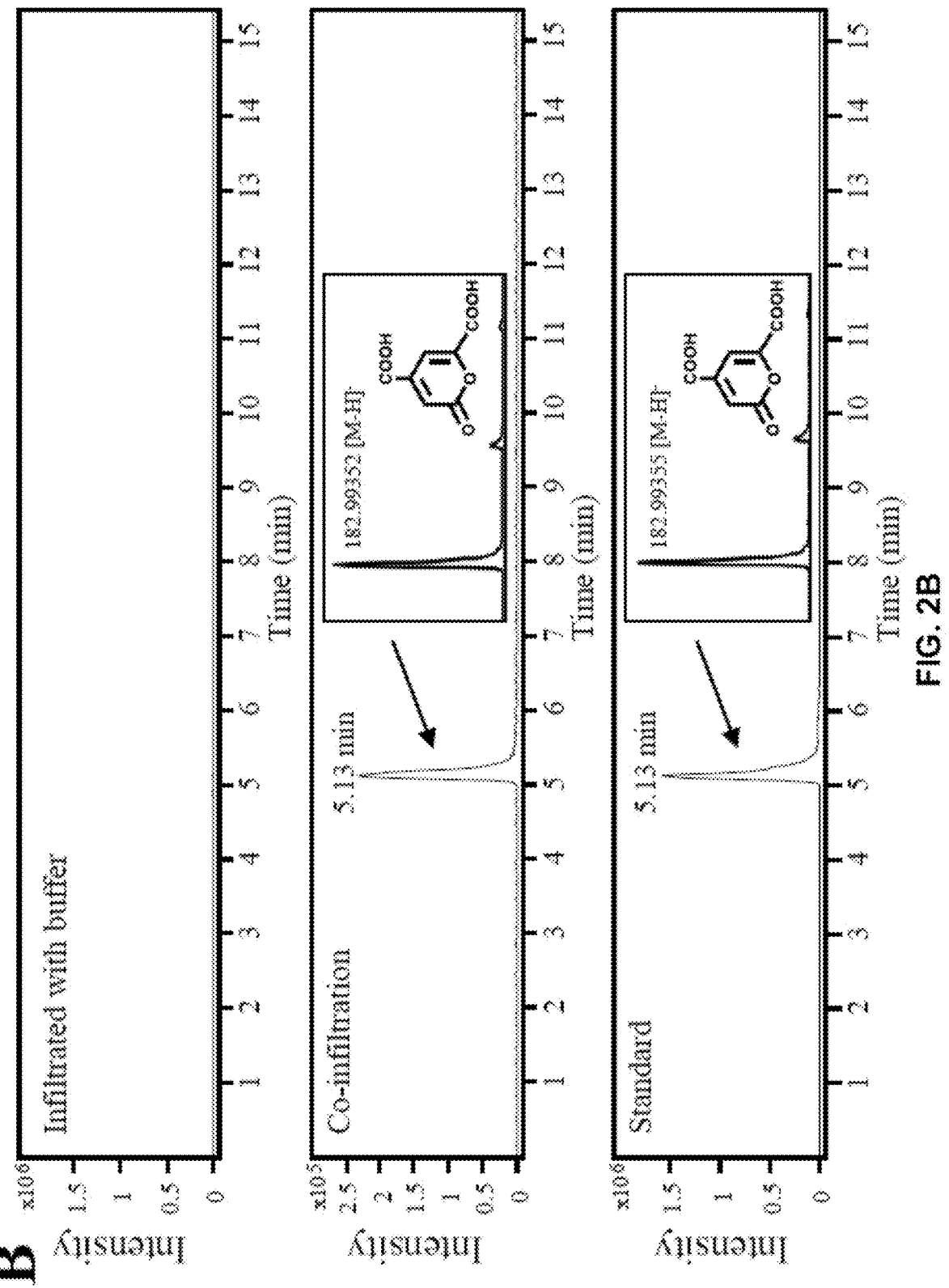
FIG. 2B. Production of PDC in tobacco leaves by transient expression of AroG*, QsuB, and the proposed PDC biosynthetic enzymes PmdA, PmdB, and PmdC. Representative HPLC-ESI-TOF MS chromatograms of metabolite extracts obtained from leaves infiltrated with buffer only (top panel) or co-infiltrated with AroG*, QsuB, pmdA, pmdB, and pmdC (middle panel) in comparison with a PDC standard solution (lower panel). Insets show PDC mass spectra.

It is previously showed that stable expression of plastid-targeted QsuB in tobacco (*Nicotiana tabacum* L.) leads to accumulation of PCA in plant tissues (Wu et al., 2017). Therefore, transiently plastid-targeted versions of QsuB, PmdA, PmdB, and PmdC are co-expressed in tobacco leaves to rapidly validate the use of these enzymes for production of PDC from PCA in planta. Plastid-targeted feedback-insensitive DAHP synthase AroG$^{L175Q}$ (AroG*) is also included to enhance the carbon flux through the shikimate pathway. Successfully, accumulation of PDC is observed in leaves infiltrated with the five bacterial genes, whereas expression of QsuB without PmdA, PmdB, and PmdC resulted only in the accumulation of a PCA glucose conjugate (FIG. 2A; FIG. 9). HPLC-ESI-TOF MS analysis of an authentic standard is used to assess the authenticity of PDC measured in metabolite extracts obtained from infiltrated tobacco leaves (FIG. 2B). It is also observed that co-infiltration of AroG* with QsuB increased the production of the PCA glucose conjugate by ~2.5-fold compared with infiltrations with QsuB alone, which validates the efficacy of AroG* at enhancing the carbon flux through the shikimate pathway (FIG. 2A). The amount of PCA is reduced upon expression of the Pmd genes, which indicates a conversion of PCA into PDC in the complete pathway (FIG. 2A). Finally, a combinatorial approach showed that all three enzymes PmdA, PmdB, and PmdC are necessary for de-novo PDC synthesis since omitting one of the Pmd genes abolished PDC production (FIG. 9). In addition, among the examined de novo biosynthetic pathways for PDC synthesis depicted in FIG. 12A, the route using AroG*, QsuB, PmdA, PmdB and PmdC showed as the most promising pathway to have highest titer

Enhancement of PCA Content in Arabidopsis Stems by Co-Expression of QsuB with Feedback-Insensitive AroG*

Figure 3:
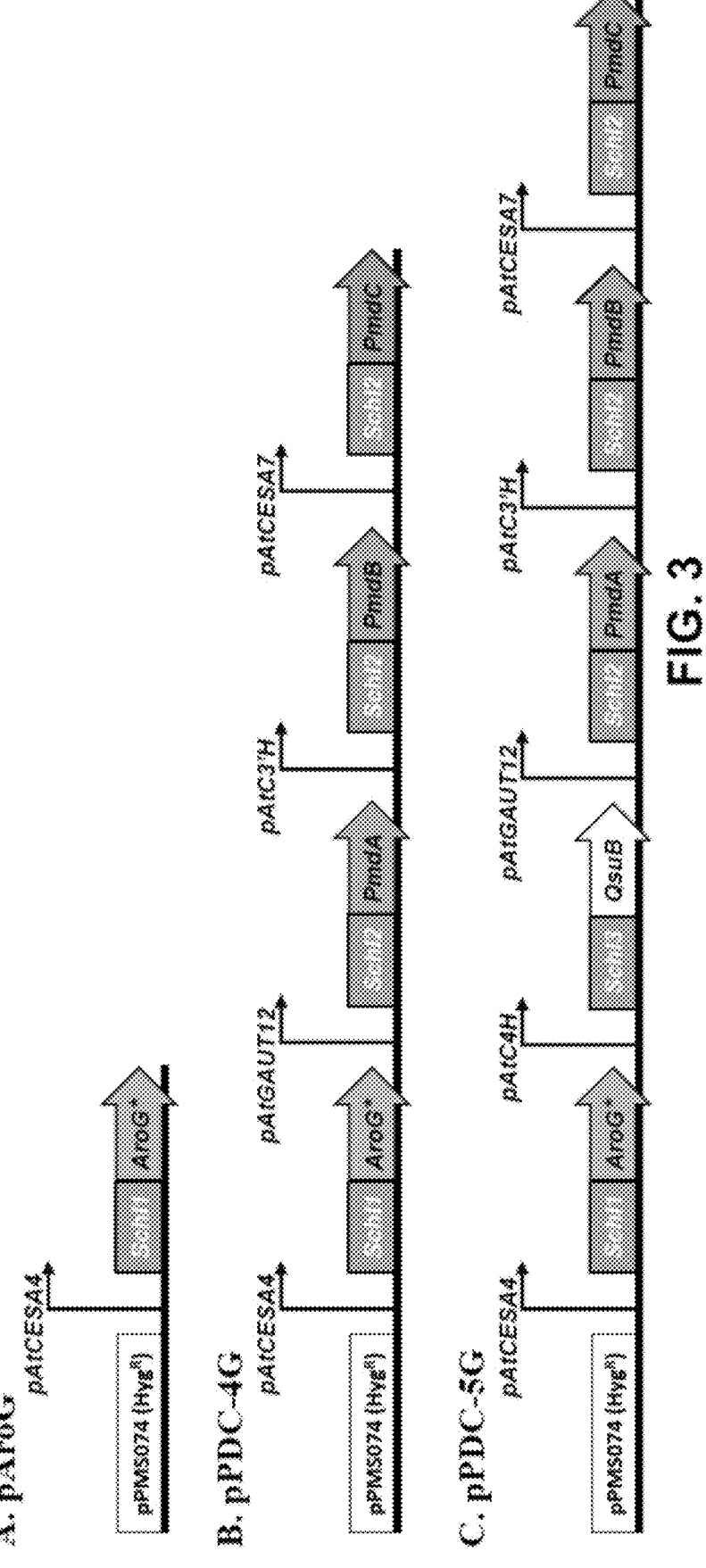
FIG. 3. Schematic representation of binary vectors used for Arabidopsis transformations. (A) AroG* expression cassette used for the transformation of an Arabidopsis QsuB background. (B) Construct used for the production of PDC in an Arabidopsis QsuB background (C) Construct used for the production of PDC in wildtype Arabidopsis. Boxes labeled "Schl" denote plastid transit peptides. Abbreviations are: Schl1, transit peptide of the sunflower (*Helianthus annuus*) ribulose-1,5-bisphosphate carboxylase small subunit (RuBisCo, GenBank: XP_021992670); Schl2, transit peptide from Arabidopsis chloroplastic photosystem II 22 kDa protein (GenBank: AT1G44575); Schl3, synthetic transit peptide from fused sunflower and maize RuBisCo small subunits (Lebrun et al., 1992). pAtCESA4, pAtC4H, pAt-GAUT12, pAtC3'H, and pAtCESA7 designate the promoters of Arabidopsis cellulose synthase 4 (At5G44030), cinnamate 4-hydroxylase (At2G30490), galacturonosyltransferase 12 (At5G54690), coumarate 3'-hydroxylase (AT2G40890), and cellulose synthase 7 (AT5G17420) genes, respectively. Hyg$^R$ denotes the aminoglycoside phosphotransferase marker gene used for plant selection.

An Arabidopsis line that express a plastid-targeted QsuB using the promoter of the cinnamate 4-hydroxylase gene (pAtC4H) (Eudes et al., 2015) is transformed with a construct (pAroG) for expression of plastid-targeted DAHP synthase AroG$^{L175Q}$ under the control of the Arabidopsis pAtCESA4 promoter for preferential expression in stems (FIG. 3, Panel A).

Figure 4:
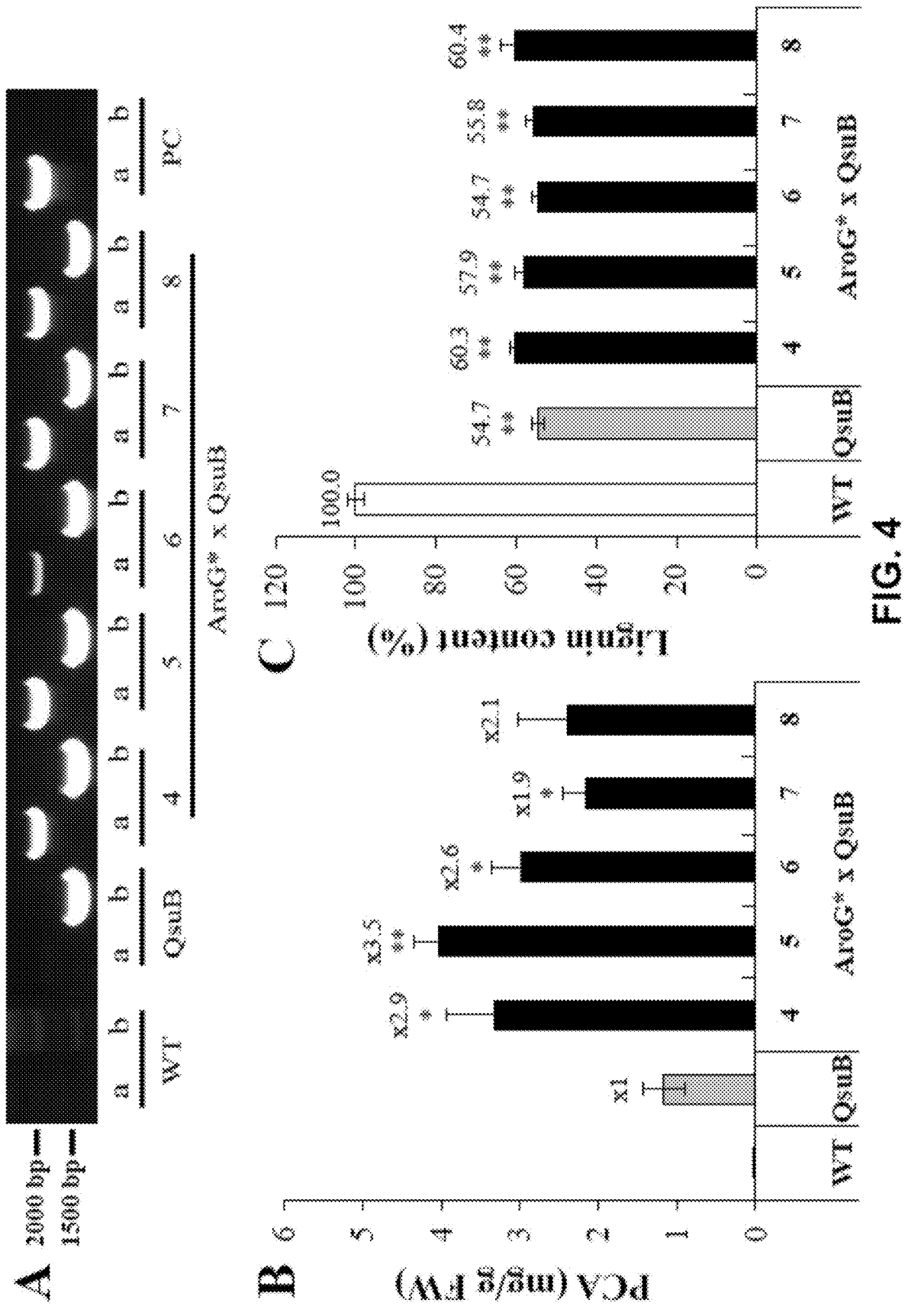
FIG. 4. Enhancement of PCA production in a transgenic QsuB Arabidopsis background by overexpressing feedback-resistant DAHP synthase (AroG*). (A) Detection by PCR of AroG* (a) and QsuB (b) in five independent transformants containing the pAroG cassette. The pAroG plasmid (PC) and gDNA obtained from Arabidopsis wildtype (WT) and the QsuB parental background (QsuB) were used as controls. (B) Comparison of the growth parameters (height and dry weight) between WT and transgenic Arabidopsis. (B) PCA titers and (C) lignin content in Arabidopsis wildtype (WT), QsuB parental background (QsuB), and AroG*xQsuB lines. Error bars represent the SE from four biological replicates (n=4). Asterisks indicate significant differences from the QsuB line (in B) or the wildtype (in C) using the unpaired Student's t-test (*P<0.05; **P<0.01).

Acid-hydrolyzed methanol extracts from five lines that contain both QsuB and AroG* transgenes show PCA titers up to 3.5-fold higher (0.4% dry weight) compared to those obtained from the parental line containing only QsuB (FIG. 4, Panels A and B). This result demonstrates that AroG* expression increases the carbon flux through the shikimate pathway and enables higher PCA synthesis in the Arabidopsis QsuB parental background.

It is previously reported that QsuB expression leads to strong reductions of lignin content in Arabidopsis stems, which is presumably a consequence of a reduction of the shikimate pool required for lignin biosynthesis (Eudes et al., 2015). Here, compared to wild-type plants, lignin content is reduced by 40-45% in stems of transgenic lines containing both QsuB and AroG*, indicating that AroG* expression does not fully restore lignin content in the Arabidopsis QsuB background (FIG. 4, Panel C).

Figure 5:
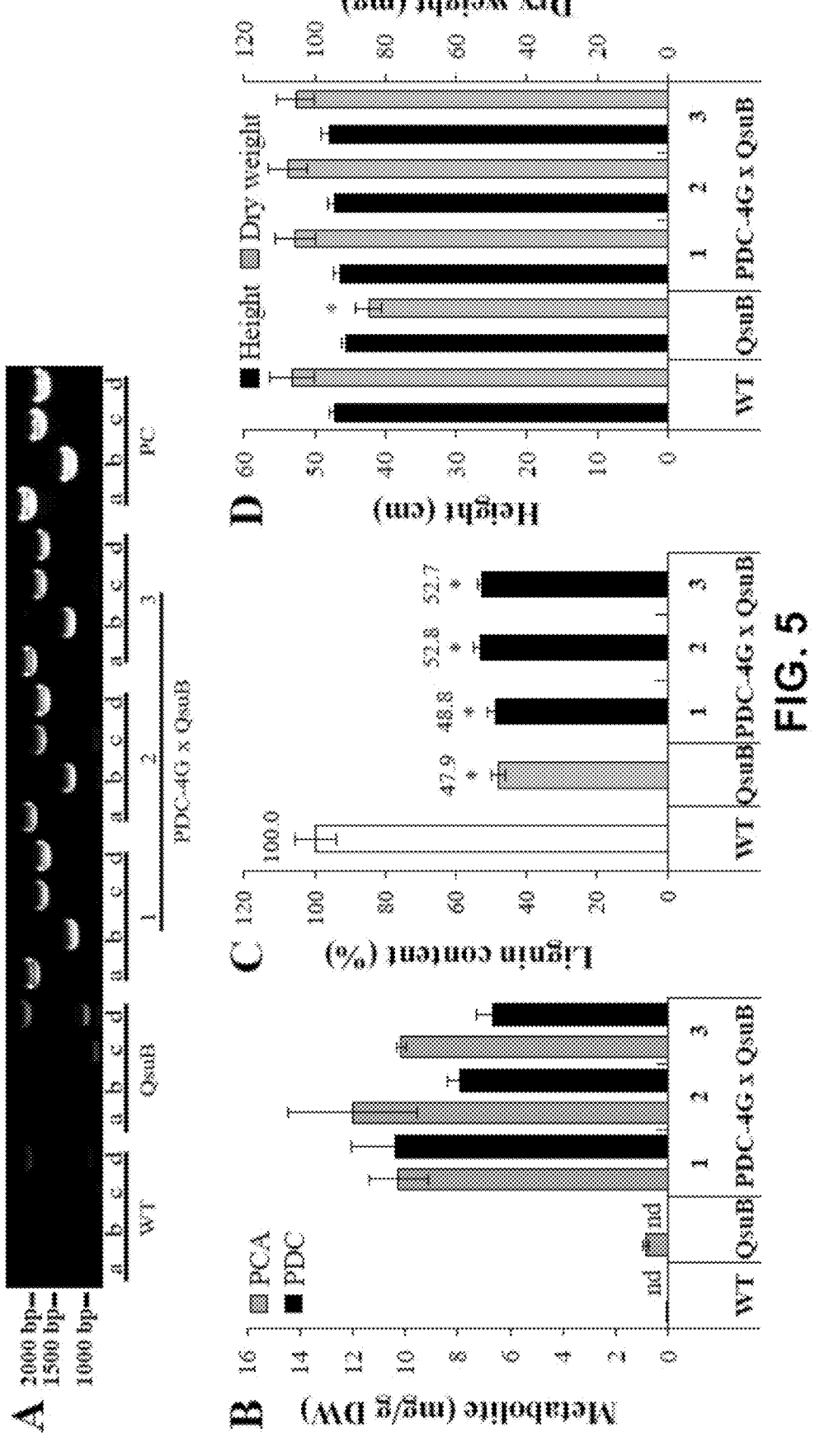
FIG. 5. Production of PDC in a transgenic QsuB Arabidopsis background. (A) Detection by PCR of AroG* (a), PmdA (b), PmdB (c), and PmdC (d) in three independent transformants containing the pPDC-4G construct. The pPDC-4G plasmid (PC) and gDNA obtained from Arabidopsis wildtype (WT) and the QsuB parental background (QsuB) were used as controls. (B) PCA and PDC titers and (C) lignin content in Arabidopsis wildtype (WT), QsuB parental background (QsuB), and PDC-4GxQsuB lines. Error bars represent the SE from four biological replicates (n=4). Nd, not detected. (D) Growth parameters (height and dry weight) of wild-type (WT) and transgenic Arabidopsis lines. Error bars represent the SE from twelve biological replicates (n=12). Asterisks indicate significant differences from the wild type using the unpaired Student's t-test (*P<0.01).

Production of PDC and Reduction of Lignin by Co-Expressing AroG*, PmdA, PmdB, and PmdC in a QsuB Arabidopsis Background Considering that AroG* expression elevated PCA titers in an Arabidopsis line containing the QsuB gene, a ~17-kb four gene construct (pPDC-4G) by stacking AroG* and the three PDC biosynthetic genes (PmdA, PmdB, and PmdC) is designed to produce PDC in this Arabidopsis QsuB background. The bacterial enzymes are targeted to plastids and expression of the corresponding genes is driven by promoters active in stem tissues that produce secondary cell wall such as fibers and xylem vessels (FIG. 3, Panel B). A preliminary metabolite screening is conducted to examine PDC production among the PDC-4G×QsuB transformants obtained in the T1 generation. Using LC-MS analysis, PDC is detected in methanol extracts obtained from stem biomass of twelve independent lines at the senesced mature stage, for which titers ranged from 1 to 9 mg/g DW and averaged 3.3±0.7 mg/g DW (FIG. 10). Next, the top three PDC-producing lines are further examined in the T2 generation. It is confirmed by PCR that these lines contain the AroG* and PmdABC genes in addition to the previously introduced QsuB gene (FIG. 5, Panel A), and validated the presence of PDC (ranging from 6.7 to 10.4 mg/g DW) in methanol-soluble metabolites extracted from stem biomass, which is not detected in extracts obtained from either wildtype or plants with QsuB alone (FIG. 5, Panel B). The drastic lignin reduction observed in the QsuB parental line is maintained in the PDC-4G×QsuB transgenics (ranging from 47 to 51%), which indicates a successful trait stacking for lignin reduction and in-planta accumulation of a value-added co-product (FIG. 5, Panel C). Lastly, transgenic lines harboring the pPDC-4G construct show no reduction of biomass yields compared with wild-type controls (FIG. 5, Panel D).

In-Planta PDC Production by Stacking AroG*, QsuB, PmdA, PmdB, and PmdC on a Single Construct The production of PDC is evaluated in plants transformed with a five-gene construct (pPDC-5G) that consists of a ~22-kb T-DNA containing AroG*, QsuB, and the three PDC biosynthetic genes PmdA, PmdB, and PmdC. In this construct, each gene is under the control of the same promoter used for the pPDC-4G construct, and the QsuB gene under the control of pAtC4H was included (FIG. 3, Panel C). A preliminary metabolite screening is conducted to examine PDC production among the PDC-5G transformants obtained in the T1 generation. PDC titers from the biomass of thirteen independent lines ranged between 4.5-36.7 mg/g DW and averaged 13.0±0.7 mg/g DW, which represents a significant increase compared to the titers achieved with the PDC-4G× QsuB primary transformants (FIG. 10). Six lines selected for further analyses show the presence of the five genes AroG*, QsuB, PmdA, PmdB, and PmdC in the T2 generation (FIG. 6A). For these lines, PDC amount in mature senesced stems range from 9.6 to 29.7 mg/g DW (FIG. 6B) and lignin content is reduced by 30-45% compared to wild-type plants (FIG. 6C). Importantly, most transgenic lines harboring the PDC-5G construct show no penalty in biomass yields compared with wild-type controls (FIG. 6D).

Biomass Saccharification Efficiency of PDC-Producing Plants

Biomass saccharification assays are performed to assess the cell wall recalcitrance of engineered PDC-producing lines. After a dilute alkaline pretreatment and a 96-h enzymatic digestion, higher release of glucose and xylose from the biomass of the engineered lines compared to wild-type controls is observed (FIG. 7). In conjunction with the reduction of lignin content measured in these lines, this result indicates a reduced recalcitrance of cellulose and xylan to enzymatic degradation. Improvements of saccharification efficiency ranged between 37% and 77% for glucose (FIG. 7, Panel A) and between 46% and 84% for xylose (FIG. 7, Panel B).

DISCUSSION AND CONCLUSIONS

PDC is a promising building block for diverse biodegradable polyesters and other polymers with novel functionalities. In this study, it is demonstrated for the first time that PDC synthesis can be achieved in plants, which represents a complementary approach to the microbial production systems previously described in the literature. Indeed, considering an integrated biorefinery process, bioenergy crops engineered with the strategy described in this work could potentially supply PDC as well as fermentable sugars for downstream PDC microbial production.

The highest PDC titers in biomass (~3% DW) are obtained with plants containing the five biosynthetic genes located on a single construct (pPDC-5G). These titers are higher than those achieved in plants transformed successively with constructs containing one gene (i.e., QsuB) and four genes (pPDC-4G), which is possibly the result of higher transgene expression in the pPDC-5G lines. Similar observations are made in sugarcane developed with a gene stacking approach using multiple or single vectors for overproduction of triacylglycerol (Parajuli et al., 2020), as well as engineered polyhydroxybutyrate producing switchgrass obtained either from the transformation of multigene constructs or by crossing individual transgenic lines (Somleva et al., 2008).

A significant amount of the PCA intermediate is detected in Arabidopsis PDC producing lines, suggesting that synchronizing the spatiotemporal expression of 3-dehydroshikimate dehydratase (QsuB) and PCA 4,5-dioxygenase (PmdAB) could enable higher PCA utilization and PDC production. Unlike transient expression experiments in tobacco leaves in which QsuB, PmdA, and PmdB are under the control of the same constitutive promoter (p35S), the stable Arabidopsis lines are engineered with different promoters to drive expression of the various biosynthetic genes. This approach is intended to avoid misassembling of expression cassettes using the yeast homologous recombination-based cloning method and to limit gene silencing effects that sometimes occur across generations in plants with multiple copies of the same transgene sequence (Vaucheret et al., 2001). Specifically, pAtC4H used to drive QsuB expression in Arabidopsis may have a broader expression pattern compared to pAtGAUT12 used for PmdA expression since pAtC4H is active in epidermal tissues in addition to vascular tissues that produce secondary cell walls (Bell-Lelong et al., 1997; Peña et al., 2007). Therefore, the use of synthetic promoters to coordinate the expression of PDC biosynthetic genes could represent a promising approach towards optimizing transgenes expression and enhancing PDC titers (Belcher et al., 2020). Furthermore, it is observed that a PCA glucose conjugate accumulates when QsuB is expressed in plastids, which indicates a transit of free PCA from plastids to the cytosol where UDP-glycosyltransferases are located (FIG. 11). Therefore, another level of engineering towards improving PDC titers could consist in the identification and disruption of PCA exporter(s) located on the chloroplast envelope in order to retain PCA more efficiently. Indeed, the translocation of carboxylated aromatics across compartmental membranes is predicted to be an active process and PCA transporters have been identified in plants and bacteria (Ishimaru et al., 2011; Mori et al., 2008; Vermaas et al., 2019). Finally, considering that our de-novo PDC pathway is confined to plastids, integrating the corresponding biosynthetic genes as operons into the chloroplast genome could promote PDC synthesis, but chloroplast transformation techniques applied to bioenergy crops remain to be developed (Jin and Daniell, 2015).

Besides employing a 3-dehydroshikimate dehydratase, overproduction of PCA can be achieved in plants by dual expression of plastid-targeted bacterial chorismate pyruvate-lyase and p-hydroxybenzoate hydroxylase (Eudes et al., 2016). This strategy reroutes chorismate, which is another intermediate of the shikimate pathway found upstream 3-dehydroshikimate (FIG. 1). Therefore, it would be interesting to evaluate whether combining this strategy with the expression of 3-dehydroshikimate dehydratase results in higher PCA titers in plant biomass.

The reduction of lignin in plants expressing a bacterial 3-dehydroshikimate dehydratase (QsuB) has been attributed to a reduction of the cytosolic shikimate pool available for HCT during biosynthesis rather than a modification of phenylalanine content which is unchanged in extracts from QsuB plants (Eudes et al., 2015). Interestingly, although co-expression of DAHPS (AroG*) with QsuB led to higher PCA production, presumably by increasing the carbon flux through the shikimate pathway, lignin content remains low in plants carrying AroG* and QsuB (FIG. 4, Panel C; FIG. 5, Panel C; and, FIG. 6C). Previous studies reported that expression of AroG$^{L175Q}$ does not affect lignin content in Arabidopsis stems despite its positive effect on the content of various shikimate-derived metabolites including soluble phenylpropanoids, glucosinolates, and flavonoids (Tzin et al., 2012). Extended metabolite analyses need to be conducted in the transgenic plants to identify the possible metabolic bottlenecks that prevent lignin restoration. Nevertheless, low lignin is a desirable trait in crops since lignin has a negative impact on biomass processability in various agroindustrial applications including the manufacturing of second-generation bioproducts (Carpita and McCann, 2020). As anticipated, the reduction of lignin content in PDC-producing lines is accompanied with improvements of biomass saccharification efficiency (FIG. 7), which suggests that total polysaccharide hydrolysis and the release of fermentable sugars could be achieved with reduced enzyme loadings.

Most Arabidopsis PDC producing lines show no reduction of biomass yields under controlled growth conditions (FIG. 5, Panel D; and FIG. 6D). These observations are encouraging and it will be important to evaluate plants' performance while transferring the engineering approach to bioenergy crops grown under field conditions. Glucose from lignocellulosic hydrolysates represent an attractive substrate for microbial synthesis of PDC, and a production yield of ~35% (0.35 g PDC/g glucose) have been achieved using an engineered *P. putida* strain (Johnson et al., 2019). Considering this production yield and glucan contents ranging between 30-40% DW in currently proposed bioenergy crops such as sorghum and switchgrass (van der Weijde et al., 2013), it is estimated that ~10.5-14 g of PDC can be potentially produced from 100 g of total biomass. Consequently, based on the best titers achieved with the present plant metabolic engineering approach (equivalent to 3 g PDC/100 g biomass), it is propose that PDC directly produced in crops could significantly contribute to overall PDC production in future biomass-based refineries that combine in-planta and microbial syntheses.

TABLE 1

List of vectors used for tobacco infiltrations and jStack clonings.

| Name | Level | Purpose | E. coli Ori | E. coli selection | JBEI ICE ID |
|---|---|---|---|---|---|
| pPMS057 | — | Tobacco. infiltration | pBR322 | Kanamycin | JBEI-19576 |
| pBca9145 | Level 0 | DNA parts isolation (j Stack) | ColEI | Carbenicillin | JBEI-19578 |
| pPMS028 | Level 1 | Intermediate cloning (jStack) | p15A | Chloramphenicol | JBEI-11601 |
| pPMS074 | Level 2 | Plant transformation (jStack) | ColEI | Kanamycin | JBEI-14584 |

TABLE 2

Primer used in this study.

| Primer name | Purpose/Target | Sequence (5'-3') |
|---|---|---|
| BsaI-schl1-aroG-Fw | Part isolation/chl1-aroG | cgctaaggatgatttctggaatt...T.ATGGCTTCTATG ATATCCTC (SEQ ID NO: 80) |
| BsaI-schl1-aroG-Rv | | cagctcgagttaggatcc...T...TCAACCCCTTCTT GCCTTAAC (SEQ ID NO: 81) |
| BsaI-schl3-qsuB-Fw | Part isolation/schl3-QsuB | cgctaaggatgatttctggaattc...T.ATGGCTTCGATC TCCTCCT (SEQ ID NO: 82) |
| BsaI-schl3-qsuB-Rv | | cagctcgagttaggatcc...T...TCAGTTTGGGATA CCTCTCTCTAAATC (SEQ ID NO: 83) |
| BsaI-pAtRef8-Fw | Part isolation/pAtRef8 | cgctaaggatgatttctggaattc...T...TAACACCTA TCTCAATTCATATTGAA (SEQ ID NO: 84) |
| BsaI-pAtRef8-Rv | | cagctcgagttaggatcc...A...AGTTTTGCTTCTA TTTTTATTTTCG (SEQ ID NO: 85) |
| Primer_1-F | Genotyping/AroG* from pAroBG and lines AroG* x | AGAAGTTGGAAGCTCAAGCAA (SEQ ID NO: 86) |
| Primer_1-R | Qsub | CCCATCTCATAAATAACGTCATGC (SEQ ID NO: 87) |

TABLE 2-continued

Primer used in this study.

| Primer name | Purpose/Target | Sequence (5'-3') |
|---|---|---|
| Primer_2-F | Genotyping/QsuB from lines AroG* x QsuB | CGCTACAGGAAGGTTAGGTGA (SEQ ID NO: 88) |
| Primer_2-R | | CACAGTTCGATAGCGAAAACCG (SEQ ID NO: 89) |
| Primer_3-F | Genotyping/AroG* in pPDC-4G and lines PDC-4G x QsuB | AGAAGTTGGAAGCTCAAGCAA (SEQ ID NO: 90) |
| Primer_3-F | | CGTAGATGAAAGACTGAGTGC (SEQ ID NO: 91) |
| Primer_4-F | Genotyping/PmdA in pPDC-4G and lines PDC-4G x QsuB | AGCGCATAACCGAGAAAACC (SEQ ID NO: 92) |
| Primer_4-F | | GGGAACAAAAGGAATAAAGAGGCA (SEQ ID NO: 93) |
| Primer_5-F | Genotyping/PmdB in pPDC-4G and lines PDC-4G x QsuB | CTCCACCAACTTTCCCCTACTT (SEQ ID NO: 94) |
| Primer_5-F | | CACAGTTCGATAGCGAAAACCG (SEQ ID NO: 95) |
| Primer_6-F | Genotyping/PmdC in pPDC-4G and lines PDC-4G x QsuB | GGAAACCGCGACGATGAAAG (SEQ ID NO: 96) |
| Primer_6-F | | CCCATCTCATAAATAACGTCATGC (SEQ ID NO: 97) |
| Primer_7-F | Genotyping/AroG* in pPDC-5G and lines PDC-5G | AGAAGTTGGAAGCTCAAGCAA (SEQ ID NO: 98) |
| Primer_7-F | | CGTAGATGAAAGACTGAGTGC (SEQ ID NO: 99) |
| Primer_8-F | Genotyping/QsuB in pPDC-5G and lines PDC-5G | CGCTACAGGAAGGTTAGGTGA (SEQ ID NO: 100) |
| Primer_8-F | | AGACAGATAAAGCCACGCACA (SEQ ID NO: 101) |
| Primer_9-F | Genotyping/PmdA in pPDC-5G and lines PDC-5G | AGCGCATAACCGAGAAAACC (SEQ ID NO: 102) |
| Primer_9-F | | CACAGTTCGATAGCGAAAACCG (SEQ ID NO: 103) |
| Primer_10-F | Genotyping/PmdB in pPDC-5G and lines PDC-5G | CTCCACCAACTTTCCCCTACTT (SEQ ID NO: 104) |
| Primer_10-F | | GGGAACAAAAGGAATAAAGAGGCA (SEQ ID NO: 105) |
| Primer_11-F | Genotyping/PmdC in pPDC-5G and lines PDC-5G | GGAAACCGCGACGATGAAAG (SEQ ID NO: 106) |
| Primer_11-F | | CCCATCTCATAAATAACGTCATGC (SEQ ID NO: 107) |

TABLE 3

List of level-0 DNA parts used in this study.

| Construct name | Backbone | Description | JBEI ICE ID |
|---|---|---|---|
| {P_AtCESA4} | pBca9145 | Arabidopsis cellulose synthase 4 (CESA4) promoter | JBx_062461 |
| {P_AtGAUT12} | pBca9145 | Arabidopsis galacturonosyl transferase 12 (GAUT12) promoter | JBx_062463 |
| {P_AtC3'H} | pBca9145 | Arabidopsis coumarate 3'-hydroxylase (C3'H) promoter | JBx_094582 |
| {P_AtC4H} | pBca9145 | Arabidopsis cinnamate 4-hydroxylase (C4H) promoter | JBx_042272 |
| {P_AtCESA7} | pBca9145 | Arabidopsis cellulose synthase 7 (CESA7) promoter | JBx_062465 |

TABLE 3-continued

List of level-0 DNA parts used in this study.

| Construct name | Backbone | Description | JBEI ICE ID |
|---|---|---|---|
| {C_schl1-aroG$^{L175Q9}$} | pBca9145 | Plastid-targeted feedback-resistant DAHPS (AroG L175Q) from *E. coli* (WP_032246946) | JBx_093489 |
| {C_schl2-pmdA} | pBca9145 | Plastid-targeted PCA 4,5-dioxygenase alpha chain (PmdA) from *C. testosterone* (GenBank: EHN65776.1) | JBx_142228 |
| {C_schl2-pmdB} | pBca9145 | Plastid-targeted PCA 4,5-dioxygenase beta chain (PmdB) from *C. testosterone* (GenBank: EHN65777.1) | JBx_142229 |

TABLE 3-continued

List of level-0 DNA parts used in this study.

| Construct name | Backbone | Description | JBEI ICE ID |
|---|---|---|---|
| {C_schl2-pmdC} | pBca9145 | Plastid-targeted CHMS dehydrogenase (PmdC) from *C. testosterone* (GenBank: EHN65778.1) | JBx_142230 |
| {C schl3-qsuB} | pBca9145 | Plastid-targeted 3-dehydroshimiate dehydratase (QsuB) from *C. glutamicum* (GenBank: YP_001137362.1) | JBx_092931 |
| {T_tG7} | pBca9145 | *Agrobacterium* tG7 terminator | JBx_042392 |
| {L_tG7} | pBca9145 | *Agrobacterium* tG7 linker | JBx_042394 |
| {T_tAtAct2} | pBca9145 | Arabidopsis actin 2 terminator | JBx_042324 |
| {L_tAtAct2} | pBca9145 | Arabidopsis actin 2 linker | JBx_042344 |
| {T_tAtRbcS} | pBca9145 | Arabidopsis Rubisco small subunit terminator | JBx_042282 |
| {L_tAtRbcS} | pBca9145 | Arabidopsis Rubisco small subunit linker | JBx_042288 |
| {T_tMAS} | pBca9145 | *Agrobacterium* mannopine synthase terminator | JBx_042284 |
| {L_tMAS} | pBca9145 | *Agrobacterium* mannopine synthase linker | JBx_042290 |
| {T_tNOS} | pBca9145 | *Agrobacterium* nopaline synthase terminator | JBx_042266 |
| {L_tOCS-Hyg$^R$} | pBca9145 | *Agrobacterium* octopine synthase terminator and plant hygromycin selectable marker, primary linker | JBx_065722 |

TABLE 4

List of plasmids used for transient expression in tobacco.

| Construct Name | Description | JBEI ICE ID |
|---|---|---|
| pPMS057-schl1-AroG* | Plastid-targeted feedback-resistant 3-deoxy-D-arabinoheptulosonate 7-phosphate synthase(DAHPS, AroG L175Q) from *E. coli* (WP_032246946) | JBx_097054 |
| pPMS057-schl2-PmdA | Plastid-targeted PCA 4,5-dioxygenase alpha chain (PmdA) from *C. testosterone* (GenBank: EHN65776.1) | JBx_100114 |
| pPMS057-schl2-PmdB | Plastid-targeted PCA 4,5-dioxygenase beta chain (PmdB) from *C. testosterone* (GenBank: EHN65776.1) | JBx_100115 |
| pPMS057-schl2-PmdC | Plastid-targeted CHMS dehydrogenase (PmdC) from *C. testosterone* (GenBank: EHN65778.1) | JBx_100116 |
| pPMS057-schl2-pcaG | Plastid-targeted PCA 3,4-dioxygenase alpha chain (PcaG) from *Pseudomonas putida* (GenBank: WP_003251601.1) | JBx_144875 |
| pPMS057-schl3-pcaH | Plastid-targeted PCA 3,4-dioxygenase beta chain (PcaH) from *Pseudomonas putida* (GenBank: WP_016489110.1) | JBx_144876 |
| pPMS057-schl1-LigI | Plastid-targeted 2-pyrone-4,6-dicarboxylate hydrolase (LigI) from *Sphingomonas paucimobilis* (GenBank: BAA33799.1) | JBx_144877 |
| pPMS057-schl3-QsuB | Plastid-targeted 3-dehydroshimiate dehydratase (QsuB) from *C. glutamicum* (GenBank: YP_001137362.1) | JBx_142226 |

TABLE 5

List of level-2 binary vectors and their intermediate level-1 constructs used in this study.

| Construct name | Level | Backbone | Description | JBEI ICE ID |
|---|---|---|---|---|
| pAroG | 2 | pPMS074 | tOCS-Hyg$^R$-pAtCESA4::schl1-aroG$^{L175Q}$-tNOS | JBx_102760 |
| tOCS-Hyg$^R$-pAtCESA4::schl1-aroG$^{L175Q}$-tNOS | 1 | pPMS028 | Level-1 construct obtained with level-0 parts: {L_tOCS-Hyg$^R$} {P_AtCESA4} {C_schl1-aroG$^{L175Q}$} {T_tNOS} | JBx_102758 |
| pPDC-4G | 2 | pPMS074 | tOCS-Hyg$^R$-pAtCESA4::schl1-aroG$^{L175Q}$-tG7-pAtGAUT12::schl2-pmdA-tAtAct2-pAtC3'H::schl2-pmdB-tAtRbcS-pAtCESA7::schl2-pmdC-tNOS | JBx_102759 |
| tOCS-Hyg$^R$-pAtCESA4::schl1-aroG$^{L175Q}$-tG7 | 1 | pPMS028 | Level-1 construct obtained with level-0 parts: {L_tOCS-Hyg$^R$} {P_AtCESA4} {C_schl1-aroG$^{L175Q}$} {T_tG7} | JBx_096298 |
| tG7-pAtGAUT12::schl2-pmdA-tAtAct2 | 1 | pPMS028 | Level-1 construct obtained with level-0 parts: {L_tG7} {P_AtGAUT12} {C_schl2-pmdA} {T_tAtAct2} | JBx_102755 |
| tAtAct2-pAtC3'H::schl2-pmdB-tAtRbcS | 1 | pPMS028 | Level-1 construct obtained with level-0 parts: {L_tAtAct2} {P_AtC3'H} {C_schl2-pmdB} {T_tAtRbcS} | JBx_102756 |
| tAtRbcS-pAtCESA7::schl2-pmdC-tNOS | 1 | pPMS028 | Level-1 construct obtained with level-0 parts: {L_tAtRbcS} {P_AtCESA7} {C_schl2-pmdC} {T_tNOS} | JBx_102757 |

TABLE 5-continued

List of level-2 binary vectors and their intermediate level-1 constructs
used in this study.

| Construct name | Level | Backbone | Description | JBEI ICE ID |
|---|---|---|---|---|
| tOCS-Hyg$^R$-pAtCESA4::schl1-aroG$^{L175Q}$-tG7 | 1 | pPMS028 | Level-1 construct obtained with level-0 parts: {L_tOCS-Hyg$^R$} {P_AtCESA4} {C_schl1-aroG$^{L175Q}$} {T_tG7} | JBx_096298 |
| tG7-pAtC4H::schl3-qsuB-tMAS | 1 | pPMS028 | Level-1 construct obtained with level-0 parts: {L_tG7} {P_AtC4H} {C_schl3-qsuB} {T_tMAS} | JBx_097321 |
| tMSA-pAtGAUT12::schl2-pmdA-tRBCS | 1 | pPMS028 | Level-1 construct obtained with level-0 parts: {L_tMSA} {P_AtGAUT12} {C_schl2-pmdA} {T_tRBCS} | JBx_144633 |
| tRBCS-pAtC3'H::schl2-pmdB-tAtAct2 | 1 | pPMS028 | Level-1 construct obtained with level-0 parts: {L_tRBCS} {P_AtC3'H} {C_schl2-pmdB} {T_tAtAct2} | JBx_144633 |
| tAtAct2-pAtCESA7::schl2-pmdC-tNOS | 1 | pPMS028 | Level-1 construct obtained with level-0 parts: {L_tAtAct2} {P_AtCESA7} {C_schl2-pmdC} {T_tNOS} | JBx_144635 |

REFERENCES CITED HEREIN

Altpeter, F., Springer, N. M., Bartley, L. E., Blechl, A. E., Brutnell, T. P., Citovsky, V., Conrad, L. J., Gelvin, S. B., Jackson, D. P., Kausch, A. P., Lemaux, P. G., Medford, J. I., Orozco-Cárdenas, M. L., Tricoli, D. M., Van Eck, J., Voytas, D. F., Walbot, V., Wang, K., Zhang, Z. J., Stewart, C. N., 2016. Advancing crop transformation in the era of genome editing. Plant Cell 28, 1510-1520.

Amore, A., Ciesielski, P. N., Lin, C.-Y., Salvachúa, D., Sànchez i Nogué, V., 2016. Development of lignocellulosic biorefinery technologies: Recent advances and current challenges. Aust. J. Chem. 69, 1201-1218.

Aznar, A., Chalvin, C., Shih, P. M., Maimann, M., Ebert, B., Birdseye, D. S., Loqué, D., Scheller, H. V., 2018. Gene stacking of multiple traits for high yield of fermentable sugars in plant biomass. Biotechnol. Biofuels 11:2.

Bailey-Serres, J., Parker, J. E., Ainsworth, E. A., Oldroyd, G. E. D., Schroeder, J. I., 2019. Genetic strategies for improving crop yields. Nature 575, 109-118.

Baral, N. R., Sundstrom, E. R., Das, L., Gladden, J., Eudes, A., Mortimer, J. C., Singer, S. W., Mukhopadhyay, A., Scown, C. D., 2019. Approaches for more efficient biological conversion of lignocellulosic feedstocks to biofuels and bioproducts. ACS Sustain. Chem. Eng. 7, 9062-9079.

Bechtold, N., Pelletier, G., 1998. In planta Agrobacterium-mediated transformation of adult Arabidopsis thaliana plants by vacuum infiltration. In: Martinez-Zapater, J. M., Salinas, J., Eds.), Arabidopsis Protocols. Humana Press, Totowa, NJ, pp. 259-266.

Belcher, M., Vuu, K., Zhou, A., Mansoori, N., Ramos, A., Thompson, M., Scheller, H., Loqué, D., Shih, P. M., 2020. Design of orthogonal regulatory systems for modulating gene expression in plants. Nat. Chem. Biol. 16, 857-865.

Bell-Lelong, D. A., Cusumano, J. C., Meyer, K., Chapple, C., 1997. Cinnamate-4-hydroxylase expression in Arabidopsis. Regulation in response to development and the environment. Plant Physiol. 113, 729-738.

Bito, M., Michinobu, T., Katayama, Y., Otsuka, Y., Nakamura, M., Ohara, S., Masai, E., Shigehara, K., 2008. 2-Pyrone-4,6-dicarboxylic acid as a source of green-plastics and antibacterial chemicals. Trans. Mater. Res. Soc. Japan 33, 1165-1168.

Börnke, F., Broer, I., 2010. Tailoring plant metabolism for the production of novel polymers and platform chemicals. Curr. Opin. Plant Biol. 13, 354-362.

Carpita, N. C., McCann, M. C., 2020. Redesigning plant cell walls for the biomass-based bioeconomy. J. Biol. Chem. doi: 10.1074/jbc.REV120.014561.

Eudes, A., Berthomieu, R., Hao, Z., Zhao, N., Benites, V. T., Baidoo, E. E. K., Loqué, D., 2018. Production of muconic acid in plants. Metab. Eng. 46, 13-19.

Eudes, A., Juminaga, D., Baidoo, E. E. K., Collins, F. W., Keasling, J. D., Loqué, D., 2013. Production of hydroxy-cinnamoyl anthranilates from glucose in Escherichia coli. Microb. Cell Fact. 12, 62.

Eudes, A., Liang, Y., Mitra, P., Loqué, D., 2014. Lignin bioengineering. Curr. Opin. Plant Biol. 26, 189-198.

Eudes, A., Pereira, J. H., Yogiswara, S., Wang, G., Teixeira Benites, V., Baidoo, E. E. K., Lee, T. S., Adams, P. D., Keasling, J. D., Loqué, D., 2016. Exploiting the substrate promiscuity of hydroxycinnamoyl-CoA:shikimate hydroxycinnamoyl transferase to reduce lignin. Plant Cell Physiol. 57, 568-579.

Eudes, A., Sathitsuksanoh, N., Baidoo, E. E. K., George, A., Liang, Y., Yang, F., Singh, S., Keasling, J. D., Simmons, B. A., Loqué, D., 2015. Expression of a bacterial 3-dehydroshikimate dehydratase reduces lignin content and improves biomass saccharification efficiency. Plant Biotechnol. J. 13, 1241-1250.

Hishida, M., Shikinaka, K., Katayama, Y., Kajita, S., Masai, E., Nakamura, M., Otsuka, Y., Ohara, S., Shigehara, K., 2009. Polyesters of 2-pyrone-4,6-dicarboxylic acid (PDC) as bio-based plastics exhibiting strong adhering properties. Polym. J. 41, 297-302.

Ishimaru, Y., Kakei, Y., Shimo, H., Bashir, K., Sato, Y., Sato, Y., Uozumi, N., Nakanishi, H., Nishizawa, N. K., 2011. A rice phenolic efflux transporter is essential for solubilizing precipitated apoplasmic iron in the plant stele. J. Biol. Chem. 286, 24649-24655.

Jin, S., Daniell, H., 2015. The engineered chloroplast genome just got smarter. Trends Plant Sci. 20, 622-640.

Johnson, C. W., Salvachúa, D., Rorrer, N. A., Black, B. A., Vardon, D. R., St. John, P. C., Cleveland, N. S., Dominick, G., Elmore, J. R., Grundl, N., Khanna, P., Martinez, C. R., Michener, W. E., Peterson, D. J., Ramirez, K. J., Singh, P., VanderWall, T. A., Wilson, A. N., Yi, X., Biddy, M. J., Bomble, Y. J., Guss, A. M., Beckham, G. T., 2019. Innovative chemicals and materials from bacterial aromatic catabolic pathways. Joule 3, 1523-1537.

Kang, M. J., Kim, H. T., Lee, M-W., Kim, K-A., Khang, T. U., Song, H. M., Park, S. J., Joo, J. C., Cha, H. G., 2020. A chemo-microbial hybrid process for the production of 2-pyrone-4,6-dicarboxylic acid as a promising bioplastic monomer from PET waste. Green Chem., 22, 3461-3469.

Lebrun, M., Leroux, B., Sailland, A., 1992. Gène chimère pour la transformation des plantes. European patent application. Patent Application No. EP 508909A1.

Lin, C-Y., Eudes, A., 2020. Strategies for the production of biochemicals in bioenergy crops. Biotechnol Biofuels. 13, 71.

Loqué, D., Scheller, H. V., Pauly, M., 2015. Engineering of plant cell walls for enhanced biofuel production. Curr. Opin. Plant Biol. 25, 151-161.

Luo, Z. W., Kim, W. J., Lee, S. Y., 2018. Metabolic engineering of Escherichia coli for efficient production of 2-pyrone-4,6-dicarboxylic acid from glucose. ACS Synth. Biol. 7, 2296-2307.

Markel, K., Belcher, M. S., Shih, P. M., 2020. Defining and engineering bioenergy plant feedstock ideotypes. Curr. Opin. Biotech. 62, 196-201.

Michinobu, T., Bito, M., Tanimura, M., Katayama, Y., Masai, E., Nakamura, M., Otsuka, Y., Ohara, S., Shigehara, K., 2010. Synthesis and characterization of hybrid biopolymers of L-lactic acid and 2-pyrone-4,6-dicarboxylic acid. J. Macromol. Sci. A. 47, 564-570.

Michinobu, T., Bito, M., Yamada, Y., Tanimura, M., Katayama, Y., Masai, E., Nakamura, M., Otsuka, Y., Ohara, S., Shigehara, K., 2009. Fusible, elastic, and biodegradable polyesters of 2-pyrone-4,6-dicarboxylic acid (PDC). Polym. J. 41, 1111-1116.

Michinobu, T., Hishida, M., Sato, M., Katayama, Y., Masai, E., Nakamura, M., Otsuka, Y., Ohara, S., Shigehara, K., 2008. Polyesters of 2-pyrone-4,6-dicarboxylic acid (PDC) obtained from a metabolic intermediate of lignin. Polym. J. 40, 68-75.

Mori, K., Kamimura, N., Masai, E., 2018. Identification of the protocatechuate transporter gene in Sphingobium sp. strain SYK-6 and effects of overexpression on production of a value-added metabolite. Appl. Microbiol. Biotechnol. 102, 4807-4816.

Nakajima, M., Nishino, Y., Tamura, M., Mase, K., Masai, E., Otsuka, Y., Nakamura, M., Sato, K., Fukuda, M., Shigehara, K., Ohara, S., Katayama, Y., Kajita, S., 2009. Microbial conversion of glucose to a novel chemical building block, 2-pyrone-4,6-dicarboxylic acid. Metab. Eng. 11, 213-220.

Otsuka, Y., Nakamura, M., Shigehara, K., Sugimura, K., Masai, E., Ohara, S., Katayama, Y., 2006. Efficient production of 2-pyrone 4,6-dicarboxylic acid as a novel polymer-based material from protocatechuate by microbial function. Appl. Microbiol. Biotechnol. 71, 608-614.

Parajuli, S., Kannan, B., Karan, R., Sanahuja, G., Liu, H., Garcia-Ruiz, E., Kumar, D., Singh, V., Zhao, H., Long, S., Shanklin, J., Altpeter, F., 2020. Towards oilcane: Engineering hyperaccumulation of triacylglycerol into sugarcane stems. GCB Bioenergy 12, 476-490.

Peña, M. J., Zhong, R., Zhou, G. K., Richardson, E. A., O'Neill, M. A., Darvill, A. G., York, W. S., Ye, Z. H., 2007 Arabidopsis irregular xylem8 and irregular xylem9: implications for the complexity of glucuronoxylan biosynthesis. Plant Cell 19, 549-563.

Perez, J. M., Kontur, W. S., Alherech, M., Coplien, J., Karlen, S. D., Stahl, S. S., Donohue, T. J., Noguera, D. R., 2019. Funneling aromatic products of chemically depolymerized lignin into 2-pyrone-4-6-dicarboxylic acid with Novosphingobium aromaticivorans. Green Chem. 21, 1340-1350.

Qian, Y., Otsuka, Y., Sonoki, T., Mukhopadhyay, B., Nakamura, M., Jellison, J., Goodell, B., 2016. Engineered microbial production of 2-pyrone-4,6-dicarboxylic acid from lignin residues for use as an industrial platform chemical. BioResources. 11, 6097-6109.

Shih, P. M., Vuu, K., Mansoori, N., Ayad, L., Louie, K. B., Bowen, B. P., Northen, T. R., Loqué, D., 2016. A robust gene-stacking method utilizing yeast assembly for plant synthetic biology. Nat. Commun. 7, 13215.

Shikinaka, K., Hashimoto, Y., Kajita, S., Masai, E., Katayama, Y., Nakamura, M., Otsuka, Y., Ohara, S., Shigehara, K., 2013. Thermoplastic polyesters of 2-pyrone-4,6-dicarboxylic acid (PDC) obtained from a metabolic intermediate of lignin. Sen'i Gakkaishi 69, 39-47.

Shikinaka, K., Otsuka, Y., Iguchi, Y., Nakamura, M., Itoh, Y., Masai, E., Katayama, Y., Shigehara, K., 2016. Preferential cesium ion trapping by 2-pyrone-4,6-dicarboxylic acid (PDC) obtained from a metabolic intermediate of lignin, a woody biomass resource. J. Nucl. Sci. Technol. 53, 1256-1259.

Shikinaka, K., Otsuka, Y., Nakamura, M., Masai, E., Katayama, Y., 2018. Utilization of lignocellulosic biomass via novel sustainable process. J. Oleo Sci. 67, 1059-1070.

Snell, K. D., Singh, V., Brumbley, S. M., 2015. Production of novel biopolymers in plants: recent technological advances and future prospects. Curr. Opin. Biotech. 32, 68-75.

Somleva, M. N., Snell, K. D., Beaulieu, J. J., Peoples, 0. P., Garrison, B. R., Patterson, N. A., 2008. Production of polyhydroxybutyrate in switchgrass, a value-added co-product in an important lignocellulosic biomass crop. Plant Biotechnol. J. 6, 663-678.

Sparkes, I. A., Runions, J., Kearns, A., Hawes, C., 2006. Rapid, transient expression of fluorescent fusion proteins in tobacco plants and generation of stably transformed plants. Nat. Protoc. 1, 2019-2025.

Suzuki, S., Suzuki, Y., Yamamoto, N., Hattori, T., Sakamoto, M., Umezawa, T., 2009. High-throughput determination of thioglycolic acid lignin from rice. Plant Biotechnol. 26, 337-340.

Tzin, V., Malitsky, S., Zvi, M. M. B., Bedair, M., Sumner, L., Aharoni, A., Galili, G., 2012. Expression of a bacterial feedback-insensitive 3-deoxy-d-arabino-heptulosonate 7-phosphate synthase of the shikimate pathway in Arabidopsis elucidates potential metabolic bottlenecks between primary and secondary metabolism. New Phytol. 194, 430-439.

Vanhercke, T., Dyer, J. M., Mullen, R. T., Kilaru, A., Rahman, M. M., Petrie, J. R., Green, A. G., Yurchenko, O., Singh, S. P., 2019. Metabolic engineering for enhanced oil in biomass. Prog. Lipid Res. 74, 103-129.

Van Der Weijde, T., Alvim Kamei, C. L., Torres, A. F., Vermerris, W., Dolstra, O., Visser, R. G. F., Trindade, L. M., 2013. The potential of C4 grasses for cellulosic biofuel production. Front. Plant Sci. 4, 1-18.

Vaucheret, H., Béclin, C., Elmayan, T., Feuerbach, F., Godon, C., Morel, J. B., Mourrain, P., Palauqui, J. C., Vernhettes, S., 1998. Transgene-induced gene silencing in plants. Plant J. 16, 651-659.

Vermaas, J. V., Dixon, R. A., Chen, F., Mansfield, S. D., Boerjan, W., Ralph, J., Crowley, M. F., Beckham, G. T., 2019. Passive membrane transport of lignin-related compounds. Proc. Natl. Acad. Sci. USA 116, 23117-23123.

Wilkes, S., Glasl, H., 2001. Isolation, characterization, and systematic significance of 2-pyrone-4,6-dicarboxylic acid in Rosaceae. Phytochemistry 58, 441-449.

Wu, W., Dutta, T., Varman, A. M., Eudes, A., Manalansan, B., Loqué, D., Singh, S., 2017. Lignin valorization: Two hybrid biochemical routes for the conversion of polymeric lignin into value-added chemicals. Sci. Rep. 7, 8420.

Yang, M., Baral, N. R., Simmons, B. A., Mortimer, J. C., Shih, P. M., Scown, C. D., 2020. Accumulation of high-value bioproducts in planta can improve the economics of advanced biofuels. Proc. Natl. Acad. Sci. U.S.A 117, 8639-8648.

Yuan, L., Grotewold, E., 2015. Metabolic engineering to enhance the value of plants as green factories. Metab. Eng. 27, 83-91.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A genetically modified plant or plant cell comprising nucleic acids encoding (a) PmdA subunit of protocatechuate 4,5-dioxygenase comprising an amino acid sequence having at least 90% amino acid identity with SEQ ID NO:1 and comprising all of SEQ ID NO: 12-17; (b) PmdB subunit of protocatechuate 4,5-dioxygenase comprising an amino acid sequence having at least 90% amino acid identity with SEQ ID NO:2 and comprising all of SEQ ID NO: 18-21 and 23-28; (c) 4-carboxy-2-hydroxymuconate-6-semialdehyde dehydrogenase (PmdC) comprising an amino acid sequence having at least 90% amino acid identity with SEQ ID NO:3 and comprising all of SEQ ID NO:29-41; (d) 3-dehydroshi-kimate dehydratase (QsuB) comprising an amino acid sequence having at least 90% amino acid identity with SEQ ID NO:11 and comprising all amino acids at positions 134, 165, 191, 239, 432, 506, and 582 of SEQ ID NO: 11; (e) a feedback-resistant DAHP synthase (AroG*) comprising an amino acid sequence having at least 90% amino acid identity with SEQ ID NO:5 and comprising all of SEQ ID NO: 42-47; (f) 2-pyrone-4,6-dicarboxylate hydrolase (LigI) com-prising an amino acid sequence having at least 90% amino acid identity with SEQ ID NO: 10 and comprising all amino acid residues at positions 47, 75, 122, 128, 154, 178, 246, and 251 of SEQ ID NO:10; (g) protocatechuate 3,4-dioxy-genase subunit alpha (PcaG) comprising an amino acid sequence having at least 90% amino acid identity with SEQ ID NO:8 and comprising all of SEQ ID NO:61-68; and, (h) protocatechuate 3,4-dioxygenase subunit beta (PcaH) com-prising an amino acid sequence having at least 90% amino acid identity with SEQ ID NO:9 and comprising all of SEQ ID NO:69-79; wherein each nucleic acid is operatively linked to a promoter, and the genetically modified plant or plant cell endogenously produces erythrose 4-phosphate (E4P) and phosphoenolpyruvate (PEP), chorismate (CHA), and synthesizes 2-pyrone-4,6-dicarboxylic acid (PDC).

2. A method for producing a PDC comprising: (a) growing or culturing the genetically modified plant or plant cell of claim 1 to produce a PDC, and (b) recovering the PDC produced from the plant or plant cell.

3. The genetically modified plant or plant cell of claim 1; wherein (a) the PmdA subunit comprises an amino acid sequence having at least 95% amino acid identity with SEQ ID NO:1; (b) the PmdB subunit comprises an amino acid sequence having at least 95% amino acid identity with SEQ ID NO:2; (c) the PmdC comprises an amino acid sequence having at least 95% amino acid identity with SEQ ID NO:3; (d) the QsuB comprises an amino acid sequence having at least 95% amino acid identity with SEQ ID NO:11; (e) the AroG* comprises an amino acid sequence having at least 95% amino acid identity with SEQ ID NO:5; (f) the LigI comprises an amino acid sequence having at least 95% amino acid identity with SEQ ID NO: 10; (g) the PcaG comprises an amino acid sequence having at least 95% amino acid identity with SEQ ID NO:8; and, (h) the PcaH comprises an amino acid sequence having at least 95% amino acid identity with SEQ ID NO:9.

4. The genetically modified plant or plant cell of claim 3; wherein (a) the PmdA subunit comprises an amino acid sequence having at least 99% amino acid identity with SEQ ID NO:1; (b) the PmdB subunit comprises an amino acid sequence having at least 99% amino acid identity with SEQ ID NO:2; (c) the PmdC comprises an amino acid sequence having at least 99% amino acid identity with SEQ ID NO:3; (d) the QsuB comprises an amino acid sequence having at least 99% amino acid identity with SEQ ID NO:11; (e) the AroG* comprises an amino acid sequence having at least 99% amino acid identity with SEQ ID NO:5; (f) the LigI comprises an amino acid sequence having at least 99% amino acid identity with SEQ ID NO: 10; (g) the PcaG comprises an amino acid sequence having at least 99% amino acid identity with SEQ ID NO:8; and, (h) the PcaH comprises an amino acid sequence having at least 99% amino acid identity with SEQ ID NO:9.

5. The genetically modified plant or plant cell of claim 4; wherein (a) the PmdA subunit comprises the amino acid sequence of SEQ ID NO:1; (b) the PmdB subunit comprises the amino acid sequence of SEQ ID NO:2; (c) the PmdC comprises the amino acid sequence of SEQ ID NO:3; (d) the QsuB comprises the amino acid sequence of SEQ ID NO:11; (e) the AroG* comprises the amino acid sequence of SEQ ID NO:5; (f) the LigI comprises the amino acid sequence of SEQ ID NO:10; (g) the PcaG comprises the amino acid sequence SEQ ID NO:8; and, (h) the PcaH comprises the amino acid sequence of SEQ ID NO: 9.

6. The method of claim 2; wherein (a) the PmdA subunit comprises an amino acid sequence having at least 95% amino acid identity with SEQ ID NO:1; (b) the PmdB subunit comprises an amino acid sequence having at least 95% amino acid identity with SEQ ID NO:2; (c) the PmdC comprises an amino acid sequence having at least 95% amino acid identity with SEQ ID NO:3; (d) the QsuB comprises an amino acid sequence having at least 95% amino acid identity with SEQ ID NO:11; (e) the AroG* comprises an amino acid sequence having at least 95% amino acid identity with SEQ ID NO:5; (f) the LigI com-prises an amino acid sequence having at least 95% amino acid identity with SEQ ID NO: 10; (g) the PcaG comprises an amino acid sequence having at least 95% amino acid identity with SEQ ID NO:8; and, (h) the PcaH comprises an amino acid sequence having at least 95% amino acid identity with SEQ ID NO:9.

7. The method of claim 6; wherein (a) the PmdA subunit comprises an amino acid sequence having at least 99% amino acid identity with SEQ ID NO:1; (b) the PmdB subunit comprises an amino acid sequence having at least 99% amino acid identity with SEQ ID NO:2; (c) the PmdC comprises an amino acid sequence having at least 99% amino acid identity with SEQ ID NO:3; (d) the QsuB comprises an amino acid sequence having at least 99% amino acid identity with SEQ ID NO: 11; (e) the AroG* comprises an amino acid sequence having at least 99% amino acid identity with SEQ ID NO:5; (f) the LigI com-prises an amino acid sequence having at least 99% amino acid identity with SEQ ID NO: 10; (g) the PcaG comprises an amino acid sequence having at least 99% amino acid identity with SEQ ID NO:8; and, (h) the PcaH comprises an amino acid sequence having at least 99% amino acid identity with SEQ ID NO:9.

8. The method of claim 7; wherein (a) the PmdA subunit comprises the amino acid sequence of SEQ ID NO: 1; (b) the PmdB subunit comprises the amino acid sequence of SEQ ID NO:2; (c) the PmdC comprises the amino acid sequence of SEQ ID NO:3; (d) the QsuB comprises the amino acid sequence of SEQ ID NO:11; (e) the AroG* comprises the amino acid sequence of SEQ ID NO: 5; (f) the LigI comprises the amino acid sequence of SEQ ID NO: 10; (g) the PcaG comprises the amino acid sequence of SEQ ID NO:8; and, (h) the PcaH comprises the amino acid sequence of SEQ ID NO:9.

9. The genetically modified plant or plant cell of claim 1, wherein the genetically modified plant or plant cell is capable of synthesizing 2.5 to 14.5 mg PDC per g FW.

10. The genetically modified plant or plant cell of claim 9, wherein the genetically modified plant or plant cell is capable of synthesizing 3.3 to 13.0 mg PDC per g FW.

11. The method of claim 2; wherein the growing or culturing step (a) comprises the genetically modified plant or plant cell producing 2.5 to 14.5 mg PDC per g FW.

12. The method of claim 11; wherein the growing or culturing step (a) comprises the genetically modified plant or plant cell producing 3.3 to 13.0 mg PDC per g FW.

* * * * *